United States Patent
Betts et al.

(10) Patent No.: US 12,060,332 B2
(45) Date of Patent: Aug. 13, 2024

(54) AURORA KINASE AND JANUS KINASE INHIBITORS FOR PREVENTION OF GRAFT VERSUS HOST DISEASE

(71) Applicant: H. LEE MOFFITT CANCER CENTER AND RESEARCH INSTITUTE, INC., Tampa, FL (US)

(72) Inventors: Brian Betts, Tampa, FL (US); Said M. Sebti, Tampa, FL (US); Harshani Lawrence, Tampa, FL (US); Nicholas Lawrence, Tampa, FL (US); Claudio Anasetti, Tampa, FL (US); Joseph Pidala, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 18/098,990

(22) Filed: Jan. 19, 2023

(65) Prior Publication Data

US 2023/0150948 A1    May 18, 2023

Related U.S. Application Data

(60) Continuation of application No. 17/555,786, filed on Dec. 20, 2021, now abandoned, which is a division of
(Continued)

(51) Int. Cl.
*C07D 239/48* (2006.01)
*A61K 31/505* (2006.01)
(Continued)

(52) U.S. Cl.
CPC .......... *C07D 239/48* (2013.01); *A61K 31/505* (2013.01); *A61K 31/506* (2013.01);
(Continued)

(58) Field of Classification Search
CPC ... C07D 239/48; A61K 31/505; A61K 31/506
See application file for complete search history.

(56) References Cited

U.S. PATENT DOCUMENTS 4,559,157 A   12/1985 Smith et al.
4,608,392 A   8/1986 Jacquet et al.
(Continued)

FOREIGN PATENT DOCUMENTS

WO   2005/013996   2/2005
WO   2012/135641   10/2012

OTHER PUBLICATIONS

Acute Leukemia, Merck Manual (Online Edition) 6 pages, pp. 1-6 (2013).*
(Continued)

*Primary Examiner* — Deepak R Rao
(74) *Attorney, Agent, or Firm* — Meunier Carlin & Curfman LLC

(57) ABSTRACT

Disclosed herein are compounds and methods for reducing the risk of developing, preventing, or treating graft versus host disease (GVHD) in a subject. The compounds can concurrently block Aurora kinase A and JAK2 signal transduction which synergistically suppresses alloreactive human T-cells in vitro, prevents xenogeneic graft-versus-host disease without impairing anti-tumor responses, and promotes the development and suppressive potency of CD39+ inducible $T_{reg}$. In certain aspects, disclosed are compounds of Formula I-V.

(Continued)

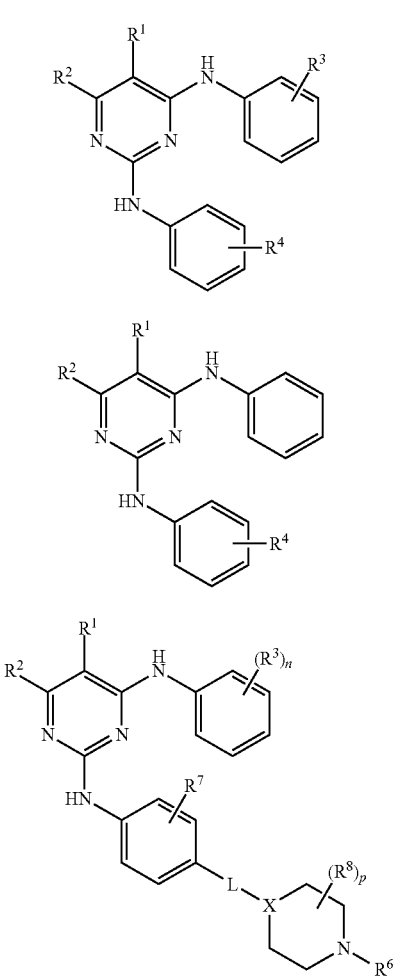

3 Claims, 21 Drawing Sheets

Related U.S. Application Data application No. 16/083,681, filed as application No. PCT/US2017/022074 on Mar. 13, 2017, now Pat. No. 11,203,576.

(60) Provisional application No. 62/307,030, filed on Mar. 11, 2016.

(51) Int. Cl.
   A61K 31/506   (2006.01)
   A61K 45/06    (2006.01)
   A61P 35/00    (2006.01)
   C07D 401/12   (2006.01)
   C07D 403/12   (2006.01)

(52) U.S. Cl.
   CPC ............. A61K 45/06 (2013.01); A61P 35/00 (2018.01); C07D 401/12 (2013.01); C07D 403/12 (2013.01)

(56) References Cited

U.S. PATENT DOCUMENTS

| | | |
|---|---|---|
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 6,649,608 B2 | 11/2003 | Pease et al. |
| 6,960,648 B2 | 11/2005 | Bonny |
| 7,122,542 B2 | 10/2006 | Singh et al. |
| 7,153,964 B2 | 12/2006 | Pease et al. |
| 7,560,458 B2 | 7/2009 | Freyne et al. |
| 7,906,644 B2 | 3/2011 | Sing et al. |
| 8,044,201 B2 | 10/2011 | Xu et al. |
| 8,211,929 B2 | 7/2012 | Chen et al. |
| 8,304,422 B2 | 11/2012 | Atuegbu et al. |
| 2002/0035243 A1 | 3/2002 | Imfeld et al. |
| 2002/0120100 A1 | 8/2002 | Bonny |
| 2003/0032594 A1 | 2/2003 | Bonny |
| 2006/0063789 A1 | 3/2006 | Freyne et al. |
| 2011/0152518 A1 | 6/2011 | Li et al. |
| 2012/0253039 A1 | 10/2012 | Singh et al. |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Aliagas-Martin, I. et al., "A Class of 2,4-Bisanilinopyrimidine Aurora A Inhibitors with Unusually High Selectivity against Aurora B," Journal of Medicinal Chemistry, 2009, vol. 52, No. 10, pp. 3300-3307 (Abstract).
Betts et al., CD4+ T cell STAT3 phosphorylation precedes acute GVHD, and subsequent Th17 tissue invasion correlates with GVHD severity and therapeutic response. Journal of leukocyte biology 97, 807 (Feb. 6, 2015).
Betts et al., Janus kinase-2 inhibition induces durable tolerance to alloantigen by human dendritic cell-stimulated T cells yet preserves immunity to recall antigen. Blood 118, 5330 (Nov. 10, 2011).
Betts, et al., Anti-IL6-receptor-alpha (tocilizumab) does not inhibit human monocyte-derived dendritic cell maturation or alloreactive T-cell responses. Blood 118, 5340 (Nov. 10, 2011).
Betts, et al., STAT5 polarization promotes iTregs and suppresses human T-cell alloresponses while preserving CTL capacity. Journal of leukocyte biology 95, 205 (Feb. 2014).
Carmena, et al., The cellular geography of aurora kinases. Nature reviews. Molecular cell biology 4, 842 (Nov. 2003).
Chemical Abstract compound, STN express. RN 844435-10-5, entered STN: Mar. 8, 2005.
Choi et al., Pharmacologic blockade of JAK1/JAK2 reduces GvHD and preserves the graft-versus-leukemia effect. PloS one 9, e109799 (2014).
Chou, Theoretical basis, experimental design, and computerized simulation of synergism and antagonism in drug combination studies. Pharmacological reviews 58, 621 (Sep. 2006).
Cooke et al., An experimental model of idiopathic pneumonia syndrome after bone marrow transplantation: I. The roles of minor H antigens and endotoxin. Blood 88, 3230 (Oct. 15, 1996).
Cutler et al., Tacrolimus/sirolimus vs tacrolimus/methotrexate as GVHD prophylaxis after matched, related donor allogeneic HCT. Blood 124, 1372 (Aug. 21, 2014).
Defaux, Julien et al., Discovery of 7-Aryl-Substituted (1,5-Maphthyridin-4-yl)ueras as Aurora Kinase Inhibitors. ChemMedChem 2014, 4, 9, 218-232.

(56) References Cited

OTHER PUBLICATIONS

Furlan et al., Transcriptome analysis of GVHD reveals aurora kinase A as a targetable pathway for disease prevention. Science translational medicine 7, 315ra191 (Nov. 25, 2015).
Heine et al., The JAK-inhibitor ruxolitinib impairs dendritic cell function in vitro and in vivo. Blood 122, 1192 (Aug. 15, 2013).
Heine, et al., Ruxolitinib is a potent immunosuppressive compound: is it time for anti-infective prophylaxis? Blood 122, 3843 (Nov. 28, 2013).
Heninger et al., IL-7 abrogates suppressive activity of human CD4+CD25+FOXP3+ regulatory T cells and allows expansion of alloreactive and autoreactive T cells. Journal of immunology 189, 5649 (Dec. 15, 2012).
Johnston et al., Sirolimus and mycophenolate mofetil as GVHD prophylaxis in myeloablative, matched-related donor hematopoietic cell transplantation. Bone marrow transplantation 47, 581 (Apr. 2012).
Kanakry et al., Single-agent GVHD prophylaxis with posttransplantation cyclophosphamide after myeloablative, HLA-matched BMT for AML, ALL, and MDS. Blood 124, 3817 (Dec. 11, 2014).
Kennedy et al., Addition of interleukin-6 inhibition with tocilizumab to standard graft-versus-host disease prophylaxis after allogeneic stem-cell transplantation: a phase 1/2 trial. The Lancet. Oncology 15, 1451 (Dec. 2014).
Laurence et al., STAT3 transcription factor promotes instability of nTreg cells and limits generation of iTreg cells during acute murine graft-versus-host disease. Immunity 37, 209 (Aug. 24, 2012).
Lawrence et al., Development of o-chlorophenyl substituted pyrimidines as exceptionally potent aurora kinase inhibitors. Journal of medicinal chemistry 55, 7392 (Sep. 13, 2012).
Lens, et al., Shared and separate functions of polo-like kinases and aurora kinases in cancer. Nature reviews. Cancer 10, 825 (Dec. 2010).
Liu et al., CD127 expression inversely correlates with FoxP3 and suppressive function of human CD4+ T reg cells. The Journal of experimental medicine 203, 1701 (Jul. 10, 2006).
Mandapathil et al., Generation and accumulation of immunosuppressive adenosine by human CD4+CD25highFOXP3+ regulatory T cells. The Journal of biological chemistry 285, 7176 (Mar. 5, 2010).
Manfredi et al., Characterization of Alisertib (MLN8237), an investigational smallmolecule inhibitor of aurora A kinase using novel in vivo pharmacodynamic assays. Clinical cancer research: an official journal of the American Association for Cancer Research 17, 7614 (Dec. 15, 2011).
Neri et al., Calcein-acetyoxymethyl cytotoxicity assay: standardization of a method allowing additional analyses on recovered effector cells and supernatants. Clinical and diagnostic laboratory immunology 8, 1131 (Nov. 2001).
Pasquini et al., Comparative outcomes of donor graft CD34+ selection and immune suppressive therapy as graft-versus-host disease prophylaxis for patients with acute myeloid leukemia in complete remission undergoing HLA-matched sibling allogeneic hematopoietic cell transplantation. Journal of clinical oncology: official journal of the American Society of Clinical Oncology 30, 3194 (Sep. 10, 2012).
Peres et al., Low expression of CD39 on regulatory T cells as a biomarker for resistance to methotrexate therapy in rheumatoid arthritis. Proceedings of the National Academy of Sciences of the United States of America 112, 2509 (Feb. 24, 2015).
Pidala et al., A randomized phase II study to evaluate tacrolimus in combination with sirolimus or methotrexate after allogeneic hematopoietic cell transplantation. Haematologica 97, 1882 (Dec. 2012).
Pidala et al., Prolonged sirolimus administration after allogeneic hematopoietic cell transplantation is associated with decreased risk for moderate-severe chronic graft vs. host disease. Haematologica 100(7) 970, (Apr. 3, 2015).
Samarasinghe et al., Functional characterization of alloreactive T cells identifies CD25 and CD71 as optimal targets for a clinically applicable allodepletion strategy. Blood 115, 396 (Jan. 14, 2010).
Seddiki et al., Expression of interleukin (IL)-2 and IL-7 receptors discriminates between human regulatory and activated T cells. The Journal of experimental medicine 203, 1693 (Jul. 10, 2006).
Singh et al., Superiority of rapamycin over tacrolimus in preserving nonhuman primate Treg half-life and phenotype after adoptive transfer. American journal of transplantation: official journal of The American Society of Transplantation and the American Society of Transplant Surgeons 14, 2691 (Dec. 2014).
Song, et al., The kinases aurora B and mTOR regulate the G1-S cell cycle progression of T lymphocytes. Nature immunology 8, 64 (Jan. 2007).
Spoerl et al., Activity of therapeutic JAK 1/2 blockade in graft-versus-host disease. Blood 123, 3832 (Jun. 12, 2014).
Tan et al., Induction of alloantigen-specific hyporesponsiveness in human T lymphocytes by blocking interaction of CD28 with its natural ligand B7/BB1. The Journal of experimental medicine 177, 165 (Jan. 1, 1993).
Thiolat et al., Interleukin-6 receptor blockade enhances CD39+ regulatory T cell development in rheumatoid arthritis and in experimental arthritis. Arthritis & rheumatology 66, 273 (Feb. 2014).
Touil et al., Depletion of T regulatory cells through selection of CD127-positive cells results in a population enriched in memory T cells: implications for anti-tumor cell therapy. Haematologica 97, 1678 (Nov. 2012).
Vaeth et al., Selective NFAT targeting in T cells ameliorates GvHD while maintaining antitumor activity. Proceedings of the National Academy of Sciences of the United States of America 112, 1125 (Jan. 27, 2015).
Vukmanovic-Stejic et al., The kinetics of CD4+Foxp3+ T cell accumulation during a human cutaneous antigen-specific memory response in vivo. The Journal of clinical investigation 118, 3639 (Nov. 2008).
Yang et al., Dual Aurora A and JAK2 kinase blockade effectively suppresses malignant transformation. Oncotarget 5, 2947 (May 30, 2014).
Yu, et al., CD28-specific antibody prevents graft versus-host disease in mice. Journal of immunology 164, 4564 (May 1, 2000).
Zeiser et al., Differential impact of mammalian target of rapamycin inhibition on CD4+CD25+Foxp3+ regulatory T cells compared with conventional CD4+ T cells. Blood 111, 453 (Jan. 1, 2008).
Zeiser et al., Inhibition of CD4+CD25+ regulatory T-cell function by calcineurindependent interleukin-2 production. Blood 108, 390 (Jul. 1, 2006).
Zeiser et al., Ruxolitinib in corticosteroid-refractory graft-versus-host disease after allogeneic stem cell transplantation: a multi-center survey. Leukemia 29(10) 2062 (Jul. 31, 2015).
International Search Report and Written Opinion of PCT/US2017/022074, mailed Mar. 13, 2017. 16 pages.
International Preliminary Report on Patentability issued for Application No. PCT/US2017/022074, dated Sep. 20, 2018, 9 pages.
Lum et al., 2,5-diaminopyrimidines and 3,5-disubstituted azapurines as inhibitors of glycogen synthase kinase-3 (GSK-3), Bioorganic & Medicinal Chemistry Letters, vol. 18, No. 12, pp. 3578-3581 (2008).
Hu et al., Exploring the Scaffold Universe of Kinase Inhibitors, Journal of Medicinal Chemistry, vol. 58, No. 1, pp. 315-332 (2015).
Li et al., CAPLUS Abstract 163:427238 (2015).

\* cited by examiner

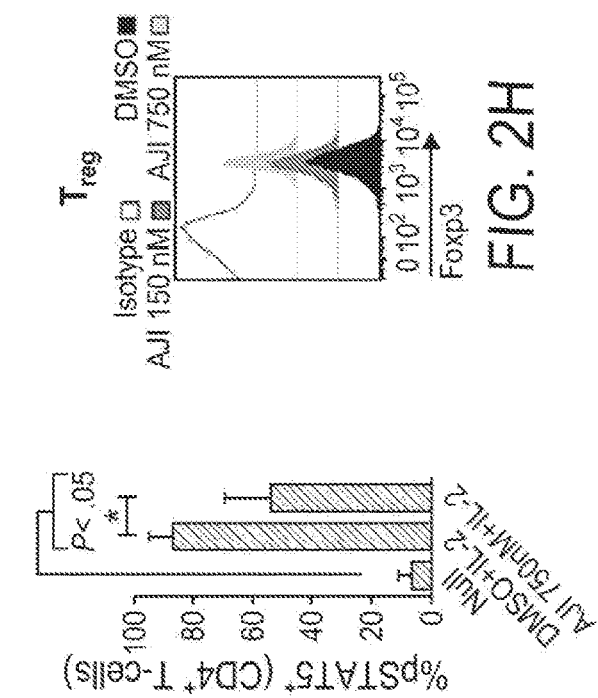
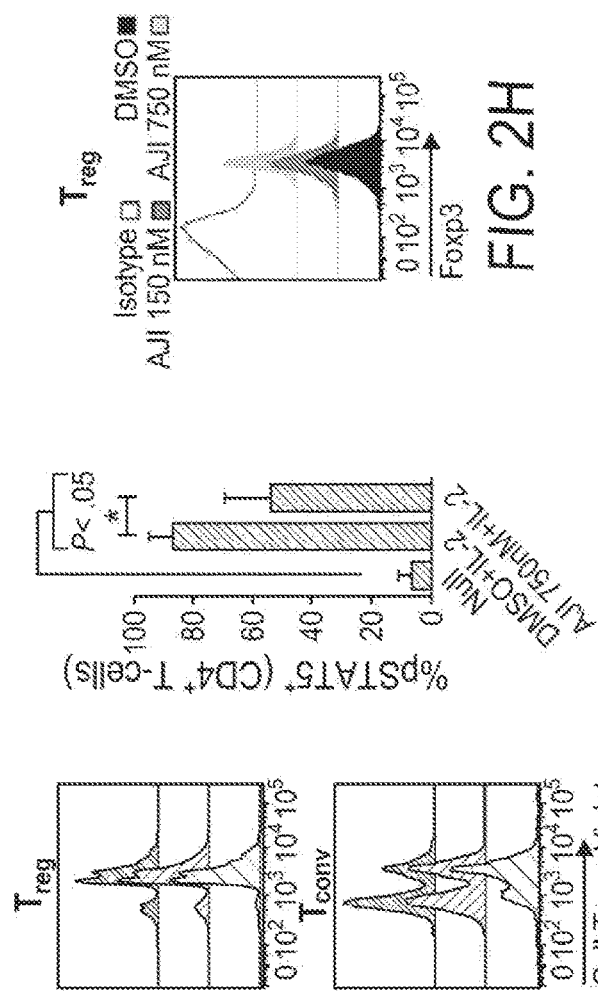
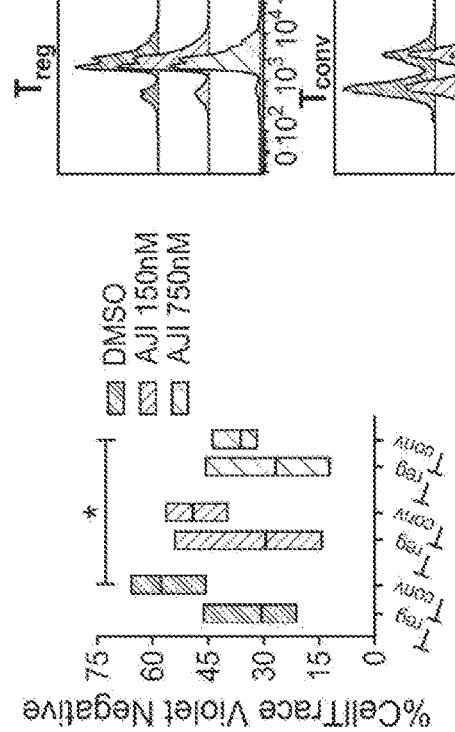
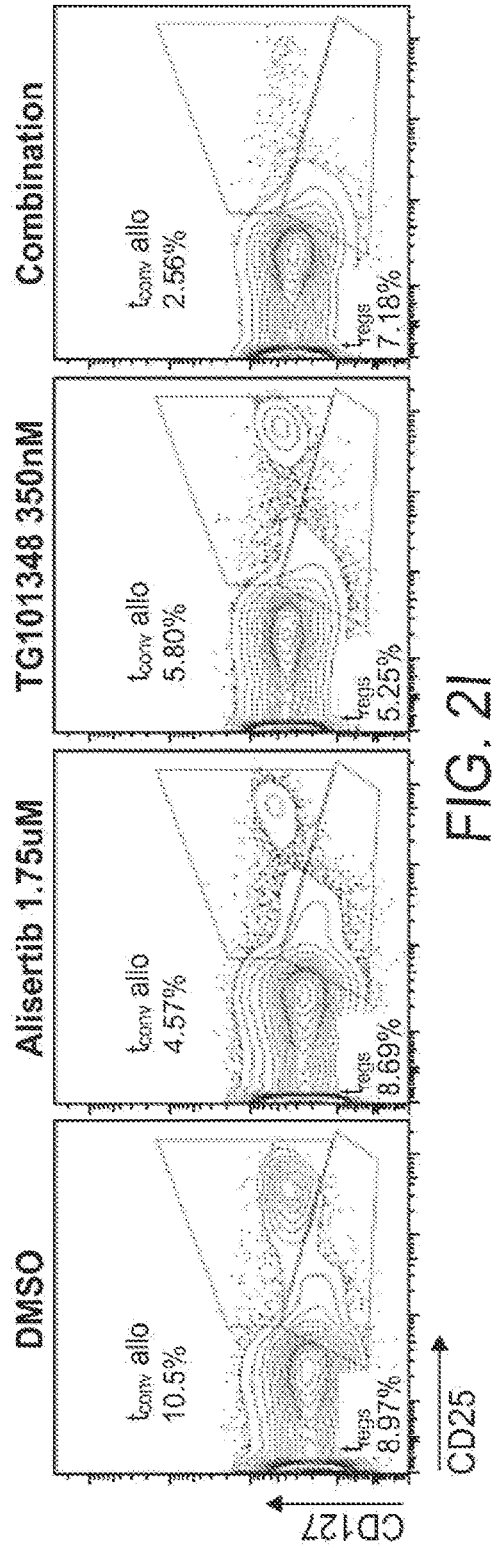

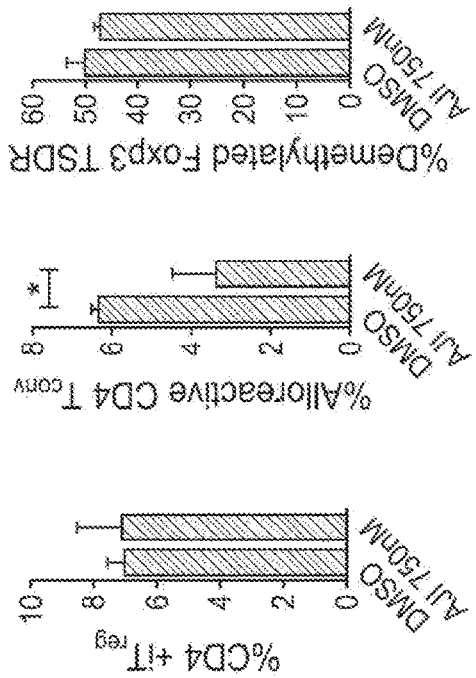
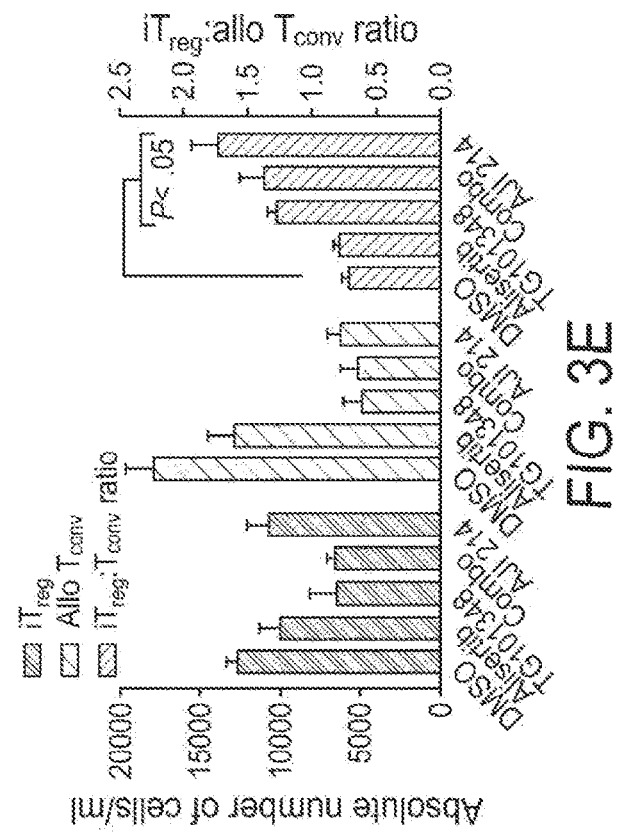
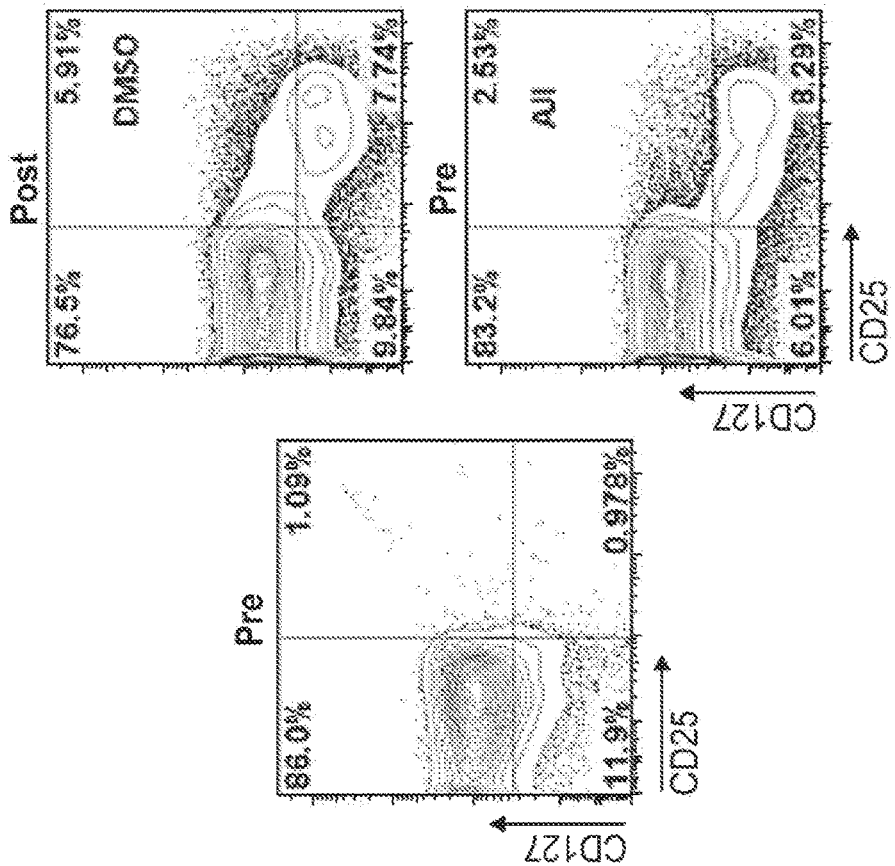
FIG. 3A, FIG. 3B, FIG. 3C, FIG. 3D, FIG. 3E

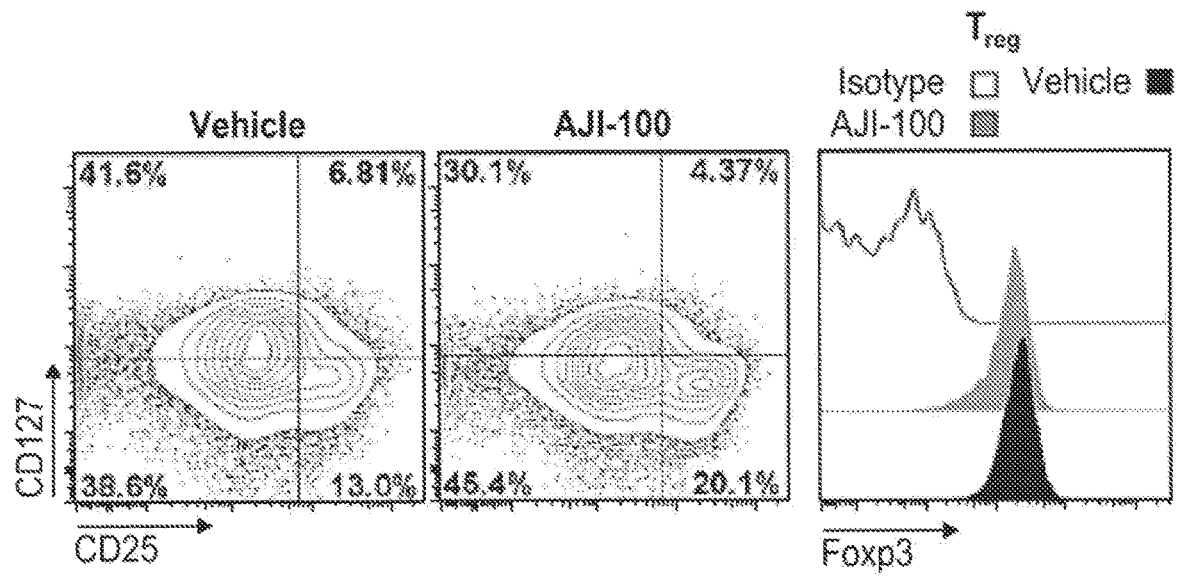
FIG. 8F    FIG. 8G
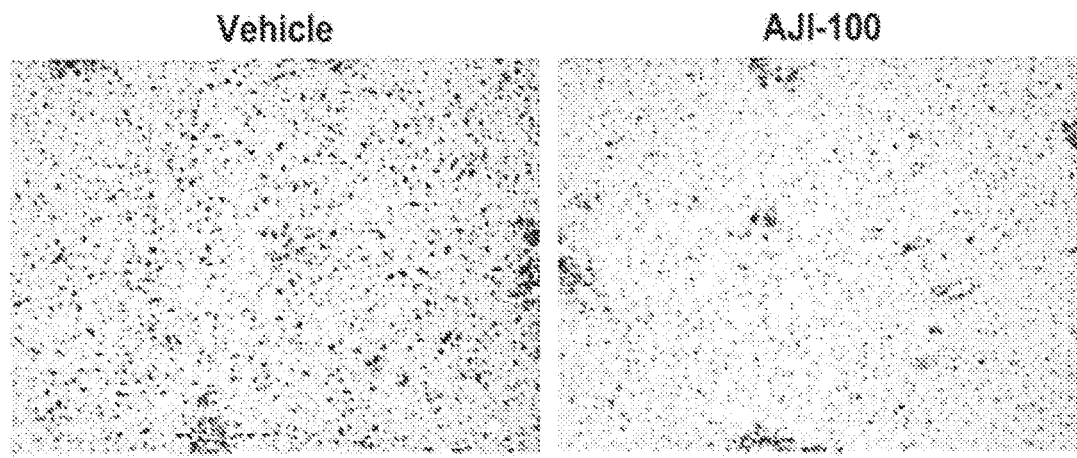
FIG. 8H    FIG. 8I
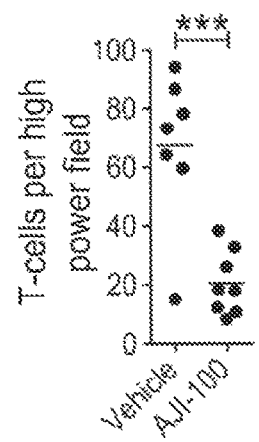 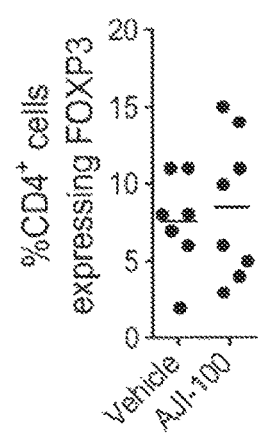
FIG. 8J    FIG. 8K

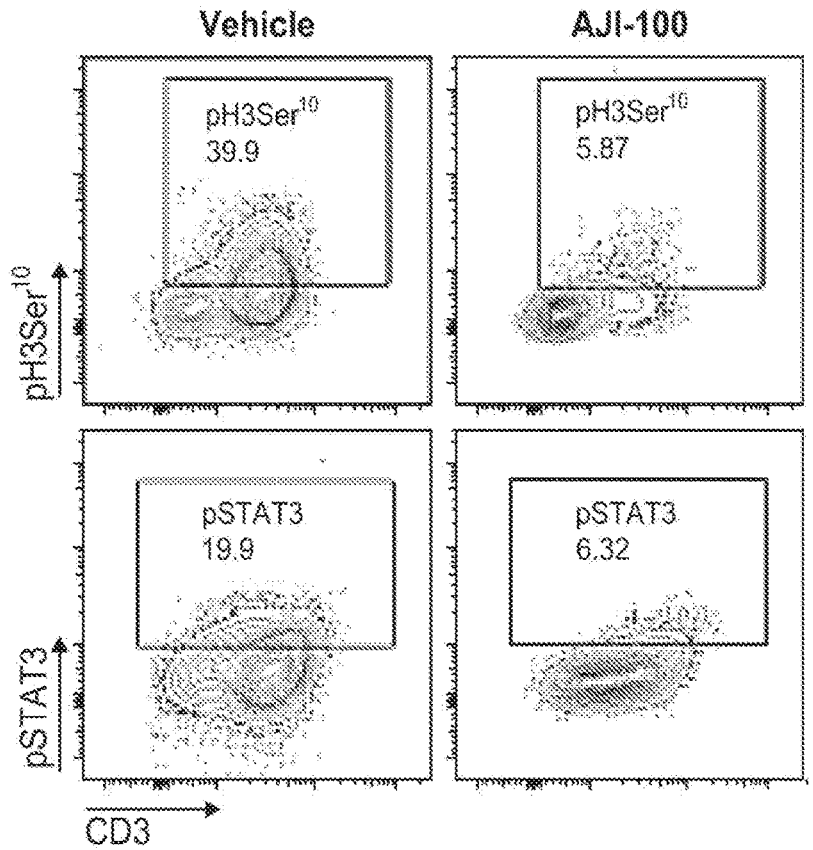
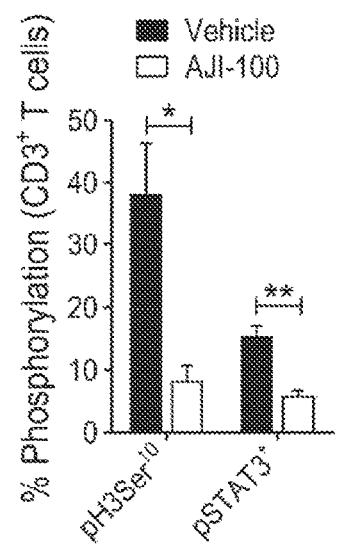
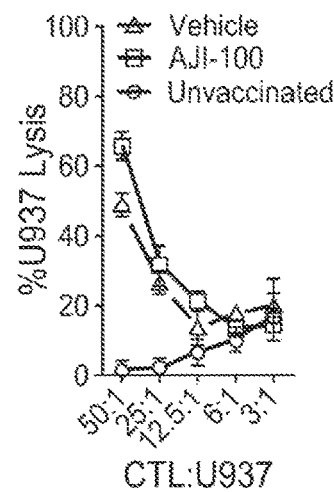
FIG. 13E
FIG. 13F
FIG. 13G
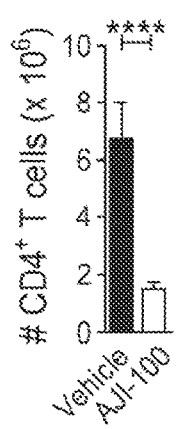
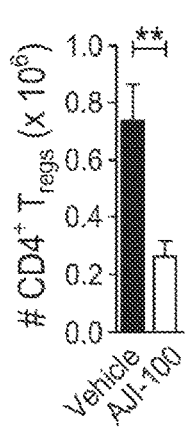
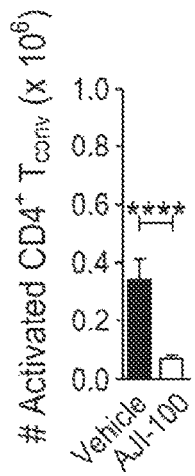
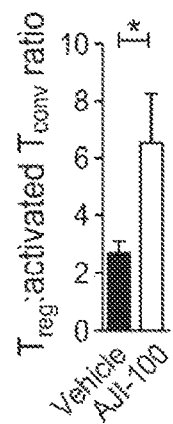
FIG. 14A    FIG. 14B    FIG. 14C    FIG. 14D

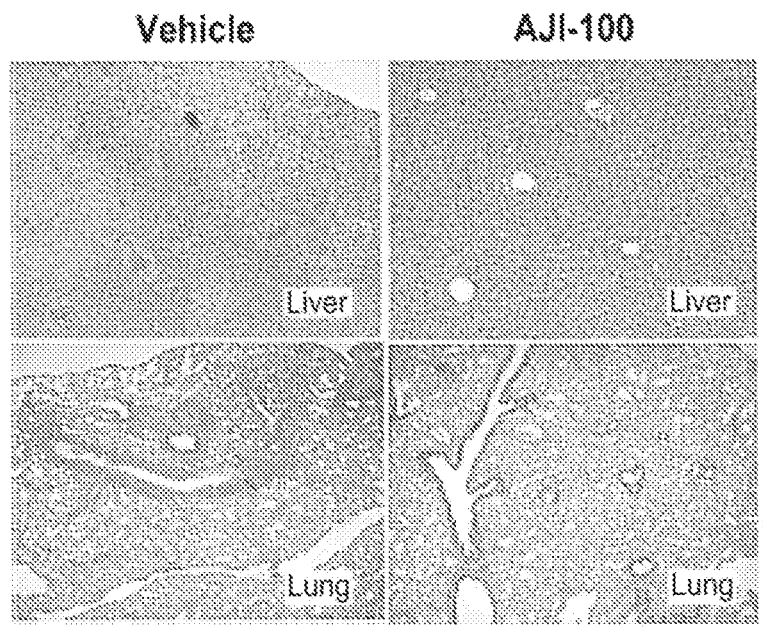
FIG. 14I
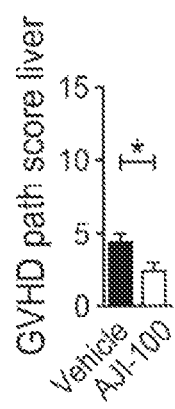 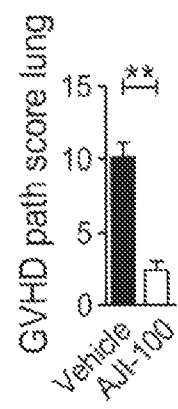 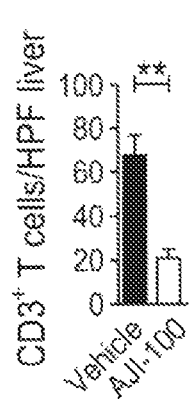 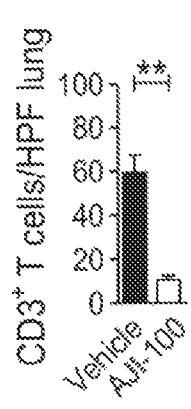
FIG. 14J  FIG. 14K  FIG. 14L  FIG. 14M

AURORA KINASE AND JANUS KINASE INHIBITORS FOR PREVENTION OF GRAFT VERSUS HOST DISEASE

CROSS REFERENCE TO RELATED APPLICATIONS

This application is a continuation of U.S. application Ser. No. 17/555,786, filed Dec. 20, 2021, which is a divisional of U.S. application Ser. No. 16/083,681, filed Sep. 10, 2018, which is a national stage entry of PCT/US2017/022074, filed Mar. 13, 2017, which claims the benefit of priority to U.S. Provisional Application 62/307,030, filed Mar. 11, 2016, each of which are incorporated by reference herein.

STATEMENT REGARDING FEDERALLY SPONSORED RESEARCH

This invention was made with Government Support under Grant No. K08 HL11654701A1 and Grant No. P30-CA076292 awarded by the National Institutes of Health. The Government has certain rights in the invention.

FIELD

The subject matter disclosed herein relates generally to graft versus host disease (GVHD). More specifically, the subject matter disclosed herein relates to inhibitors of Aurora kinase and JAK2 and their use in preventing or treating GVHD.

BACKGROUND

Graft-versus-host disease (GVHD) is a leading cause of non-relapse mortality after allogeneic hematopoietic cell transplantation (alloHCT). Broadly acting calcineurin inhibitors (CNI) are often used to prevent GVHD, but exert undesirable antagonistic effects on T-cell receptor signaling and regulatory T-cell ($T_{reg}$) differentiation and function (M. Vaeth et al., Selective NFAT targeting in T cells ameliorates GvHD while maintaining antitumor activity. *Proc. Natl. Acad. Sci. USA* 112, 1125 (2015); K. Singh et al., Superiority of rapamycin over tacrolimus in preserving nonhuman primate $T_{reg}$ half-life and phenotype after adoptive transfer. *Am. J. Transplant.*: 14, 2691 (2014); R. Zeiser et al., Inhibition of CD4$^+$CD25$^+$ regulatory T-cell function by calcineurinindependent interleukin-2 production. *Blood* 108, 390 (2006)). The lack of immune selectivity by CNIs places the alloHCT recipient at risk for opportunistic infections and relapse of their underlying hematologic malignancy. An alternative approach at GVHD prevention is to concurrently target CD28 costimulation and IL-6 receptor activation of T-cells by inhibiting key signal transduction molecules in these pathways.

CD28 costimulation contributes to T-cell alloreactivity and GVHD. GVHD in rodents is ameliorated by transplantation of CD28 negative compared to wild type T-cells (P. Tan et al., Induction of alloantigen-specific hyporesponsiveness in human T lymphocytes by blocking interaction of CD28 with its natural ligand B7/BB1. *J. Experi. Med.* 177, 165 (1993); X. Z. Yu et al., CD28-specific antibody prevents graft versus-host disease in mice. *J. Immunol.* 164, 4564 (2000)). Blockade of ligand interactions between CD80/CD86 and CD28 with neutralizing antibody also reduces murine GVHD. CD28 signal transduction activates mTOR and Aurora kinase in T-cells (J. Song et al., The kinases aurora B and mTOR regulate the G1-S cell cycle progression of T lymphocytes. *Nature Immunol.* 8, 64 (2007)). mTOR is a known pharmacologic target in GVHD prophylaxis (C. Cutler et al., Tacrolimus/sirolimus vs tacrolimus/methotrexate as GVHD prophylaxis after matched, related donor allogeneic HCT. *Blood* 124, 1372 (2014); J. Pidala et al., Prolonged sirolimus administration after allogeneic hematopoietic cell transplantation is associated with decreased risk for moderate-severe chronic graft vs. host disease. *Haematologica* (2015); J. Pidala et al., A randomized phase II study to evaluate tacrolimus in combination with sirolimus or methotrexate after allogeneic hematopoietic cell transplantation. *Haematologica* 97, 1882 (2012)), and its blockade is selectively toxic to $T_{conv}$ compared to $T_{reg}$ (R. Zeiser et al., Differential impact of mammalian target of rapamycin inhibition on CD4$^+$CD25$^+$Foxp3$^+$ regulatory T cells compared with conventional CD4$^+$ T cells. *Blood* 111, 453 (2008)). However, GVHD prevention with sirolimus, an mTOR inhibitor, is inadequate if not combined with a CNI (L. Johnston et al., Sirolimus and mycophenolate mofetil as GVHD prophylaxis in myeloablative, matched-related donor hematopoietic cell transplantation. *Bone Marrow Transplant.* 47, 581 (2012)). Aurora kinase isoforms ubiquitously regulate mitotic progression and cellular polarity in human cells (M. Carmena, W. C. Earnshaw, The cellular geography of aurora kinases. *Nature Rev. Mol. Cell Biol.* 4, 842 (2003); S. M. Lens et al., Shared and separate functions of polo-like kinases and aurora kinases in cancer. *Nature Rev. Cancer* 10, 825 (2010)), but also mediate T-cell costimulation. Aurora kinase is able to activate substrates required for T-cell proliferation that are shared with mTOR, and is only partially curtailed by sirolimus. Complete inhibition of Aurora activity requires direct blockade of the molecule or targeting upstream phosphatidylinositol-3-OH kinase (PI(3)K). Increased Aurora kinase A expression was recently correlated with acute GVHD in human recipients of alloHCT, as well as experimental models studying murine and nonhuman primate (NHP) hosts. Accordingly, treatment with sirolimus did not control Aurora activity in the transplanted NHPs. Moreover, pharmacologic blockade of this novel pathway with alisertib, an Aurora kinase A inhibitor, significantly delayed the onset of GVHD in mice. These data revealed that Aurora kinase A alone does not fully control alloreactivity (S. N. Furlan et al., Transcriptome analysis of GVHD reveals aurora kinase A as a targetable pathway for disease prevention. *Sci. Translational Med.* 7, 315ra191 (2015)).

IL-6 receptor signaling polarizes $T_H1$ and $T_H17$ cells that are effectors in GVHD, and impairs $T_{regs}$ that modulate GVHD (B. C. Betts et al., Janus kinase-2 inhibition induces durable tolerance to alloantigen by human dendritic cell-stimulated T cells yet preserves immunity to recall antigen. *Blood* 118, 5330 (2011); B. C. Betts, A. Veerapathran, J. Pidala, X. Z. Yu, C. Anasetti, STAT5 polarization promotes $iT_{regs}$ and suppresses human T-cell alloresponses while preserving CTL capacity. *J. Leukocyte Biol.* 95, 205 (2014); J. Choi et al., Pharmacologic blockade of JAK1/JAK2 reduces GvHD and preserves the graft-versus-leukemia effect. *PloS one* 9, e109799 (2014); A. Laurence et al., STAT3 transcription factor promotes instability of $nT_{reg}$ cells and limits generation of $iT_{reg}$ cells during acute murine graft-versus-host disease. *Immunity* 37, 209 (2012); R. Zeiser et al., Ruxolitinib in corticosteroid-refractory graft-versus-host disease after allogeneic stem cell transplantation: a multi-center survey. *Leukemia*, (2015)). IL-6 activates JAK2 and leads to downstream phosphorylation of STAT3 (B. C. Betts et al., Anti-IL6-receptor-alpha (tocilizumab) does not inhibit human monocyte-derived dendritic cell maturation or alloreactive T-cell responses. *Blood* 118, 5340 (2011)). It was observed that CD4+ T-cell JAK2 activity by IL-6 is increased among alloHCT recipients who later develop GVHD (B. C. Betts et al., CD4+ T cell STAT3 phosphorylation precedes acute GVHD, and subsequent $T_H17$ tissue invasion correlates with GVHD severity and therapeutic response. *J. Leukocyte Biol.*, (2015)). Anti-IL-6 receptor antibody combined with a CNI ameliorates human GVHD, but it does not influence $T_H1$, $T_H17$, or $T_{reg}$ differentiation (G. A. Kennedy et al., Addition of interleukin-6 inhibition with tocilizumab to standard graft-versus-host disease prophylaxis after allogeneic stem-cell transplantation: a phase 1/2 trial. The Lancet. Oncology 15, 1451 (2014)). JAK2 inhibition conversely polarizes natural $T_{reg}$ responses, and inhibits $T_H1$ and $T_H17$ development in vitro. However, selective blockade of JAK2 alone does not provide lasting protection in murine GVHD. This observation is distinct from JAK1/JAK2 inhibition, where co-blockade of JAK1 acts broadly to reduce GVHD (*Blood* 123, 3832 (2014)) as well as beneficial anti-viral CTL (S. Spoerl et al., Activity of therapeutic JAK 1/2 blockade in graft-versus-host disease. *Blood* 122, 3843 (2013); A. Heine, P. Brossart, D. Wolf, Ruxolitinib is a potent immunosuppressive compound: is it time for anti-infective prophylaxis? *Blood* 122, 1192 (2013)). These data show that JAK2 activation selective inhibition is insufficient to completely prevent GVHD despite favorable immune effects.

Thus there is a need for new compositions and methods for treating GVHD. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to reducing the risk of, preventing, or treating graft versus host disease (GVHD) in a subject. More specifically, the subject matter disclosed herein relates to inhibitors of Aurora kinase A and JAK2. In more specific examples, the disclosed subject matter relates to concurrent inhibition of Aurora kinase A and JAK2 and their use in reducing the risk of, preventing, or treating GVHD. GVHD can be attributed to a solid organ transplant, tissue graft, or a cellular transplant.

The methods described herein can include administering to a subject at risk of developing or having GVHD, a composition comprising a compound of the following formula

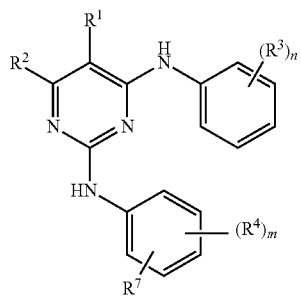

I wherein

R$^1$ is selected from the group consisting of H, Cl, F, Br, I, CN, NO$_2$, NH$_2$, CF$_3$, CO$_2$H, CO$_2$NH$_2$, CO$_2$NHR$^5$, CO$_2$R$^5$, C(O)R$^5$, C(O)NH$_2$, C(O)NHR$^5$, and C$_1$-C$_6$ alkyl optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

R$^2$ is selected from the group consisting of H, OH, CN, NO$_2$, NH$_2$, optionally substituted C$_1$-C$_6$ alkyl, optionally substituted cycloalkyl, optionally substituted aryl, and optionally substituted heteroaryl, wherein optionally substituted substituents are optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

or R$^1$ and R$^2$ together form a fused cycloalkyl, cycloheteroalkyl, aryl, or heteroaryl group;

each R$^3$ is selected, independently, from the group consisting of SO$_2$NH$_2$, SO$_2$NHR$^5$, NHSO$_2$R$^5$, NHCO$_2$R$^5$, NHC(O)R$^5$, NHCONHR$^5$, F, Cl, Br, I, NO$_2$, optionally substituted C$_1$-C$_6$ alkyl, optionally substituted C$_1$-C$_6$ alkoxy, optionally substituted cycloheteroaryl, and optionally substituted fused cycloheteroalkyl, wherein optionally substituted substituents are optionally substituted with sulfonyl;

each R$^4$ is selected, independently, from the group consisting of F, Cl, Br, I, NO$_2$, optionally substituted C$_1$-C$_6$ alkyl, optionally substituted C$_1$-C$_6$ alkoxy, COOH, C(O)NH$_2$, C(O)R$^5$, C(O)NHR$^5$, CH$_2$C(O)R$^5$, SO$_2$NH$_2$, SO$_2$NHR$^5$, CONHSO$_2$R$^5$, optionally substituted phenyl, optionally substituted OPhenyl, tetrazole, piperadinyl, piperazinyl, and morpholinyl, wherein optionally substituted substituents are optionally substituted with alkoxy, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

each R$^5$ is selected, independently, from optionally substituted C$_1$-C$_6$ alkyl, optionally substituted C$_1$-C$_6$ cycloalkyl, optionally substituted aryl, optionally substituted heteroaryl, optionally substituted heterocycloalkyl, and optionally substituted heteroalkyl, wherein optionally substituted substituents are optionally substituted with C$_1$-C$_6$ alkyl, C$_1$-C$_6$ alkoxyl, cycloalkyl, cycloheteroalkyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

R$^7$ is selected from the group consisting of H, C$_1$-C$_6$ alkyl, C$_1$-C$_6$ alkoxyl, halide, hydroxyl, cyano, nitro, and amino;

n is 0-5; and m is 1-5, or a pharmaceutically acceptable salt thereof.

In certain aspects, the composition can include a compound of the following formula:

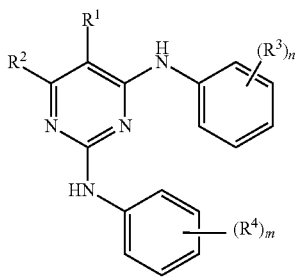

wherein
R¹ is selected from the group consisting of H, Cl, F, Br, I, $C_1$-$C_6$ alkyl, CN, $NO_2$, and $NH_2$;
R² is selected from the group consisting of H, F, and Cl;
each R³ is selected, independently, from the group consisting of Cl, Br, F, COOH, $CF_3$, CN, phenyl, $OCH_3$, $COR^5$, $CONH_2$, $CONR^5$, and $COONH_2$; and
each R⁴ is selected, independently, from the group consisting of H, COOH, $CONH_2$, $CONR^5$, $SO_2NH_2$, $CONSO_2R^5$, tetrazole, 4-morpholine, and $COR^5$;
each R⁵ is selected, independently, from the group consisting of optionally substituted $C_1$-$C_6$ alkyl, optionally substituted cycloalkyl, optionally substituted heteroaryl, and optionally substituted heteroalkyl, wherein optionally substituted substituents are optionally substituted with $C_1$-$C_6$ alkyl, $C_1$-$C_6$ alkoxyl, cycloalkyl, cycloheteroalkyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;
n is 0-5; and
m is 1-5,
or a pharmaceutically acceptable salt thereof.

In certain aspects, the composition can include a compound having one of the following formulas:

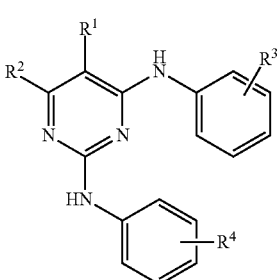

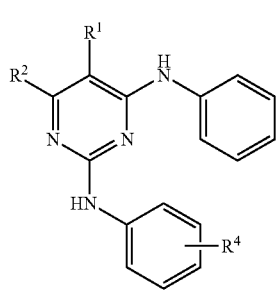

wherein
R¹ is selected from the group consisting of H, Cl, F, Br, I, $CH_3$ and $NH_2$;
R² is selected from the group consisting of H, F, and Cl;
R³ is selected from the group consisting of 2-Cl, 2-Br, 2-F, 2-COOH, 2-$CF_3$, 2—CN, 2-phenyl, 2-$OCH_3$, 2-$COONH_2$, 4—COOH, and 4-$OCH_3$; and
R⁴ is selected from the group consisting of H, COOH, 2-$CONH_2$, 4—$CONH_2$, $SO_2NH_2$, tetrazole, and 4-morpholine.

In certain examples of Formulas I, II, and IIIA, R³ is 2-Cl, and n is 1. In some examples, R⁴ is 4-COOH, and m is 1. In other examples, R⁴ is 4-$CONH_2$, and m is 1. In some examples, R³ is 2-Cl, n is 1, m is 1, and R⁴ is COOH, $COR^5$, $CONH_2$, $CONR^5$, or $CONSO_2R^5$, wherein R⁵ is $C_1$-$C_6$ alkyl, cycloalkyl, heteroaryl, or heteroalkyl. In other examples, R³ is H, m is 1, and R⁴ is COOH, $COR^5$, $CONH_2$, $CONR^5$, or $CONSO_2R^5$, wherein R⁵ is $C_1$-$C_6$ alkyl, cycloalkyl, heteroaryl, or heteroalkyl. In a preferred example, R¹ is Cl, R² is H, R³ is H, m is 1, and R⁴ is 4-$CONH_2$. In other examples n is 0.

The compositions described herein can be administered at a dose of about 0.1 mg/kg to about 100 mg/kg.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIGS. 1A-1E show synergistic immune suppression with combined inhibition of Aurora kinase A and JAK2. In FIG. 1A, T-cells were stimulated with DCs (DC:T-cell ratio 1:30) exposed to either TG101348 (JAK2 inhibitor), alisertib (Aurora kinase A inhibitor), or both at a fixed ratio of 1:5 respectively at varying concentrations once on day 0. Proliferation was determined by fluorescence assay on day 5, with % proliferation based on DMSO control. Graph depicts combination synergy ($IC_{50}$=TG101348 350 nM and alisertib 1.75 µM), showing 1 representative independent experiment of 2 performed in triplicate. Combination index (CI) calculated per Chou and Talalay method. In FIG. 1B, AlloMLR (DC:T-cell ratio 1:30) was treated with bisanilinopyrimidine (I) (dual JAK2/Aurora kinase A inhibitor) or DMSO once on day 0. Proliferation was determined by colorimetric assay on day 5, with % proliferation based on DMSO control. $IC_{50}$=100 nM. Graph shows average triplicate means±SEM from 3 independent experiments (ANOVA). In FIGS. 1C-1D, bar graphs depict mean gated $CD3^+$ Tcell STAT5 (target of JAK2) or H3 Ser10 (target of Aurora) phosphorylation±SD following 5-day allogeneic DC stimulation treated with bisanilinopyrimidine (I) or DMSO from 3 independent experiments (unpaired t-test). Representative contour plots are shown with phosphorylation based on isotype control. In FIG. 1E, a bar graph shows mean T-cell viability±SD by LIVE/DEAD Yellow exclusion from 4 independent experiments (unpaired t-test). *P<0.05.

FIGS. 2A-2I show concurrent blockade of Aurora kinase A and JAK2 selectively suppresses alloreactive $T_{conv}$, while sparing responder $T_{regs}$ T-cells were stimulated with DCs (DC:Tcell ratio 1:30) and treated with bisanilinopyrimidine (I) or DMSO once on day 0. In FIGS. 2A-2D, bar graphs show percent means of CD4$^+$ alloreactive T$_{conv}$ (CD25$^+$, CD127$^+$), CD4$^+$ T$_{reg}$ (CD25$^+$, CD127$^-$), and T$_{reg}$:allo T$_{conv}$ ratio±SD from 5 independent experiments on day 5 of culture (unpaired t-test). Representative contour plots show CD4$^+$ alloreactive T$_{conv}$ (CD25$^+$, CD127$^+$) and CD4$^+$ T$_{reg}$ (CD25$^+$, CD127$^-$) populations exposed to bisanilinopyrimidine (I) or DMSO after 5 days of DCallostimulation. In FIG. 2E, box plots depict mean T$_{reg}$ versus T$_{conv}$ proliferation by Cell Trace Violet dilution±SD among identically treated alloMLRs exposed to bisanilinopyrimidine (I) or DMSO from 3 independent experiments (unpaired t-test). FIG. 2F is a representative histogram that shows proliferation in each T-cell compartment with respect to bisanilinopyrimidine (I) or DMSO treatment. In FIG. 2G, a bar graph shows mean gated CD4$^+$ T-cell STAT5 phosphorylation±SD following brief IL-2 stimulation treated with bisanilinopyrimidine (I) or DMSO from 3 independent experiments (ANOVA). In FIG. 2H, a histogram depicts intracellular Foxp3 expression among CD4$^+$, CD25$^+$, CD127$^-$ T$_{regs}$ following 5-day DCallostimulation exposed to bisanilinopyrimidine (I) or DMSO. Data representative of 5 experiments. In FIG. 2I, AlloMLRs (DC:T-cell ratio 1:30) were treated with alisertib (Aurora kinase A inhibitor), TG101348 (JAK2 inhibitor), a combination of both, or DMSO once on day 0. Representative contour plots show CD4$^+$ alloreactive T$_{conv}$ (CD25$^+$, CD127$^+$) and CD4$^+$ T$_{reg}$ (CD25$^+$, CD127$^-$) populations exposed to either inhibitor, the combination, or DMSO after 5 days of DCallostimulation. Data are from one representative experiment of 2. NS=not significant, *P<0.05, **P=0.001-0.01.

FIGS. 3A-3E show dual blockade of Aurora kinase A and JAK2 selectively increases the ratio of iT$_{reg}$ to alloreactive T$_{conv}$. In FIG. 3A, a representative contour plots show T$_{reg}$ (CD25$^+$, CD127$^-$) depletion of naïve CD4$^+$ T-cell responders at outset of alloMLR (DC:T-cell ration 1:30), followed by induction of iT$_{reg}$ versus allo T$_{conv}$ (CD25$^+$, CD127$^+$) after 5 days of culture exposed to AJI-214 or DMSO. In FIGS. 3B-3C, bar graphs show mean frequency of CD4$^+$ iT$_{reg}$ and allo T$_{conv}$ in 5-day allogeneic co-cultures treated with bisanilinopyrimidine (I) or DMSO±SD from 4 independent experiments (unpaired t-test). In FIG. 3D, a bar graph depicts triplicate mean % demethylation of Foxp3$^+$ ±SEM among iT$_{regs}$ in alloMLRs treated with bisanilinopyrimidine (I) or DMSO from 4 independent experiments (unpaired t-test). In FIG. 3E, bar graphs show replicate means of absolute numbers of iT$_{reg}$, allo T$_{conv}$, and the ratio of iT$_{reg}$:allo T$_{conv}$±SD from 5-day MLRs treated with Alisertib 1.75 µM, TG101348 350 nM, a combination of both, bisanilinopyrimidine (I) 750 nM, or DMSO control (ANOVA). Data are from one representative experiment of 2 performed in triplicate.

In FIG. 4A, the suppressive capacity of sorted, DC-allostimulated iT$_{regs}$ previously exposed to bisanilinopyrimidine (I) or DMSO was tested at different ratios of iT$_{reg}$ to self T-cell responders stimulated by original allogeneic DCs (DC:responder T-cell ratio 1:30) in fresh alloMLRs. No additional bisanilinopyrimidine (I) or DMSO was added. The bar graph shows triplicate means of % proliferation±SEM based on 3H-thymidine incorporation on day 6 from 3 independent experiments (ANOVA). In FIG. 4B, the potency of iT$_{regs}$ generated in the presence of alisertib (Aurora kinase A inhibitor), TG101348 (JAK2 inhibitor), a combination of both, or DMSO was tested in standard suppression assays. No additional small molecule inhibitors or DMSO was added. The bar graph shows triplicate means of % proliferation±SD based on 3H-thymidine incorporation on day 6 (unpaired t-test). Data are from one representative experiment of 2 performed in triplicate.

In FIG. 5A, contour plots show the CD4$^+$ iT$_{reg}$ and non-T$_{reg}$ gating strategy after 5-day alloMLR treated with bisanilinopyrimidine (I) (750 nM) or DMSO. In FIGS. 5B-5D, CD39 expression (% and geometric MFI) was increased by among iT$_{reg}$ generated in the presence of bisanilinopyrimidine (I) (750 nM). The bar graphs show mean data±SD from 3 independent experiments (unpaired t-test). In FIG. 5E, bar graphs show replicate means of ATP consumption±SD after stimulating 75,000 iT$_{reg}$ with 50 µM of ATP for 45 minutes. ATP measured by luminescence assay. Data are from one representative experiment of 2 performed in triplicate (unpaired t-test). In FIG. 5F, AlloMLRs of naïve, T$_{reg}$-depleted CD4$^+$ T-cells, and allogeneic DCs (DC:T-cell ratio 1:30) were treated with either bisanilinopyrimidine (I), ARL67156 (CD39 inhibitor), both, or DMSO. Proliferation was determined by colorimetric assay on day 5, with % proliferation based on DMSO control. Graph shows average triplicate means±SEM from 5 independent experiments (unpaired t-test). In FIGS. 5G-5H, bar graphs depict mean fold MFI of LAGS and CTLA4±SD on iT$_{regs}$ harvested from alloMLRs treated with bisanilinopyrimidine (I) or DMSO from 3 independent experiments (unpaired t-test). In FIGS. 5I-5J, bar graphs show triplicate mean concentrations of IL-10 and TGF-beta±SEM among PMA/ionomycin-stimulated iT$_{regs}$ previously exposed to bisanilinopyrimidine (I) or DMSO during co-culture from 4 independent experiments (unpaired t-test). *P<0.05, P=0.001-0.01, **P<0.0001.

In FIG. 7A, AlloMLR (DC:T-cell ratio 1:30) was treated with bisanilinopyrimidine (II) (dual Aurora kinase A/JAK2 inhibitor) or DMSO once on day 0. Proliferation was determined by colorimetric assay on day 5 (ANOVA). IC$_{50}$=200 nM. Graph shows triplicate means±SD from 1 representative experiment of 2. In FIG. 7B, a representative histogram shows bisanilinopyrimidine (II) inhibits CD3$^+$ T-cell STAT5 phosphorylation in vitro. Data are from one representative experiment of 2. NSG mice received human PBMCs (30×10$^6$ cells), with bisanilinopyrimidine (II) (50 mg/kg daily) or vehicle administered from day 0 to day +14. In FIG. 7C, a representative histogram shows H3 ser10 phosphorylation in human CD3$^+$ T-cells harvested at day +14 among each group. In FIGS. 7D-7F, graphs show mean % weight change±SEM, GVHD scores±SEM (unpaired t-test), and survival of pooled data from 2 independent experiments (long-rank test). n=8 mice per each group. In FIG. 7G, a graph depicts mean specific lysis±SD by human CTL generated in vivo using NSG mice transplanted with human PBMCs and irradiated U937 cells (10$^7$) on days 0 and +7. Results shown are from 1 of 2 independent experiments, using a total of 7 mice per arm. In FIG. 7H, a graph shows mean specific lysis±SD of CD8+ CTL generated in vitro while exposed to bisanilinopyrimidine (I) or DMSO for 10 days. Results shown are from 1 of 2 independent experiments. U937 lysis was measured by released fluorescence after 4 hours. P=0.001-0.01, *P=0.0001-0.001.

FIGS. 8A-8K show targeting Aurora kinase A and JAK2 increases the proportion of $T_{reg}$ to allo $T_{conv}$ in vivo, and reduces T-cell homing to recipient livers. Xenotransplanted NSG mice were treated with bisanilinopyrimidine (II) (50 mg/kg daily) or vehicle daily starting at day 0, then euthanized on day +14. Recipient spleens and livers were harvested, and tissue-resident T-cells were evaluated. Dot plots show absolute number of total spleen cells (FIG. 8A), human CD3+ T-cells (FIG. 8B), % CD4+, CD25+, CD127−, Foxp3+ $T_{reg}$ (FIG. 8C), % CD4+, CD25+, CD127+ allo $T_{conv}$ (FIG. 8D), and the ratio of $T_{reg}$ to allo $T_{conv}$ (FIG. 8E) (unpaired t-test). In FIG. 8F, representative contour plots show the % CD4+ $T_{reg}$ and % CD4+ alloreactive $T_{conv}$ residing in spleens of bisanilinopyrimidine (II)- or vehicle-treated mice at day +14. FIG. 8G, the representative histograms show corresponding expression of Foxp3 within the CD4+ $T_{regs}$. In FIGS. 8H-8I, sections of recipient livers show bisanilinopyrimidine (II) significantly reduces the amount of tissue-resident human T-cells, compared to vehicle control (red=CD3). Dot plots show the number of human T-cells per high power field (FIG. 8J) and % CD4+ cell expressing Foxp3 (FIG. 8K) in the livers at day +14 (unpaired t-test). Pooled data from 2 independent experiments. n=7-8 mice per each group. NS=not significant, *P<0.05, ***P=0.0001-0.001.

In FIG. 9A, Human T cells were stimulated with DCs (DC/T cell ratio of 1:30) exposed to TG101348 (JAK2 inhibitor), alisertib (Aurora kinase A inhibitor), or both TG101348 and alisertib at a fixed ratio of 1:5, respectively, at varying concentrations once on day 0. Proliferation was determined by fluorescence assay on day 5, with % proliferation based on dimethyl sulfoxide (DMSO) control. Graph depicts combination synergy ($IC_{50}$ values for TG101348 and alisertib were 350 nM and 1.75 mM, respectively), showing one representative independent experiment of two performed with triplicate technical replicates. The CI was calculated using the Chou-Talalay method. AlloMLR (DC/T cell ratio of 1:30) treated with AJI-214 (FIG. 9B), AJI-100 (FIG. 9C) (dual JAK2/Aurora kinase A inhibitors), or DMSO once on day 0 is shown. $IC_{50}$ values for AJI-214 and AJI-100 were 100 and 200 nM, respectively. Graph shows average triplicate means±SEM from two to three independent experiments [analysis of variance (ANOVA)]. In FIG. 9D, a bar graph depicts T cell proliferation when exposed to alisertib (1.75 mM), TG101348 (350 nM), a combination of alisertib and TG101348 (combo), AJI-214 (750 nM), or AJI-100 (750 nM) in alloMLRs. Means±SEM from four independent experiments (ANOVA) are shown using triplicate technical replicates. In FIGS. 9E-9H, bar graphs depict the mean gated CD3+ T cell H3Ser10 (target of Aurora) or STAT3 (target of JAK2) phosphorylation±SD from three independent experiments after stimulation with allogeneic DCs (5 days) or IL-6 (15 min), respectively (ANOVA). Representative contour plots show H3Ser10 and STAT3 phosphorylation, respectively.

In FIG. 10A-10B, T cells were stimulated with allogeneic DCs (DC/T cell ratio of 1:30) and treated with kinase inhibitors or DMSO once on day 0. Bar graphs show replicate mean absolute numbers of activated CD4+, CD25+, CD127+ or activated CD8+, CD25+ $T_{conv}$±SEM at day +5 from six independent experiments (ANOVA and paired t test). In FIG. 10C, a bar graph shows the mean number of IL-17 spots per well±SD from triplicate technical replicates among DC-allostimulated CD4+ T cells. One of three representative experiments is shown. In FIG. 10D, a bar graph shows mean % CD4+, IFN-γ+ T cells±SEM at day +5 of alloMLR from five independent experiments with technical replicates performed in triplicate. In FIGS. 10E-10F, representative contour plots show $T_{reg}$ (CD25+ and CD127−) depletion of CD4+ T cell responders at outset of alloMLR (DC/T cell ratio of 1:30), followed by induction of $iT_{reg}$ (CD127−, CD25+, and Foxp3+) after 5 days of culture exposed to kinase inhibitors or DMSO. In FIG. 10G, a bar graph shows mean absolute numbers of $iT_{regs}$±SEM from seven independent experiments performed with two to three technical replicates (ANOVA and paired t test). In FIG. 10H, a representative histograms depict pSTAT5 expression among IL-2-stimulated CD3+ T cells while exposed to kinase inhibitors or DMSO. Geometric mean fluoresce nce intensity (MFI) of pSTAT5 is shown along the right margin. One of three representative experiments is shown. *P<0.05, **P=0.001 to 0.01. Alisertib (1.75 mM), TG101348 (350 nM), AJI-214 (750 nM), and AJI-100 (750 nM).

In FIG. 11A, a Bar graph depicts mean % demethylation of Foxp3+±SEM among $iT_{regs}$ in alloMLRs treated with AJI-214 (750 nM) or DMSO from four independent experiments using triplicate technical replicates. In FIG. 11B, the suppressive capacity of sorted, DC-allostimulated $iT_{regs}$ previously exposed to AJI-214 or DMSO was tested at different ratios of $iT_{reg}$ to T cell responders stimulated by fresh allogeneic DCs (DC/responder T cell ratio of 1:30) in alloMLRs. No additional AJI-214 or DMSO was added. Bar graph shows means of % proliferation±SEM based on [3H]thymidine incorporation on day 6 from three independent experiments with triplicate technical replicates (ANOVA). In FIG. 11C, the potency of $iT_{regs}$ generated in the presence of alisertib (1.75 mM), TG101348 (350 nM), a combination of alisertib and TG101348, or DMSO was tested in standard suppression assays. No additional small-molecule inhibitors or DMSO was added. Bar graph shows means of % proliferation±SD based on [3H]thymidine incorporation on day 6 (paired t test). Data are from one representative experiment of two performed using triplicate technical replicates. *P<0.05.

In FIG. 12A, contour plots show the CD4+ $iT_{reg}$ and non-$T_{reg}$ gating strategy after 5-day alloMLR treated with AJI-214 (750 nM) or DMSO. In FIGS. 12B-12D, CD39 density [geometric MFI (gMFI)] is increased by among $iT_{reg}$ generated in the presence of AJI-214 (750 nM). Bar graphs show mean data±SD from three independent experiments (paired t test). In FIG. 12E, bar graphs show replicate means of ATP consumption±SD after stimulating 75,000 $iT_{regs}$ with 50 mM ATP for 45 min. ATP was measured by luminescence assay. Data are from one representative experiment of two performed using triplicate technical replicates (paired t test). In FIG. 12F, AlloMLRs of naïve, $T_{reg}$-depleted CD4+ T cells and allogeneic DCs (DC/T cell ratio of 1:30) were treated with AJI-214, ARL67156 (CD39 inhibitor), both AJI-214 and ARL67156, or DMSO. Proliferation was determined by colorimetric assay on day 5, with % proliferation based on DMSO control. Graph shows means±SEM from five independent experiments using three technical replicates (paired t test). In FIGS. 12G-12H, bar graphs depict mean fold MFI of LAGS and CTLA4±SD on iT$_{regs}$ harvested from alloMLRs treated with AJI-214 or DMSO from three independent experiments. In FIG. 12I-12J, bar graphs show mean concentrations of IL-10 and TGF-β±SEM among PMA (phorbol 12-myristate 13-acetate)/ionomycin-stimulated iT$_{regs}$ previously exposed to AJI-214 or DMSO during coculture from four independent experiments using three technical replicates. *P<0.05, P=0.001 to 0.01, **P<0.0001.

FIGS. 13A-13G show Blockade of Aurora kinase A and JAK2 reduces xenogeneic GVHD and preserves the in vivo generation of potent antitumor CTL. NSG mice received human PBMCs (30×10$^6$ cells) by intraperitoneal injection, with alisertib (30 mg/kg daily), TG101348 (45 mg/kg twice a day), a combination of alisertib and TG101348, or vehicle administered by oral gavage from day 0 to day +14. In FIG. 13A, percent survival is shown among the four groups (log-rank test). In FIG. 13B, a graph shows mean GVHD clinical scores±SEM for each group of mice (P=0.02 at day +30, vehicle versus combo, Mann-Whitney). Pooled data are from two independent experiments. n=7 to 8 mice per group. NSG mice were transplanted with human PBMCs as described, with AJI-100 (50 mg/kg daily) or vehicle administered ip from day 0 to day +14. In FIGS. 13C-13D, percent survival (log-rank test) and mean GVHD clinical scores±SEM (Mann-Whitney) are demonstrated. Pooled data are from two independent experiments. n=8 mice per group. In FIG. 13E, representative contour plots show expression of H3Ser$^{10}$ and STAT5 phosphorylation among human CD3$^+$ T cells harvested from recipient spleens at day +14. In FIG. 13F, a bar graph shows the mean % pH3Ser$^{10+}$ and % pSTAT3$^+$ T cells±SEM among AJI-100-treated and vehicle-treated mice at day +14 (n=6 mice per group, two independent experiments, Mann-Whitney). In FIG. 13G, a graph depicts mean specific lysis±SD by human CD8$^+$ CTL generated in vivo using NSG mice transplanted with human PBMCs and vaccinated with irradiated U937 cells (1×10$^7$) on days 0 and +7. Results shown are from one of two independent experiments, using a total of seven mice per group. U937 lysis was measured by released fluorescence after 4 hours (vehicle versus AJI-100, not significant, Mann-Whitney). *P<0.05, P=0.001 to 0.01, *P=0.0001 to 0.001, ****P<0.0001.

FIGS. 14A-14M show targeting Aurora kinase A and JAK2 increases the proportion of T$_{reg}$ to activated T$_{conv}$ and reduces T$_H$17 and T$_H$1 cells in xenotransplanted recipient mice. In FIGS. 14A-14D, xenotransplanted NSG mice were treated with AJI-100 (50 mg/kg) or vehicle daily starting at day 0 and then euthanized on day +14. Recipient spleens, livers, and lungs were harvested, and tissue-resident T cells were evaluated. Bar graphs show replicate mean absolute number of human CD4$^+$ T cells (FIG. 14A), CD4$^+$ T$_{regs}$ (FIG. 14B), CD4$^+$ activated T$_{conv}$ (CD25$^+$ and CD127$^+$) (FIG. 14C), and the ratio of T$_{reg}$ to activated T$_{conv}$ (FIG. 14D)±SEM (Mann-Whitney). In FIG. 14E, representative contour plots show the % CD4$^+$ T$_{reg}$ and % CD4$^+$ activated allo-T$_{conv}$ residing in spleens of AJI-100-treated or vehicle-treated mice at day +14. The representative histograms show corresponding expression of Foxp3 within the CD4$^+$ T$_{regs}$ In FIG. 14F, a bar graph shows the replicate mean number of IL-17 spots per well±SEM among human lymphocytes harvested from recipient spleens at day +14 (Mann-Whitney). In FIG. 14G-14H, Bar graph and representative contour plots depict the amount of CD4$^+$, IFN-γ$^+$ T cells±SEM from AJI-100 or vehicle-treated mice at day +14 (Mann-Whitney). In FIG. 14I, sections of recipient livers (top) and lung (bottom) show that AJI-100 significantly reduces GVHD damage in recipient target organs, compared to vehicle control. In FIG. 14J-14K bar graphs depict the mean GVHD pathology scores±SEM for host liver and lung at day +14. In FIG. 14L-14M, bar graphs shows that the mean number of human CD3$^+$ T cells±SEM [per high-power field (HPF)] infiltrating liver or lung at day +14 is significantly reduced by AJI-100 compared to vehicle (Mann-Whitney). Pooled data are from at least two independent experiments. n=6 to 14 mice per group. *P<0.05, P=0.001 to 0.01, **P<0.0001.

DETAILED DESCRIPTION

Figure 1A:
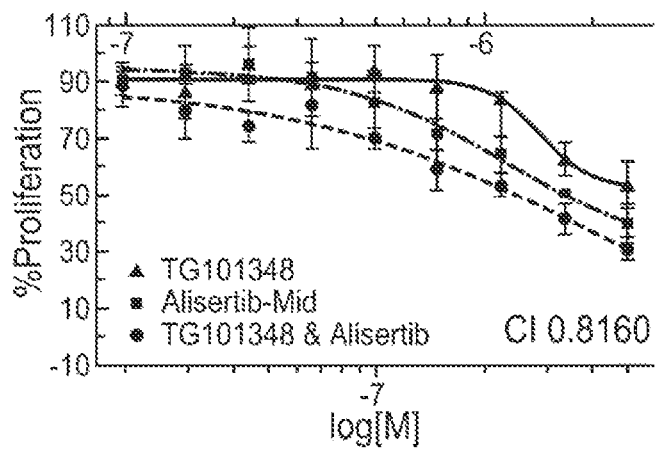

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., the risk of having GVHD). It is understood that this is typically in relation to some standard or expected value, in other words it is relative, but that it is not always necessary for the standard or relative value to be referred to.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as GVHD), diminishment of extent of GVHD, stabilized (i.e., not worsening) state of GVHD, preventing or delaying occurrence or recurrence of GVHD, delay or slowing of GVHD progression, and amelioration of the GVHD state.

The term "patient" preferably refers to a human in need of treatment for any purpose, and more preferably a human in need of such a treatment to treat GVHD. However, the term "patient" can also refer to non-human animals, preferably mammals such as dogs, cats, horses, cows, pigs, sheep and non-human primates, among others, that are in need of treatment.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)$A^1$ or —C(O)O$A^1$, where A' can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "oxo" as used herein is represented by =O.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" is used herein to refer to the sulfo-oxo group represented by the formula —$OS(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases.

Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In some embodiments, an effective amount is an amount sufficient to delay development. In some embodiments, an effective amount is an amount sufficient to prevent or delay occurrence and/or recurrence. An effective amount can be administered in one or more doses.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

Disclosed are compounds that are Aurora kinase inhibitors, e.g., Aurora A, B, and/or C kinase inhibitors and Janus kinase 2 (JAK2) inhibitors. The compounds can concurrently block Aurora kinase A and JAK2 signal. These disclosed compounds can be used in various compositions to reduce the risk of developing, prevent, or treat GVHD in a subject. These disclosed compounds can be used in various compositions to synergistically suppress alloreactive human T-cells in vitro, prevents xenogeneic graft-versus-host disease (GVHD) without impairing anti-tumor responses, and promotes the development and suppressive potency of $CD39^+$ inducible $T_{reg}$.

In certain embodiments, the disclosed compounds have the chemical structure shown in Formula I.

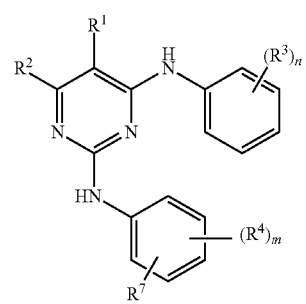

wherein $R^1$ is selected from the group consisting of H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

$R^2$ is selected from the group consisting of H, OH, CN, $NO_2$, $NH_2$, optionally substituted $C_1$-$C_6$ alkyl, optionally substituted cycloalkyl, optionally substituted aryl, and optionally substituted heteroaryl, wherein optionally substituted substituents are optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

or $R^1$ and $R^2$ together form a fused cycloalkyl, cycloheteroalkyl, aryl, or heteroaryl group; each $R^3$ is selected, independently, from the group consisting of $SO_2NH_2$, $SO_2NHR^5$, $NHSO_2R^5$, $NHCO_2R^5$, $NHC(O)R^5$, $NHCONHR^5$, F, Cl, Br, I, $NO_2$, optionally substituted $C_1$-$C_6$ alkyl, optionally substituted $C_1$-$C_6$ alkoxy, optionally substituted cycloheteroaryl, and optionally substituted fused cycloheteroalkyl, wherein optionally substituted substituents are optionally substituted with sulfonyl;

each $R^4$ is selected, independently, from the group consisting of F, Cl, Br, I, $NO_2$, optionally substituted $C_1$-$C_6$ alkyl, optionally substituted $C_1$-$C_6$ alkoxy, COOH, $C(O)NH_2$, $C(O)R^5$, $C(O)NHR^5$, $CH_2C(O)R^5$, $SO_2NH_2$, $SO_2NHR^5$, $CONHSO_2R^5$, optionally substituted phenyl, optionally substituted OPhenyl, tetrazole, piperadinyl, piperazinyl, and morpholinyl, wherein optionally substituted substituents are optionally substituted with alkoxy, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

each $R^5$ is selected, independently, from the group consisting of optionally substituted $C_1$-$C_6$ alkyl, optionally substituted cycloalkyl, optionally substituted heteroaryl, and optionally substituted heteroalkyl, wherein optionally substituted substituents are optionally substituted with $C_1$-$C_6$ alkyl, $C_1$-$C_6$ alkoxyl, cycloalkyl, cycloheteroalkyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

$R^7$ is selected from the group consisting of H, $C_1$-$C_6$ alkyl, $C_1$-$C_6$ alkoxyl, halide, hydroxyl, cyano, nitro, and amino;

n is 0-5; and m is 1-5, or a pharmaceutically acceptable salt thereof.

Thus, in the disclosed compounds there can be from none to 5 different substituents $R^3$ and from 1 to 5 different substituents $R^4$. Pharmaceutically acceptable salts of these compounds are also disclosed. In some examples, $R^1$ is F, $R^2$ is hydrogen, and $R^3$ is 2-Cl. In one specific example, $R^1$ is Cl or F, $R^2$ is hydrogen, $R^3$ is hydrogen or 2-Cl, and $R^4$ is 4-$CONH_2$.

In certain embodiments, the disclosed compounds have the chemical structure shown in Formula II.

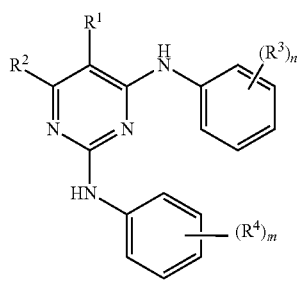

II wherein $R^1$-$R^4$ and m and n are as defined above for Formula I.

In some examples of Formula II, $R^1$ is selected from the group consisting of H, Cl, F, Br, I, $C_1$-$C_6$ alkyl, CN, $NO_2$, and $NH_2$. Also in Formula II, $R^2$ is selected from the group consisting of H, F, and Cl.

Additionally in Formula II, each $R^3$ is selected, independently, from the group consisting of Cl, Br, F, COOH, $CF_3$, CN, phenyl, $OCH_3$, $COR^5$, $CONH_2$, $CONR^5$, and $COONH_2$. When n is 0, there is no $R^3$.

Further in Formula II, each $R^4$ is selected, independently, from the group consisting of H, COOH, $CONH_2$, $CONR^5$, $SO_2NH_2$, $CONSO_2R^5$, tetrazole, 4-morpholine, and $COR^5$. Each $R^5$ is selected, independently, from the group consisting of optionally substituted $C_1$-$C_6$ alkyl, optionally substituted cycloalkyl, optionally substituted heteroaryl, and optionally substituted heteroalkyl. In some examples $R^5$ is an unsubstituted substituent.

Still further in Formula II, n is 0-5 (e.g., 0, 1, 2, 3, 4, or 5) and m is 1-5 (e.g., 1, 2, 3, 4, or 5). Thus, in the disclosed compounds there can be from none to 5 different substituents $R^3$ and from 1 to 5 different substituents $R^4$. In certain examples of Formula II, $R^1$ is F, $R^2$ is H, m is 3 and $R^4$ is 3,5-di-F, 4-OH. Pharmaceutically acceptable salts of these compounds are also disclosed.

In certain preferred aspects, the compound has Formula II, wherein $R^3$ is 2-Cl, and n is 1. In other examples, the compound has Formula II, n is 0 and there is no $R^3$. In other examples, the compound has Formula II, n is 2 and one $R^3$ is an otho-Cl and the other $R^3$ is a para hydroxyl, methoxyl, or cyano group. In other examples, the compound has Formula II, wherein $R^4$ is 4-$CONH_2$, and m is 1. In other examples, the compound has Formula II, wherein $R^4$ is 4-$CONHR^5$, and m is 1 In still other examples, the compound has Formula II, wherein $R^3$ is 2-Cl, n is 1, m is 1, and $R^4$ is COOH, $COR^5$, $CONH_2$, $CONR^5$, or $CONSO_2R^5$, wherein $R^5$ is $C_1$-$C_6$ alkyl, cycloalkyl, heteroaryl, or heteroalkyl. In other examples, the compound has Formula II, wherein $R^3$ is absent, n is 0, m is 1, and $R^4$ is COOH, $COR^5$, $CONH_2$, $CONR^5$, or $CONSO_2R^5$, wherein $R^5$ is $C_1$-$C_6$ alkyl, cycloalkyl, heteroaryl, or heteroalkyl.

Still further, the disclosed compounds can have the following Formula IIIA or IIIB:

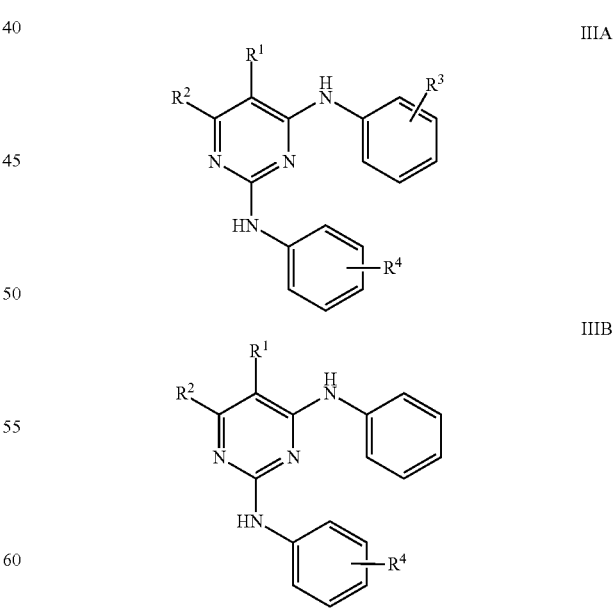

wherein $R^1$ is selected from the group consisting of H, Cl, F, Br, I, $CH_3$ and $NH_2$;

$R^2$ is selected from the group consisting of H, F, and Cl;

$R^3$ is selected from the group consisting of 2-Cl, 2-Br, 2-F, 2-COOH, 2-CF$_3$, 2-CN, 2-phenyl, 2-OCH$_3$, 2-COONH$_2$, 4-COOH, and 4-OCH$_3$; and $R^4$ is selected from the group consisting of H, COOH, 2-CONH$_2$, 4-CONH$_2$, SO$_2$NH$_2$, tetrazole, and 4-morpholine.

In Formula IIIA or IIIB, $R^1$ is selected from the group consisting of H, Cl, F, Br, I, CH$_3$ and NH$_2$; $R^2$ is selected from the group consisting of H, F, and Cl.

Also in Formula IIIA, $R^3$ is selected from the group consisting of 2-Cl, 2-Br, 2-F, 2-COOH, 2-CF$_3$, 2-CN, 2-phenyl, 2-OCH$_3$, 2-COONH$_2$, 4-COOH, and 4-OCH$_3$.

Additionally in Formula IIIA or IIIB, $R^4$ is selected from the group consisting of H, COOH, 2-CONH$_2$, 4-CONH$_2$, SO$_2$NH$_2$, tetrazole, and 4-morpholine.

Still further, the disclosed compounds can have the following Formula IV:

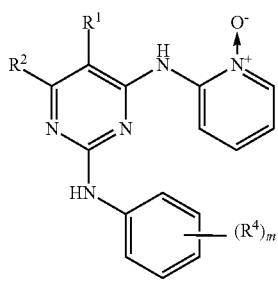

IV

In Formula IV, $R^1$, $R^2$, $R^4$, and m are as defined herein.

In other examples, disclosed herein are compounds of Formula IA.

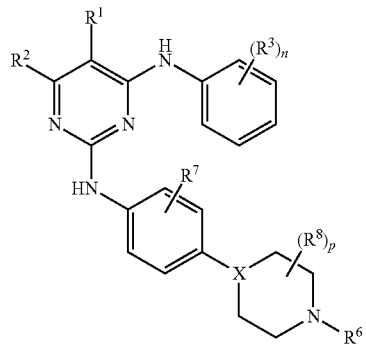

IA wherein
X is CH or N;
$R^1$ is selected from the group consisting of H, Cl, F, Br, I, CN, NO$_2$, NH$_2$, CF$_3$, CO$_2$H, CO$_2$NH$_2$, CO$_2$NHR$^5$, CO$_2$R$^5$, C(O)R$^5$, C(O)NH$_2$, C(O)NHR$^5$, and C$_1$-C$_6$ alkyl optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;
$R^2$ is H, OH, CN, NO$_2$, NH$_2$, optionally substituted C$_1$-C$_6$ alkyl, optionally substituted cycloalkyl, optionally substituted aryl, and optionally substituted heteroaryl; wherein optionally substituted substituents are optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;
or $R^1$ and $R^2$ together form a fused cycloalkyl, cycloheteroalkyl, aryl or heteroaryl group;
each $R^3$ is selected, independently, from the group consisting of SO$_2$NH$_2$, SO$_2$NHR$^5$, NHSO$_2$R$^5$, NHCO$_2$R$^5$, NHC(O)R$^5$, NHCONHR$^5$, F, Cl, Br, I, NO$_2$, optionally substituted C$_1$-C$_6$ alkyl, optionally substituted C$_1$-C$_6$ alkoxy, optionally substituted cycloheteroaryl, and optionally substituted fused cycloheteroalkyl, wherein optionally substituted substituents are optionally substituted with sulfonyl;
each $R^5$ is selected, independently, from optionally substituted C$_1$-C$_6$ alkyl, optionally substituted C$_1$-C$_6$ cycloalkyl, optionally substituted aryl, optionally substituted heteroaryl, optionally substituted heterocycloalkyl, and optionally substituted heteroalkyl, wherein optionally substituted substituents are optionally substituted with C$_1$-C$_6$ alkyl, C$_1$-C$_6$ alkoxyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;
$R^6$ is selected from the group consisting of H, C$_1$-C$_6$ alkyl, C$_1$-C$_6$ alkyl-OH, CO$_2$R$^5$, CO$_2$H, and CO$_2$NHR$^5$;
$R^7$ is selected from the group consisting of H, C$_1$-C$_6$ alkyl, C$_1$-C$_6$ alkoxyl, halide, hydroxyl, cyano, nitro, and amino;
$R^8$ is OH or =O;
n is 0-5; and
p is 1 or 2
or a pharmaceutically acceptable salt thereof.

In other examples, disclosed herein are compounds of Formula IB.

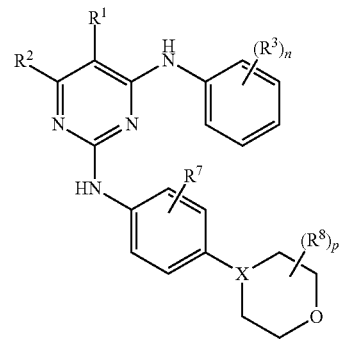

IB wherein
X is N or CH;
$R^1$ is selected from the group consisting of H, Cl, F, Br, I, CN, NO$_2$, NH$_2$, CF$_3$, CO$_2$H, CO$_2$NH$_2$, CO$_2$NHR$^5$, CO$_2$R$^5$, C(O)R$^5$, C(O)NH$_2$, C(O)NHR$^5$, and C$_1$-C$_6$ alkyl optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;
$R^2$ is selected from the group consisting of H, OH, CN, NO$_2$, NH$_2$, optionally substituted C$_1$-C$_6$ alkyl, optionally substituted cycloalkyl, optionally substituted aryl, and optionally substituted heteroaryl, wherein optionally substituted substituents are optionally substituted with C$_1$-C$_6$ alkyl, cycloalkyl, aryl, or heteroaryl substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

or $R^1$ and $R^2$ together form a fused cycloalkyl, cycloheteroalkyl, aryl or heteroaryl group;

each $R^3$ is selected, independently, from the group consisting of $SO_2NH_2$, $SO_2NHR^5$, $NHSO_2R^5$, $NHCO_2R^5$, $NHC(O)R^5$, $NHCONHR^5$, F, Cl, Br, I, $NO_2$, optionally substituted $C_1$-$C_6$ alkyl, optionally substituted $C_1$-$C_6$ alkoxy, optionally substituted cycloheteroaryl, and optionally substituted fused cycloheteroalkyl, wherein optionally substituted substituents are optionally substituted with sulfonyl;

each $R^5$ is selected, independently, from the group consisting of optionally substituted $C_1$-$C_6$ alkyl, optionally substituted cycloalkyl, optionally substituted heteroaryl, and optionally substituted heteroalkyl, wherein optionally substituted substituents are optionally substituted with $C_1$-$C_6$ alkyl, $C_1$-$C_6$ alkoxyl, cycloalkyl, cycloheteroalkyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

$R^6$ is selected from the group consisting of H, $C_1$-$C_6$ alkyl, $CO_2R^5$, $CO_2H$, and $CO_2NHR^5$;

$R^7$ is selected from the group consisting of H, $C_1$-$C_6$ alkyl, $C_1$-$C_6$ alkoxyl, halide, hydroxyl, cyano, nitro, and amino;

$R^8$ is OH or $=$O;

n is 0-5; and p is 1 or 2 or a pharmaceutically acceptable salt thereof.

In other examples, disclosed herein are compounds of Formula V.

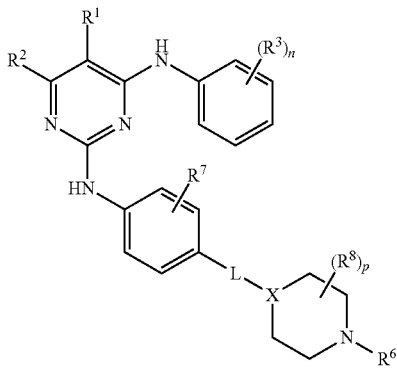

V wherein

X is N or CH;

L is selected from the group consisting of O, S, $C_{1-4}$alkyl, C(O)NH, NHC(O), $CH_2$C(O), C(O)$CH_2$, $CH_2CH_2$C(O), $CH_2$C(O)$CH_2$, $CH_2$C(O)NH, and NH(CO)$CH_2$;

$R^1$ is selected from the group consisting of H, Cl, F, Br, I, CN, $NO_2$, $NH_2$, $CF_3$, $CO_2H$, $CO_2NH_2$, $CO_2NHR^5$, $CO_2R^5$, C(O)$R^5$, C(O)$NH_2$, C(O)$NHR^5$, and $C_1$-$C_6$ alkyl optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

$R^2$ is selected from the group consisting of H, OH, CN, $NO_2$, $NH_2$, optionally substituted $C_1$-$C_6$ alkyl, optionally substituted cycloalkyl, optionally substituted aryl, and optionally substituted heteroaryl, wherein optionally substituted substituents are optionally substituted with alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol;

or $R^1$ and $R^2$ together form a fused cycloalkyl, cycloheteroalkyl, aryl, or heteroaryl group;

each $R^3$ is selected, independently, from the group consisting of $SO_2NH_2$, $SO_2NHR^5$, $NHSO_2R^5$, $NHCO_2R^5$, $NHC(O)R^5$, $NHCONHR^5$, F, Cl, Br, I, $NO_2$, optionally substituted $C_1$-$C_6$ alkyl, optionally substituted $C_1$-$C_6$ alkoxy, optionally substituted cycloheteroaryl, and optionally substituted fused cycloheteroalkyl, wherein optionally substituted substituents are optionally substituted with sulfonyl;

each $R^5$ is selected, independently, from the group consisting of optionally substituted $C_1$-$C_6$ alkyl, optionally substituted cycloalkyl, optionally substituted heteroaryl, and optionally substituted heteroalkyl, wherein optionally substituted substituents are optionally substituted with $C_1$-$C_6$ alkyl, $C_1$-$C_6$ alkoxyl, cycloalkyl, cycloheteroalkyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

$R^6$ is selected from the group consisting of H, $C_1$-$C_6$ alkyl, $CO_2R^5$, $CO_2H$, and $CO_2NHR^5$;

$R^7$ is selected from the group consisting of H, $C_1$-$C_6$ alkyl, $C_1$-$C_6$ alkoxyl, halide, hydroxyl, cyano, nitro, and amino;

$R^8$ is OH or $=$O;

n is 0-5; and p is 1 or 2 or a pharmaceutically acceptable salt thereof.

In certain specific examples of Formula I-V, $R^1$ and $R^2$ together form a fused cycloalkyl, cycloheteroalkyl, aryl or heteroaryl group. In other examples, $R^1$ and $R^2$ together form a fused furan. In other examples, $R^1$ and $R^2$ together form a fused cyclopentyl or fused cyclohexyl. In other examples, $R^1$ and $R^2$ together form a fused phenyl.

In certain specific examples of Formula I-V, $R^1$ is $C_1$-8 alkyl or heteroalkyl. In other examples, $R^1$ is methyl, ethyl, or trifluoromethyl. In other examples, $R^1$ is chloro, bromo, or fluoro. In other examples, $R^1$ is $CO_2C_{1-8}$ alkyl, $CO_2H$, $CO_2NH_2$, or $CO_2NHC_{1-8}$ alkyl.

In certain specific examples of Formula I-V, $R^2$ is $C_{1-8}$ alkyl or heteroalkyl. In other examples, $R^2$ is hydrogen.

In the disclosed compounds there can be from 1 to 5 different substituents $R^3$, i.e., n can be 1 to 5, though preferable n can be 1 to 3. In some examples, there is no $R^3$ substituent, i.e., n is 0. In specific examples, $R^3$ is $SO_2NH_2$, $SO_2NHR^5$, or $NHSO_2R^5$, wherein $R^5$ is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is $NHC(O)R^5$, wherein $R^5$ is $C_1$-$C_6$ alkyl or $C_1$-$C_6$ cycloalkyl optionally substituted with $C_1$-$C_6$ alkyl, $C_1$-$C_6$ alkoxyl, cycloalkyl, cycloheteroalkyl, hydroxyl, or halide. In other examples, $R^3$ is $C_1$-$C_6$ alkyl or $C_1$-$C_6$ cycloalkyl. In other examples, $R^3$ is $C_1$-$C_6$ alkoxyl. In other examples, $R^3$ is halide. In other examples, n is 2 and each $R^3$ is selected from the group consisting of $C_1$-$C_6$ alkyl, $C_1$-$C_6$ alkoxyl, halide, $SO_2NH_2$, $SO_2NHR^5$, and $NHSO_2R^5$, wherein $R^5$ is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, n is 2 and each $R^3$ is selected from the group consisting of $C_1$-$C_6$ alkyl, $C_1$-$C_6$ alkoxyl, and halide. In other examples, n is 3 and each $R^3$ is selected from the group consisting of $C_1$-$C_6$ alkyl, $C_1$-$C_6$ alkoxyl, and halide. In other examples, n is 2 and each $R^3$ together form a fused heterocycloalkyl.

In certain specific examples of the above formula, $R^1$ is F and $R^2$ is H.

In certain specific examples, $R^4$ is C(O)NH$R^5$.

In certain specific examples, $R^6$ is C$_{1-8}$ alkyl. In other examples, $R^6$ is methyl. In other examples, $R^6$ is hydrogen.

In certain specific examples, $R^7$ is chloro, bromo, or fluoro. In other examples, $R^7$ is hydrogen.

In some examples, X is N.

In specific examples, L is CH$_2$(O) or C(O)NH.

In specific examples, n and m are both 1. In other examples, n is 0.

In specific examples $R^8$ is oxo and p is 1. In other examples $R^8$ is oxo and p is 2.

Pharmaceutically acceptable salts of these compounds are also disclosed.

Specific examples of compounds having Formula I, IA, IB, II, III, IV, and V are disclosed herein are in Tables 1-4.

TABLE 1

Bisanilinipyrimidine analogs.

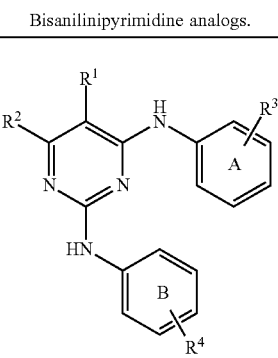

| Entry | Cmpd ID # | $R^1$ | $R^2$ | $R^3$ | $R^4$ |
|---|---|---|---|---|---|
| 1 | 1 | H | H | ortho-COOH | para-COOH |
| 2 | 3a | H | H | ortho-COOH | ortho-CONH$_2$ |
| 3 | 3b | H | H | ortho-COOH | H |
| 4 | 3c | H | H | ortho-COOH | para-morpholine |
| 5 | 3d | H | H | ortho-COOH | ortho-COOH |
| 6 | 3e | H | H | ortho-COOMe | para-COOMe |
| 7 | 3f | H | H | H | H |
| 8 | 3g | H | H | ortho-COONH$_2$ | para-CONH$_2$ |
| 9 | 3h | H | H | H | para-COOH |
| 10 | 3i | H | H | para-COOH | para-COOH |
| 11 | 3j | CH$_3$ | H | ortho-COOH | para-COOH |
| 12 | 3k | H | CH$_3$ | ortho-COOH | para-COOH |
| 13 | 3l | H | H | ortho-Cl | para-COOH |
| 14 | 3m | F | H | ortho-COOH | All H |
| 15 | 3n | F | H | ortho-COOH | para-COOH |
| 16 | 3o | F | H | ortho-Cl | para-COOH |
| 17 | 3p | F | H | ortho-Cl | H |
| 18 | 3q | H | H | ortho-COOH | meta-COOH |

TABLE 1-continued

Bisanilinipyrimidine analogs.

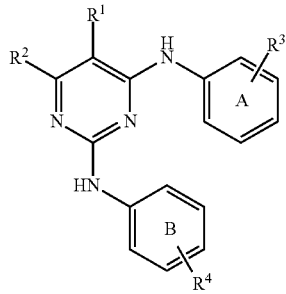

| Entry | Cmpd ID # | $R^1$ | $R^2$ | $R^3$ | $R^4$ |
|---|---|---|---|---|---|
| 19 | 3r | F | H | ortho-COOH | meta-COOH |
| 20 | 4c | Cl | Cl | ortho-COOH | para-COOH |
| 21 | 4d | Cl | H | ortho-COOH | para-COOH |
| 22 | 4a | NH$_2$ | H | ortho-COOH | para-COOH |
| 23 | 4b | H | NH$_2$ | ortho-COOH | para-COOH |

TABLE 2

Bisanilinipyrimidine analogs.

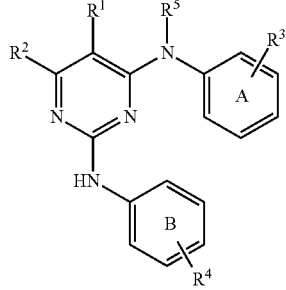

| Entry | Cmpd ID # | $R^1$ | $R^2$ | $R^3$ | $R^4$ | $R^5$ |
|---|---|---|---|---|---|---|
| 24 | 6a | H | H | ortho-F | para-COOH | H |
| 25 | 6b | H | H | ortho-CF$_3$ | All H | H |
| 26 | 6c | H | H | 2-Cl-4-F | para-COOH | H |
| 27 | 6d | H | H | ortho-OCF$_3$ | para-COOH | H |
| 28 | 6e | H | H | ortho-OMe | para-COOH | H |
| 29 | 6f | H | H | ortho-OMe | All H | H |
| 30 | 6g | H | H | ortho-CN | All H | H |
| 31 | 6h | H | H | ortho-CF$_3$ | para-COOH | H |
| 31 | 6i | H | H | ortho-Br | para-COOH | H |
| 33 | 6j | H | H | ortho-Cl | para-CH$_2$—COOH | H |
| 34 | 6k | H | H | Ortho-Cl | para-COOH, meta-OH | H |
| 35 | 6l | H | H | Ortho-F | All H | H |
| 36 | 6m | H | H | Ortho-I | para-COOH | H |
| 37 | 6n | H | H | Ortho-CN | para-COOH | H |
| 38 | 6o | H | H | Ortho-Cl | meta-COOH | H |
| 39 | 6p | H | H | ortho-Cl | para-CONH$_2$ | H |
| 40 | 6q | H | H | ortho-phenyl | para-COOH | H |
| 41 | 6r | H | H | ortho-Cl | para-COOH | CH$_3$ |
| 42 | 6s | H | H | ortho-Cl | para-COOH | CH$_3$—CH$_2$ |
| 43 | 6t | F | H | ortho-Cl | meta-COOH | H |

TABLE 3

Bisanilinipyrimidine analogs.

| Entry | Compound ID |
|---|---|
| 44 | 9a (RE1-043) |
| 45 | 9b (Re1-032) |
| 46 | 9c (RE1-031) |
| 47 | 9d (RE1-025) |//

TABLE 3-continued

Bisanilinipyrimidine analogs.

| Entry | Compound ID |
|---|---|
| 48 | 9e (RE1-039) |
| 49 | 9f (RE1-019) |
| 50 | 9g (HM5-018-2) |
| 51 | 9h (YL5-146-4) |

TABLE 3-continued

Bisanilinipyrimidine analogs.

| Entry | Compound ID |
|---|---|
| 52 | 6p (YL5-145) |
| 53 | 9i (YL5-146-3) |
| 54 | 9j (HM6-007-1) |
| 55 | 9k (HM6-020-2) |
| 56 | 9l (HM4-153-2) |
| 57 | 9m (HM6-021-4) |
| 58 | 9n (HM6-029-1) |
| 59 | 13a (SO2-162) |

TABLE 3-continued

Bisanilinipyrimidine analogs.

| Entry | Compound ID |
|---|---|
| 60 | 13b (SO3-033) |
| 61 | 13c (SO3-036) |
| 62 | 13d (SO3-035) |

TABLE 4

Bisanilinipyrimidine analogs.

| CompoundID | Cmpd # | R¹ | R² | R³ | R⁴ |
|---|---|---|---|---|---|
| RK2-014 | 14 | H | H | meta-CF$_3$ | para-COOH |
| RK2-017-01 | 15 | H | H | meta-CF$_3$ | para-CONH$_2$ |
| RK2-037 | 16 | H | H | meta-CF$_3$ | meta-isobutyramide |
| RK2-025 | 17 | H | H | meta-CF$_3$ | meta-CF$_3$ |
| RK2-015-03 | 18 | H | H | meta-CF$_3$ | ortho-COOH |
| RK2-017-02 | 19 | H | H | meta-CF$_3$ | meta-CONH$_2$ |
| RK2-053 | 20 | H | H | meta-CF$_3$ | meta-acetamide |
| RK2-015-02 | 21 | H | H | meta-CF$_3$ | meta-COOH |
| RK2-056 | 22 | H | H | meta-CF$_3$ | meta-butyramide |
| RK2-046-02 | 23 | H | H | meta-CF$_3$ | meta-propionamide |
| RK2-013 | 24 | H | H | meta-CF$_3$ | meta-cyclopropane carboxamide |
| RK2-015-01 | 25 | H | H | meta-CF$_3$ | All H |
| RK2-046-01 | 26 | H | H | meta-CF$_3$ | meta-$^t$butylcarboxyamide |
| RK2-044 | 27 | H | H | meta-CF$_3$ | meta-cyclopentyl-carboxamide |
| RK2-052 | 28 | H | H | meta-CF$_3$ | meta-isobutylcarboxamide |
| RK2-043 | 29 | H | H | meta-CF$_3$ | meta-(4-chlorobenzyl)carboxamide |
| RK2-049 | 30 | H | H | meta-CF$_3$ | meta-benzylcarboxamide |
| YL5-048 | 31 | H | Me$_2$N | H | All H |
| YL5-050 | 32 | H | Me$_2$N | ortho-COOH | All H |
| YL5-068 | 33 | NH$_2$ | H | ortho-COOH | para-COOC$_2$H$_5$ |
| YL5-146-5 | 34 | H | H | ortho-Cl | para-OCH$_3$ |
| YL5-080 | 35 | Me | H | ortho-COOH | para-COOH |

In further example, the compound can be one of the following compounds.

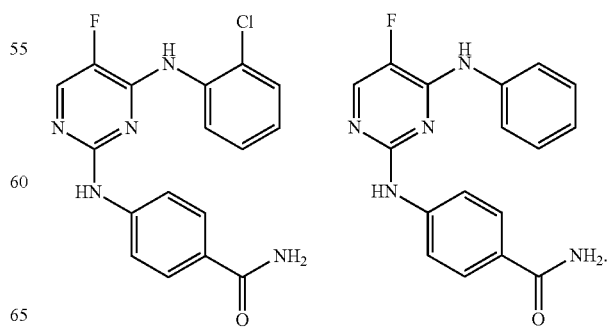

In still further examples, the compound can have Formula IIIC:

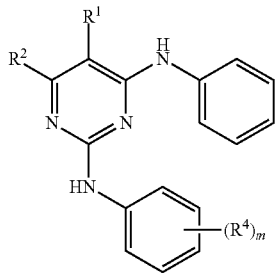

IIIC wherein
R' is selected from the group consisting of H, Cl, F, Br, I, $C_1$-$C_6$ alkyl, CN, $NO_2$, and $NH_2$;
$R^2$ is selected from the group consisting of H, F, and Cl; and
each $R^4$ is selected, independently, from the group consisting of H, COOH, $CONH_2$, $CONR^5$, $SO_2NH_2$, $CONSO_2R^5$, tetrazole, 4-morpholine, and $COR^5$;
each $R^5$ is selected, independently, from the group consisting of $C_1$-$C_6$ alkyl, cycloalkyl, heteroaryl, and heteroalkyl; and
m is 1-5,
or a pharmaceutically acceptable salt thereof.

In specific examples of Formula IIIC, m is 1 and $R^4$ is selected from the group consisting of COOH, 2-$CONH_2$, 4-$CONH_2$, $SO_2NH_2$, tetrazole, and 4-morpholine. In other examples, R' is Cl, F, Br, or I. In further examples, $R^2$ is H. In still further examples, the compound is:

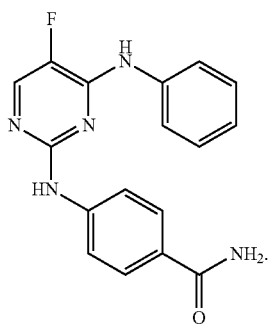 [SMILES: NC(=O)c1ccc(Nc2ncc(F)c(Nc3ccccc3)n2)cc1]

Further specific examples, include

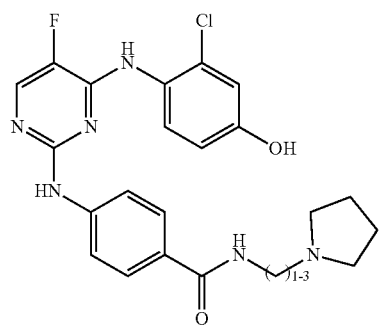

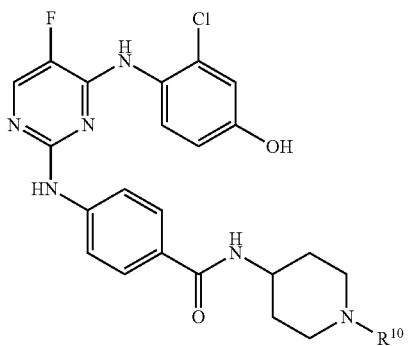

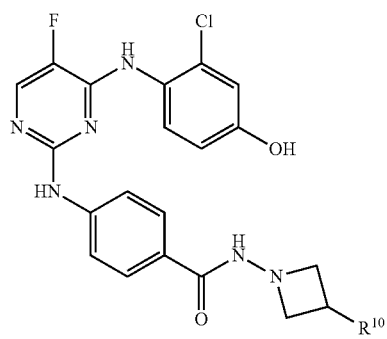

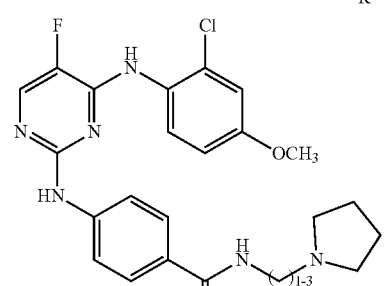

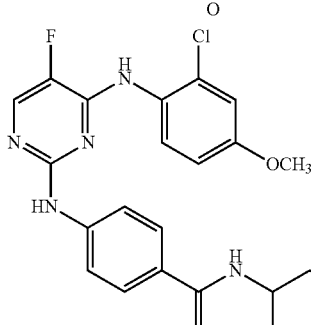

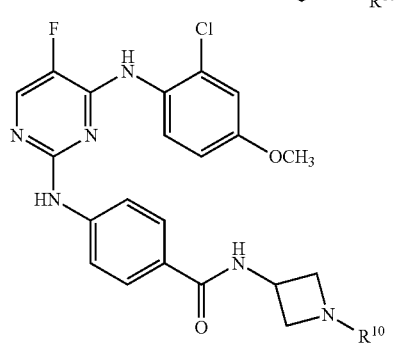

-continued

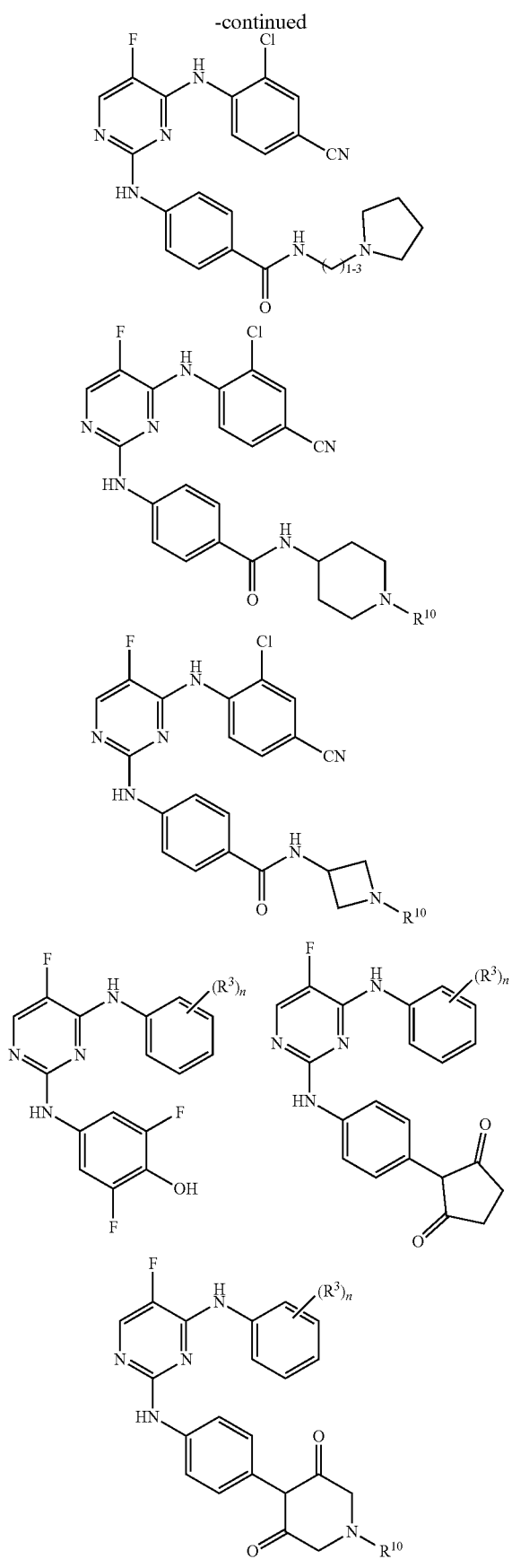

wherein $R^3$ and n are as defined in Formula I, and $R^{10}$ is hydrogen, $C_1$-$C_6$ alkyl, or $C_1$-$C_6$ alkyl-OH.

Scheme I describes the general synthetic route used for preparation of dianilinipyrimidine (1) from readily available building blocks. The 2,4-dichloropyrimidine was initially reacted with the requisite commercially available anilines with the method predominantly using isopropanol as the solvent, with reflux heating to obtain the required analog.

Method

Further provided herein are methods of reducing the risk of developing, preventing, or treating graft versus host disease (GVHD) in a subject. The method can include administering to the subject an effective amount of a compound or composition as disclosed herein. The methods can further include administering a second compound or composition, such as, for example, an immunosuppressant.

Also disclosed are methods for treating GVHD in a patient. In one embodiment, an effective amount of one or more compounds or compositions disclosed herein is administered to a patient at risk of developing or have GVHD and who is in need of treatment thereof. The patient can be a human or other mammal, such as a primate (monkey, chimpanzee, ape, etc.), dog, cat, cow, pig, or horse, or other animals at risk of developing or have GVHD. GVHD may be due to a transplantation procedure involving the implantation of immunogenic tissue including but are not limited to, solid organ transplants (such as heart, kidney, and liver), tissue grafts (such as skin, intestine, pancreas, cornea, gonad, bone, and cartilage), and cellular transplants (such as cells from pancreas, brain and nervous tissue, muscle, skin, bone, cartilage, and liver). In such procedures, organ rejection is an obstacle to complete recovery. The individual's immune system recognizes antigens (HLA or minor H antigens) on the implanted tissue as foreign and mounts an immune response against it, which injures and destroys the implanted tissue.

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Administration

The disclosed compounds can be administered in combination with pharmaceutical formulations. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of GVHD, the compounds disclosed herein can be administered to a patient at risk of developing GVHD or in need of treatment in combination with other known treatments for GVHD. These other substances or treatments can be given at the same as or at different times from the compounds disclosed herein. For example, the compounds disclosed herein can be used in combination with an immunosuppressive agent such as IMUREK™ (azathioprine sodium), brequinar sodium, SPANIDIN™ (gusperimus trihydrochloride, also known as deoxyspergualin), mizoribine (also known as bredinin), CELLCEPT™ (mycophenolate mofetil), NEORAL™ (Cyclosporin A; also marketed as a different formulation under the trademark SANDIMMUNE™), PROGRAF™ (tacrolimus, also known as FK-506), RAPIMMUNE™ (sirolimus, also known as rapamycin), leflunomide (also known as HWA-486), ZENAPAX™, glucocortcoids, such as prednisolone and its derivatives, corticosteroids, antibodies such as orthoclone (OKT3), cyclophosphamide, methotrexate, 6-mercaptopurine, vincristine, antithymyocyte globulins, such as thymoglobulins; an Aurora A inhibitor; or a Janus kinase 2 inhibitor. A conventional immunosuppressant drug, such as those above, may thus be administered in an amount substantially less (e.g. 20% to 50% of the standard dose) than when the compound is administered alone. The compounds described herein can be administered at regular intervals over a time period of at least 2 weeks.

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of a transplant, optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more immunosuppressant agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Material and Methods:

Monoclonal antibodies and flow cytometry: Fluorochrome-conjugated mouse anti-human monoclonal antibodies included anti-CD3, CD4, CD25, CD39, CD107a, CD127, CTLA4, Foxp3, LAG3, phosphorylated STAT3 Y705, phosphorylated STAT5 Y694, and phosphorylated H3 serine 10 (BD Biosciences, San Jose, CA; eBioscience San Jose, CA; Cell Signaling Technology, Boston, MA). LIVE/DEAD Fixable Yellow Dead Cell Stain (Life Technologies, Grand Island, NY USA) was used to determine viability. Live events were acquired on a FACSCalibur or LSRII flow cytometer (FlowJo software, ver. 7.6.4; TreeStar, Ashland, OR).

Allogeneic mixed leukocyte reactions: Bulk donor T-cells were allostimulated with allogeneic DCs (DC:T-cell ratio of 1:30) as previously described (OneBlood, Tampa, FL) (15, 16, 20). For synergy assays, TG101348 (JAK2 inhibitor, Chemietek, Indianapolis, IN), Alisertib (Aurora kinase A inhibitor, Selleckchem, Houston, TX), or both TG101348 and Alisertib (ratio 1:5, respectively) were added once on day 0. bisanilinopyrimidine (I) (dual JAK2 and Aurora kinase A inhibitor (27, 29), Moffitt Chemical Biology Core, Tampa, FL) or DMSO was added once on day 0 at concentrations ranging from 0.078-2.5 µM. As indicated, alloMLRs consisting of $T_{reg}$ depleted, naïve CD4$^+$ T-cells (Miltenyi Biotec Inc, San Diego, CA) were treated with a combination of ARL67156 (CD39 inhibitor, 125 µM, Sigma), AJI, or DMSO on day 0 to study the role of CD39 and ATP in this system. T-cell proliferation was measured on day 5 by a colorimetric assay (CellTiter 96 Aqueous One Solution Cell Proliferation Assay [MTS]; or CellTiter Blue, Promega, Madison, WI). Absorbance/optical density (OD) was analyzed at 490 nm or 590 nm, respectively. Proliferation (%)=(OD treated alloMLR−OD T-cells alone)/(OD DMSO alloMLR−OD T-cells alone)×100.

Protein phosphorylation in T-cells: T-cells were cultured with allogeneic DCs (DC:T-cell ratio of 1:30) for 5 days in RPMI/10% pooled human serum, with alisertib (1.75 µM), TG101348 (350 nM), a combination of both inhibitors, AJI-214 (750 nM), AJI-100 (750 nM), or DMSO control added once on day 0. After 5 days, T cells were then harvested and directly fixed (Cytofix, BD Biosciences) for 10 min at 37° C. After washing with phosphate-buffered saline, the T cells were permeabilized with icecold methanol (90%, v/v) for at least 20 min at −20° C. The cells were stained for expression of CD3 and pH3Ser$^{10}$.

STAT3 and STAT5 phosphorylation: As indicated, T cells were serum-starved in RPMI treated with DMSO diluent control, alisertib, TG101348, a combination of both inhibitors, AJI-214, or AJI-100 for 4 hours. IL-6-induced pSTAT3 or IL-2-induced pSTAT5 (Y694) was measured by flow cytometry.

NSG mice: After transplantation and treatment with either AJI-100 or vehicle control, human T cells were isolated from recipient mouse spleens at day +14, stained for pH3Ser[10] or pSTAT3 (+IL-6 stimulation), and analyzed as described.

Effect of dual pathway inhibition on effector CD4 T cell differentiation: Purified human T-cells were allostimulated with DCs at a DC:T-cell ratio of 1:30 in RPMI/10% pooled human serum. DMSO, alisertib (1.75 mM), TG101348 (350 nM), both alisertib and TG101348, AJI-214 (750 nM), or AJI-100 (750 nM) was added once on day 0. The T cells were harvested and surface-stained on day 5 for CD3, CD4, CD25, and CD127. Activated CD4$^+$ T$_{conv}$ were characterized by expression of CD25 and CD127, and activated CD8$^+$ T$_{conv}$ (CD3$^+$ and CD4$^-$) were identified by CD25 expression. The absolute number of CD4$^+$ and CD8$^+$ T$_{conv}$ was calculated by flow cytometry using CountBright beads (Life Technologies). T$_H$1 cells were characterized by expression of CD3, CD4, and intracellular IFN-γ (after an additional 4 to 5 hours of stimulation with PMA/ionomycin). For T$_H$1 experiments, purified CD4$^+$ T cells were used as opposed to bulk T cells.

iT$_{reg}$ differentiation and potency: iT$_{regs}$ were generated as previously described in the presence of alisertib (1.75 mM), TG101348 (350 nM), both alisertib and TG101348, AJI-214 (750 nM), AJI-100 (750 nM), or DMSO. On day 5, iT$_{regs}$ were isolated and washed to minimize drug carry-over as reported. The T cells were harvested and surface-stained on day 5 for CD3, CD4, CD25, and CD127, followed by fixation and permeabilization (eBioscience) and Foxp3 staining. The absolute number of iT$_{reg}$ was calculated by flow cytometry using CountBright beads (Life Technologies). The purified iT$_{regs}$ were titrated against alloMLRs consisting of responder CD4$^+$CD25$^-$ T cells (5×10$^4$) from the iT$_{regs}$ donor and fresh allogeneic DCs (1.6×10$^3$) to determine suppressive potency. T cell proliferation was determined by pulsing cells with [$^3$H]thymidine (1 mCi per well). Surface expression of CD39 and LAG5 was evaluated on the iT$_{regs}$. iT$_{regs}$ production of CTLA4 was assessed by intracellular staining after a 5-hour treatment of PMA/ionomycin, with GolgiStop added during the last 4 hours of incubation. iT$_{regs}$ synthesis of IL-10 and TGF-β (Quansys Biosciences) was quantified from supernatants using multiplex cytokine assays after PMA/ionomycin stimulation.

ATP Hydrolysis assay: iT$_{regs}$ generated in the presence of AJI-241 (750 nM) or DMSO were plated in V-bottom 96 well plates in serum free media at a concentration of 75,000 cells per 100 μL. ARL67156 (125 μM) was added or not as indicated. A fixed dose of ATP (50 μM) was added to the cells and incubated at 37° C. for 45 minutes. ATP consumption was measured by a luminescence assay per the manufacturer's instructions (Promega, CellTiter-Glo Luminescent Cell Viability Assay) and read by a spectrofluorimeter. Percent consumption was calculated as (luminescence of test supernatant/luminescence of 50 μM ATP cell-free control supernatant)×100.

Foxp3 TSDR demethylation analysis: Foxp3 TSDR demethylation was analyzed among magnetic bead-purified (Miltenyi), allostimulated bisanilinopyrimidine (I)- and DMSO-treated iT$_{regs}$. The primer selection, procedure for amplifying methylation and demethylation specific TSDR products, genomic DNA isolation, bisulfite conversion, and qPCR were performed as previously reported.

RORgammaT expression by RT-PCR: Naïve CD4$^+$ T cells were purified and allostimulated (DC/T cell ratio of 1:30) as reported (B. C. Betts et al., CD4$^+$ T cell STAT5 phosphorylation precedes acute GVHD, and subsequent T$_H$17 tissue invasion correlates with GVHD severity and therapeutic response. *J. Leukocyte Biol*. (2015)). Alisertib (1.75 mM), TG101348 (350 nM), both alisertib and TG101348, AJI-214 (750 nM), AJI-100 (750 nM), or DMSO control was added once on day 0. Medium was supplemented with IL-6 (1×10$^5$ IU/mL), TGF-β (4 ng/mL; R&D Systems), and anti-IFN-γ monoclonal antibody (10 mg/ml; eBioscience) to polarize T$_H$17. After 5 days, the T cells were harvested, washed, and then plated at 35,000 cells per well in an IL-17 ELISPOT plate (R&D Systems). The CD4$^+$ T cells were stimulated with PMA/ionomycin, and the ELISPOT assay was performed according to the manufacturer's instructions.

Xenogeneic GVHD model: NOD scid gamma (NSG) mice (male or female, 6-24 weeks old) were purchased from Jackson Laboratory (Bar Harbor, ME, USA) and raised per an IACUC-approved protocol in adherence to the NIH Guide for the Care and Use of Laboratory Animals. Mice received either (i) alisertib (30 mg/kg daily), TG101348 (45 mg/kg twice a day), a combination of alisertib and TG101348, or vehicle (methylcellulose) by oral gavage or (ii) AJI-100 (50 mg/kg daily) or vehicle (50% polyethylene glycol, 15% 2-hydroxypropyl-b-cyclodextrin, and 10% DMSO in sterile saline) ip from day 0 to day +14.

Mice were monitored for GVHD clinical scores (K. R. Cooke et al., An experimental model of idiopathic pneumonia syndrome after bone marrow transplantation: I. The roles of minor H antigens and endotoxin. *Blood* 88, 3230 (1996)), weight, and premoribund status. As indicated, mice were euthanized on day +14 to study recipient spleen T$_{conv}$, T$_{regs}$, T$_H$1, T$_H$17, B cells, and T-cell signal transduction. Human CD4$^+$ T$_{reg}$ (CD25$^+$, CD127$^-$, Foxp3$^+$), T$_{conv}$ (CD25$^+$, CD127$^+$), T$_H$1, T$_H$17, and CD19$^+$ B cells residing in recipient spleens were quantified by flow cytometry. T-cell pH3 ser10 and PSTAT3 were evaluated by flow cytometry. IL-17 ELISPOTs were performed using isolated human T cells from recipient mouse spleen as described above. Tissue samples were prepared, stained (Ventana Medical Systems, Tucson, AZ), and imaged (Vista, CA, USA) to identify human T-cells as previously described. All vertebrate animal work was IACUC-approved.

CTL generation and tumor lysis assays: NSG mice were transplanted with human PBMCs as described above, and treated with either AJI-100 (50 mg/kg daily) or vehicle control. Additionally, recipient mice received an inoculum of irradiated U937 cells (ATCC, 10$^7$/mouse) on days 0 and +7. Mice were euthanized between days +10 to +12, spleens were harvested, and human CD8$^+$ T-cells were isolated by magnetic bead separation. Fresh U937 target cells were labeled with Calcein-AM for 30 minutes, washed, and then cultured with the purified CD8$^+$ T-cells at varying effector to target ratios for 4 hours at 37° C. No additional drugs were added during this final culture. The amount of supernatant fluorescence released by the target cells was measured using a spectrofluorimeter (485 nm excitation and 535 nm emission) (S. Neri, E. Mariani, A. Meneghetti, L. Cattini, A. Facchini, Calcein-acetyoxymethyl cytotoxicity assay: standardization of a method allowing additional analyses on recovered effector cells and supernatants. *Clinical Diagnostic Lab. Immunol*. 8, 1131 (2001)). Percent lysis was calculated as follows: [(test fluorescence−spontaneous fluorescence)/(maximum fluorescence−spontaneous fluorescence)]×100. For in vitro CTL generation, human PBMCs were cultured with irradiated U937 cells at a ratio of 1:1 in the presence of bisanilinopyrimidine (I) 750 nM or DMSO for 10 days. Cultures were replenished with media and inhibitors on days +3 and +7, and fresh irradiated U937 cells added on day +7. On day +10, the cells were harvested and CD8 T-cells were isolated by magnetic bead separation (Miltenyi).

The tumor lysis assay was performed as described using fresh, Calcein-AM labeled U937 targets.

Statistical Analysis: For comparisons of paired data sets, the paired t test was used. ANOVA was used for group comparisons. Survival comparisons were made using the log-rank test. The Mann-Whitney test was used for all others. The statistical analysis was conducted using Prism software version 5.04 (GraphPad). Statistical significance was defined by $P<0.05$ (two-tailed).

For drug combination experiments, the results were analyzed for synergistic, additive, or antagonistic effects using the combination index (CI) method developed by Chou and Talalay. The dose-effect curve for each drug alone was determined based on experimental observations using the median-effect principle and then compared to the effect achieved with a combination of the two drugs to derive a CI value. For this analysis, XLfit software (IDBS) was used to create log-log dose-fractional effect plots for each drug and combination and to regress a straight line through the points and was used to calculate the values of $D_m$ and m for use in the median-effect equation as follows: $f_a/f_u=(D/D_m)_m$, where D is the dose of the drug, $D_m$ is the dose required for a 50% effect (analogous to $IC_{50}$), $f_a$ and $f_u$ are the affected and unaffected fractions, respectively ($f_a=1-f_u$), and m is the exponent signifying the sigmoidicity of the dose-effect curve. The CI calculation chosen for the analysis of the drug combinations was the isobologram equation for mutually nonexclusive drugs with different modes of action as follows: $CI=(D)_1/(D_x)_1+(D)_2/(D_x)_2+(D)_1(D)_2/(D_x)1(D_x)_2$, where $(D_x)_1$ and $(D_x)_2$ in the denominators are the concentrations for drug 1 and drug 2 alone that gave x % inhibition, whereas $(D)_1$ and $(D)_2$ in the numerators are the concentrations of drug 1 and drug 2 in combination that also inhibited x % (that is, isoeffective).

Synthesis of bisanilinopyrimidine (I) and bisanilinopyrimidine (II): The bisanilinopyrimidine bisanilinopyrimidine (I) was prepared using a method previously reported (Lawrence, et al., Development of o-chlorophenyl substituted pyrimidines as exceptionally potent aurora kinase inhibitors. J. Med. Chem. 2012, 55, 7392-416.). The bisanilinopyrimidine bisanilinopyrimidine (II) was prepared using a two step route (Scheme I) to prepare other 2,4-dianilinopyrimidines (1). Reaction of 2,4-dichloro-5-fluoropyrimidine with aniline provided the intermediate 1. Intermediate 1 was reacted further with 4-aminobenzamide to give the required bisanilinopyrimidine (II), with HPLC purity >99%.

Scheme I: Synthetic route for preparation of bisanilinopyrimidine (II).

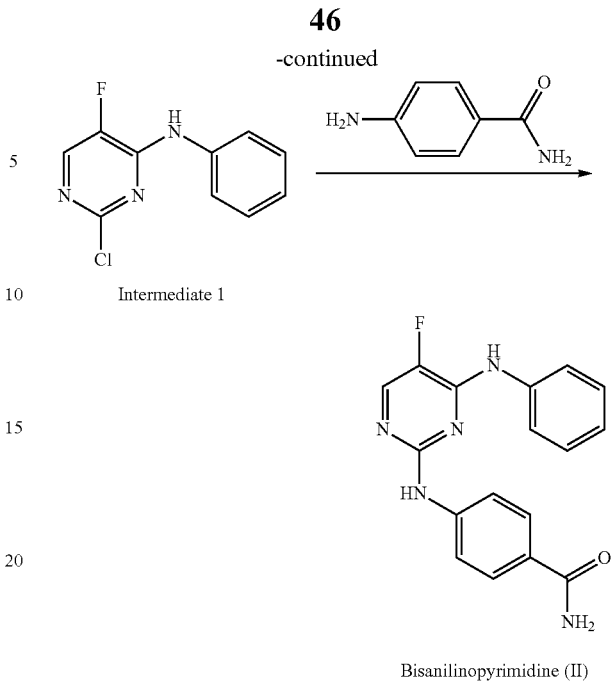

Intermediate 1

Bisanilinopyrimidine (II)

2-Chloro-5-fluoro-N-phenylpyrimidin-4-amine (intermediate 1): To a solution of 5-fluoro-2,4-dichloropyrimidine (2.00 g, 11.98 mmol) and diethylisopropylamine (2.50 mL, 14.37 mmol) in isopropanol (12 mL) was added aniline (1.09 mL, 11.98 mmol). The mixture was stirred at reflux for 1 h. The reaction mixture was concentrated under reduced pressure. The residue was dissolved in dichloromethane (20 mL) and washed with water (10 mL) and brine (10 mL). The organic layer was dried ($Na_2SO_4$) and concentrated under reduced pressure. The resulting solid was triturated using EtOAc/hexanes to give the title compound as a white solid (1.35 g, 50%). Mp: 135-136° C. $^1$H NMR (400 MHz, DMSO-d6): δ 9.99 (s, 1H, disappeared on $D_2O$ shake), 8.30 (d, J=3.5 Hz, 1H), 7.66 (d, J=8.0 Hz, 2H), 7.37 (t, J=8.0 Hz, 2H), 7.13 (t, J=8.0 Hz, 1H). $^{19}$F NMR (376 MHz, DMSO-d6): δ -153.7 (s). HPLC-MS (EMI: m/z 226.1 [40%, $(M_{37}Cl+H)+$], 224.1 [100%, $(M_{35}Cl+H)^+$]. 5-Fluoro-N4-phenyl-N2-[4-(4-carboxamide)phenyl]pyrimidine-2,4-diamine (bisanilinopyrimidine (II)): A mixture of intermediate 1 (1.00 g, 4.47 mmol), 4-aminobenzamide (0.609 g, 4.47 mmol), and methanol (4.5 mL) was heated at 100° C. for 14 h. The reaction mixture was cooled to room temperature and the precipitate filtered and washed with MeOH (2×10 mL). The resulting solid was sonicated in saturated sodium bicarbonate solution (10 mL) for 2 min, then filtered, washed with water (3×20 mL), MeOH (2×10 mL), and dried to give bisanilinopyrimidine (II) as a white solid (1.07 g, 74%). Mp: 248-249° C. HPLC: 99.9% [tR=10.9 min, 50% MeOH, 50% water (with 0.1% TFA), 20 min]. $^1$H NMR (400 MHz, DMSO-d6): δ 9.51 (s, 1H, disappeared on $D_2O$ shake), 9.44 (s, 1H, disappeared on $D_2O$ shake), 8.14 (d, J=3.7 Hz, 1H), 7.77 (brs, 1H, disappeared on $D_2O$ shake), 7.76 (d, J=7.8 Hz, 2H), 7.72 (s, 4H), 7.36 (t, J=7.8 Hz, 2H), 7.12 (brs, 1H, disappeared on $D_2O$ shake), 7.10 (t, J=7.8 Hz, 1H). $^{19}$F NMR (376 MHz, DMSO-d6): δ -163.2 (s). HPLC-MS (ESI$^+$): m/z 324.2 [100%, (M+H)$^+$]. LC-MS (EMI: 992.3 [20%, (3M+Na)$^+$], 669.2 [50%, (2M+Na)$^+$], 346.1 [30%, (M+Na)$^+$], 324.1 [100%, (M+H)$^+$]. HRMS (ESI$^+$): m/z calcd for $C_{17}H_{14}FN_5O$ (M+H)±324.1255, found 324.1262.

Study 1:

Synergistic immune suppression with combined inhibition of Aurora kinase A and JAK2 Using allogeneic mixed leukocyte reactions (alloMLRs), the JAK2 inhibitor, TG101348, reduced alloreactive T-cell proliferation at concentrations of 350 nM and greater as previously reported (15) (FIG. 1A). The Aurora kinase A inhibitor, alisertib (M. G. Manfredi et al., Characterization of Alisertib (MLN8237), an investigational smallmolecule inhibitor of aurora A kinase using novel in vivo pharmacodynamic assays. *Clinical Cancer research* 17, 7614 (2011); H. Yang et al., Dual Aurora A and JAK2 kinase blockade effectively suppresses malignant transformation. *Oncotarget* 5, 2947 (2014)), suppressed the proliferative response of T-cells in alloMLRs at 625 nM (32.5% inhibition) with an $IC_{50}$ of 10 µM (FIG. 1A). Synergistic suppression over T-cells allostimulated by dendritic cells (DC) was achieved when TG101348 and alisertib were added together at a ratio of 1:5, respectively, with a calculated combination index (CI) of <1 per the Chou and Talalay method (T. C. Chou, Theoretical basis, experimental design, and computerized simulation of synergism and antagonism in drug combination studies. *Pharmacol. Rev.* 58, 621 (2006)) (FIG. 1A). The observed $IC_{50}$ of the combination correlated with 350 nM of TG101348 and 1.75 µM of alisertib (FIG. 1A).

Figure 1B:
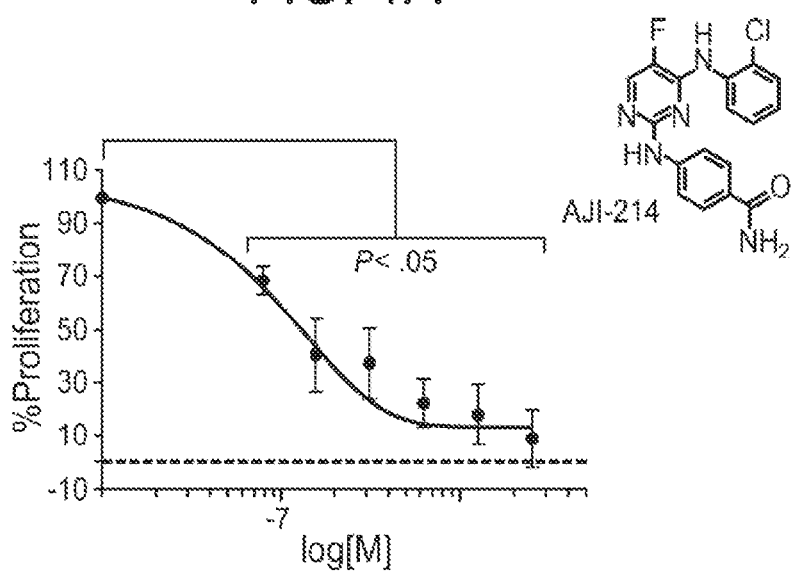
Figure 1C:
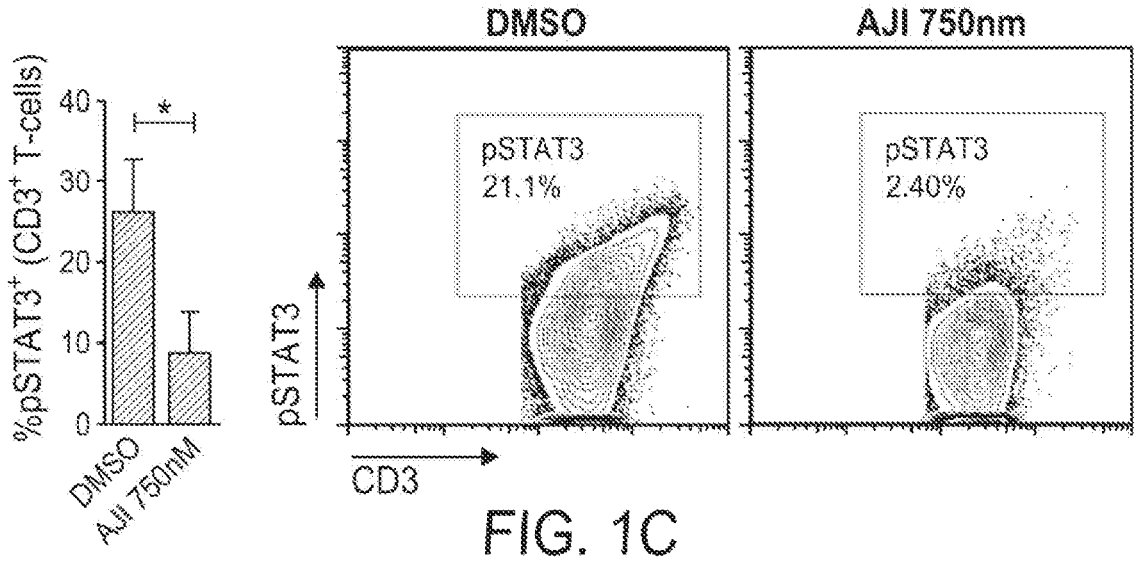
Figure 1D:
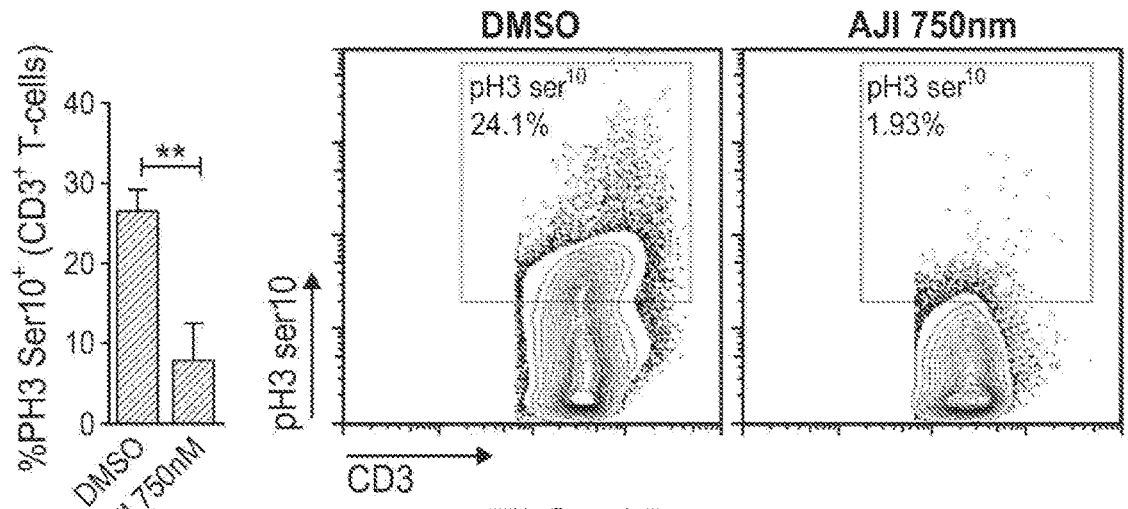
Figures 1E, 2A, 2B, 2C:
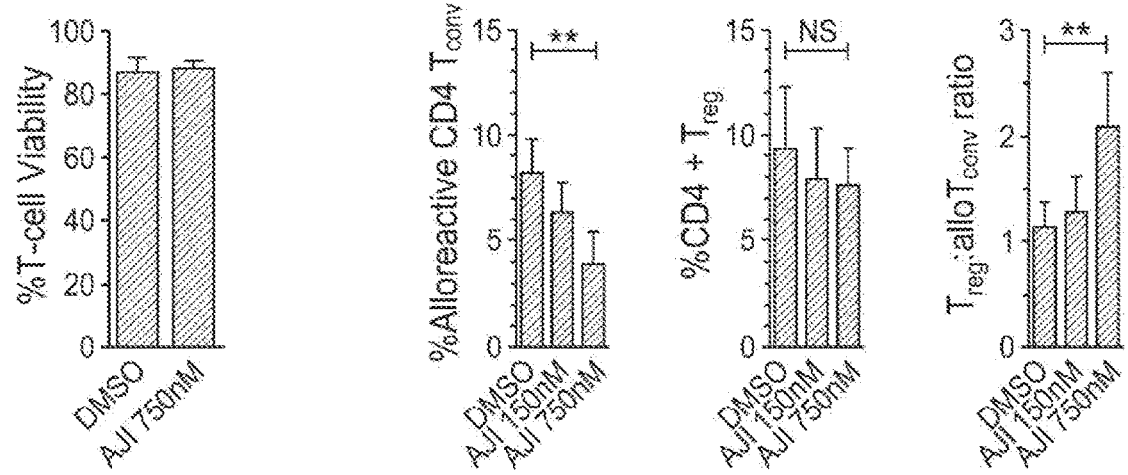

Bisanilinopyrimidine (I) is a potent inhibitor of Aurora kinase A and JAK2 that was designed and synthesized at Moffitt Cancer Center (H. R. Lawrence et al., Development of o-chlorophenyl substituted pyrimidines as exceptionally potent aurora kinase inhibitors. *J. Med. Chem.* 55, 7392 (2012)). Bisanilinopyrimidine (I) exerted significant suppression over Tcells in alloMLRs, with single agent efficacy at nanomolar concentrations (FIG. 1B). Bisanilinopyrimidine (I) significantly decreased the activity of Aurora kinase A and JAK2 in DC-allostimulated T-cells, and reduced phosphorylation of histone 3 serine 10 (pH3 Ser10) and signal transducer and activator of transcription 3 (pSTAT3 Y705) respectively (FIGS. 1C-1D). The viability of AJI-214 (750 nM) or DMSO treated T-cells was similar after 5 days of co-culture (FIG. 1E).

Figure 2D:
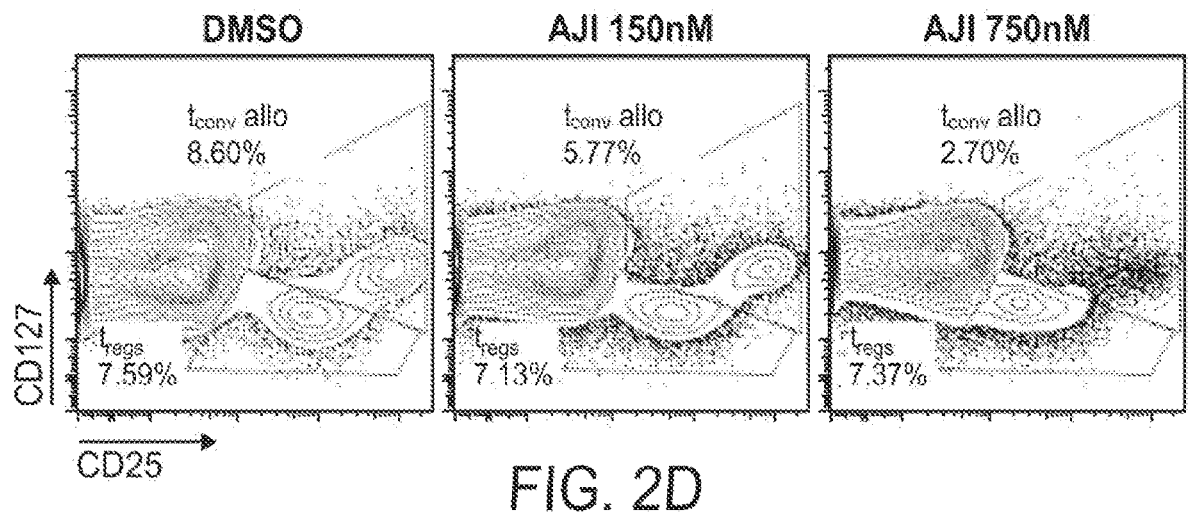

Concurrent blockade of Aurora kinase A and JAK2 selectively impairs alloreactive $T_{conv}$, while sparing responder $T_{regs}$ bisanilinopyrimidine (I) exerted dose-dependent inhibition of alloreactive $CD4^+$ $T_{conv}$ ($CD25^+$, $CD127^+$) (A. K. Heninger et al., IL-7 abrogates suppressive activity of human $CD4^+CD25^+FOXP3^+$ regulatory T cells and allows expansion of alloreactive and autoreactive T cells. *J. Immunol.* 189, 5649 (2012); S. Samarasinghe et al., Functional characterization of alloreactive T cells identifies CD25 and CD71 as optimal targets for a clinically applicable allodepletion strategy. *Blood* 115, 396 (2010); S. Touil et al., Depletion of T regulatory cells through selection of CD127-positive cells results in a population enriched in memory T cells: implications for anti-tumor cell therapy. *Haematologica* 97, 1678 (2012)) in alloMLRs (FIG. 2A). The $CD4^+$ $T_{reg}$ ($CD25^+$, $CD127^-$) (W. Liu et al., CD127 expression inversely correlates with FoxP3 and suppressive function of human $CD4^+$ $T_{reg}$ cells. *J. Experi. Med.* 203, 1701 (2006); N. Seddiki et al., Expression of interleukin (IL)-2 and IL-7 receptors discriminates between human regulatory and activated T cells. *J. Experi. Med.* 203, 1693 (2006)) population was preserved even when co-cultures were exposed to 750 nM of bisanilinopyrimidine (I) (FIG. 2B). The high degree of selectivity demonstrated by dual inhibition of Aurora kinase A and JAK2 resulted in a significant increase in the $T_{reg}$:allo $T_{conv}$ ratio (FIG. 2C-2D). Cell Trace Violet dilution was used to study the effect of dual Aurora kinase A/JAK2 blockade on proliferation among the individual $T_{reg}$ and $T_{conv}$ compartments. This verified the observed shifts in $T_{reg}$:$T_{conv}$ populations by bisanilinopyrimidine (I) exposure, where a significant decrease in $T_{conv}$ proliferation occurred with bisanilinopyrimidine (I) at 750 nM (FIGS. 2E-2F). $T_{reg}$ proliferation was similar between bisanilinopyrimidine (I) and control (FIGS. 2E-2F). STAT5 activation remained functional in IL-2 stimulated $CD4^+$ T-cells exposed to either DMSO or bisanilinopyrimidine (I) compared with unstimulated baseline controls, though the effect was blunted by bisanilinopyrimidine (I) (FIG. 2G). Moreover, $CD4^+$, $CD25^+$, $CD127^-$ $T_{reg}$ expression of Foxp3 was maintained in the presence of bisanilinopyrimidine (I) or DMSO (FIG. 2H).

To confirm the $T_{reg}$-sparing effects were related to concurrent inhibition of JAK2 and Aurora kinase A, as opposed to a phenomenon of bisanilinopyrimidine (I) alone, similar allogeneic co-cultures were treated with either TG101348 (JAK2 inhibitor, 350 nM), alisertib (Aurora kinase A inhibitor, 1.75 µM), a combination of TG101348 and alisertib, or DMSO. These doses of TG101348 and alisertib were based on the synergy studies, where a 1:5 ratio of each respective compound was used concurrently. As observed with bisanilinopyrimidine (I), dual blockade of JAK2 and Aurora kinase A reduced the alloreactive $T_{conv}$ population and spared the responder $T_{regs}$ (FIG. 2I).

Dual inhibition of Aurora kinase A and JAK2 favors $iT_{reg}$ development and potency. The effects of dual Aurora A/JAK2 blockade on inducible $T_{reg}$ ($iT_{reg}$) differentiation was studied. Naïve $CD4^+$ T-cells (>99% pure) were depleted of natural $T_{regs}$ and stimulated with allogeneic DCs for 5 days in the presence of bisanilinopyrimidine (I) or DMSO (FIG. 3A). Bisanilinopyrimidine (I) permitted $iT_{reg}$ differentiation, and significantly decreased the frequency of alloreactive $T_{conv}$ (FIGS. 3B-3C). Given that $iT_{regs}$ are derived from phenotypically plastic naïve $CD4^+$ T-cells, it was confirmed that demethylated Foxp3 TSDR was similar among bisanilinopyrimidine (I)- and DMSO-exposed $iT_{reg}$ (FIG. 3D). To determine the influence of Aurora A versus JAK2 inhibition on $iT_{reg}$ differentiation, co-cultures were treated with bisanilinopyrimidine (I) 750 nM, alisertib 1.75 µM, TG101348 350 nM, a combination of both, or DMSO. While alisertib, TG101348, and the combination of each all had less absolute numbers of $iT_{regs}$ and allo $T_{conv}$ compared to DMSO, the suppressive effect on $T_{conv}$ was greater resulting in incrementally larger $T_{reg}$:allo $T_{conv}$ ratios (FIG. 3E).

Figure 4A:
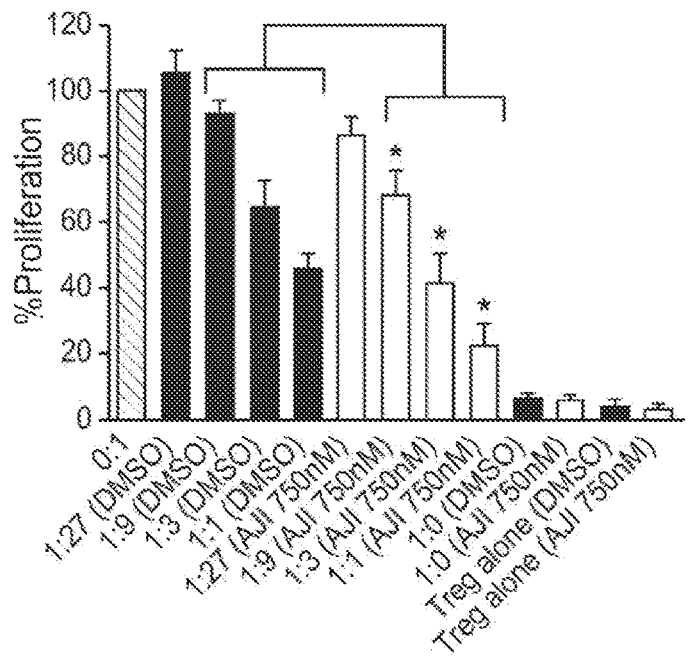
FIGS. 4A-4B show combined inhibition of Aurora kinase A and JAK2 enhances antigen-specific iT$_{reg}$ suppressive potency.
Figure 4B:
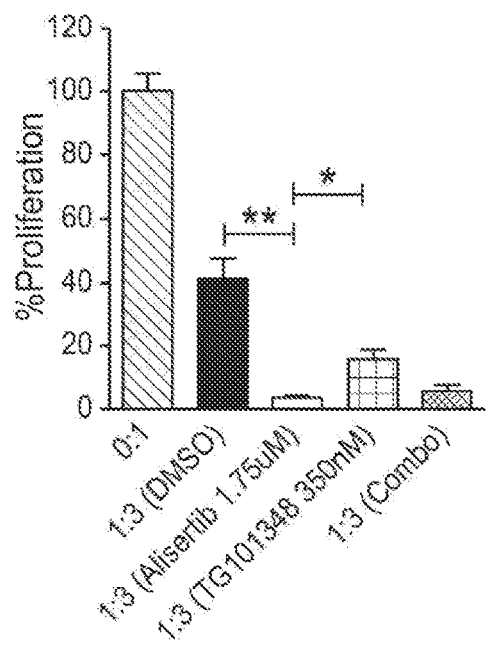

Bisanilinopyrimidine (I) demonstrated minimal loss of $iT_{regs}$ and significantly reduced allo $T_{conv}$ compared to DMSO, increasing the $iT_{reg}$:allo $T_{conv}$ ratio (FIG. 3E). To study the influence of dual pathway inhibition on $iT_{reg}$ suppressive function, bisanilinopyrimidine (I)- or DMSO-treated $iT_{reg}$ were cultured with self alloresponders targeting fresh allogeneic DCs. The bisanilinopyrimidine (I)-treated $iT_{reg}$ not only demonstrated intact suppressive function, their potency was significantly increased by approximately 30% compared to DMSO-treated $iT_{reg}$ (FIG. 4A). It was then explored how Aurora kinase A versus JAK2 blockade contributed to this enhanced suppression by the $iT_{regs}$. $iT_{regs}$ were generated as described in the presence of alisertib, TG101348, a combination of both, or DMSO. Interestingly, Aurora kinase A inhibition with alisertib demonstrated superior suppressive capacity compared with either DMSO- or TG101348-exposed $iT_{reg}$ (FIG. 4B). The combination of alisertib with TG101348 was similar to alisertib alone (FIG. 4B).

Figures 5A, 5B:
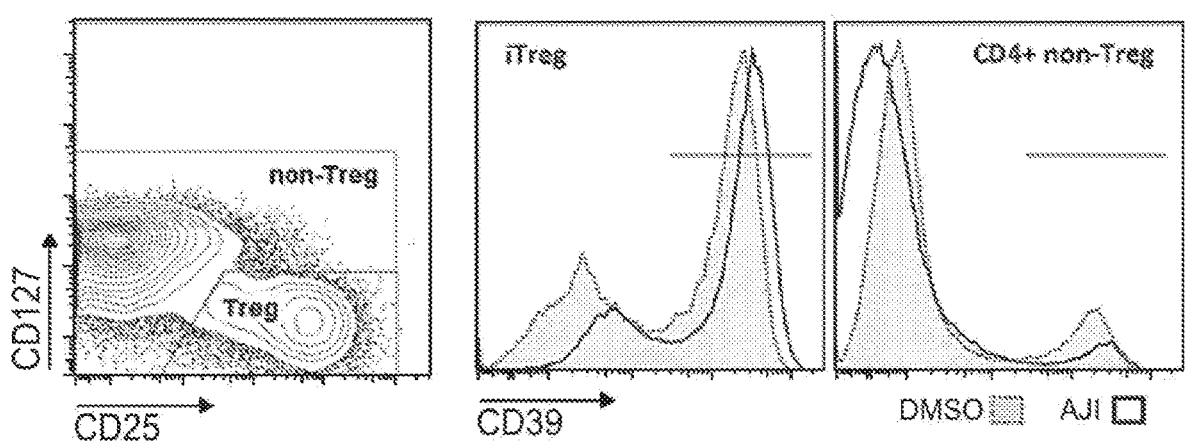
FIGS. 5A-5J show targeting Aurora kinase A and JAK2 increases CD39 expression and ATP scavenging among iT$_{reg}$.
Figure 5C:
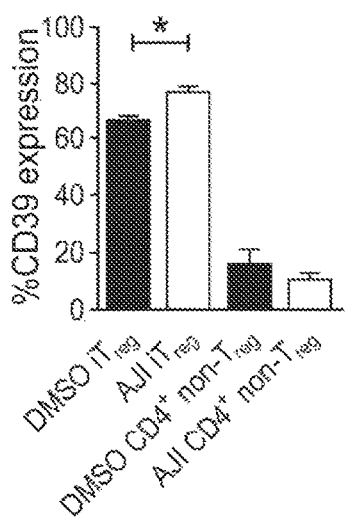
Figure 5D:
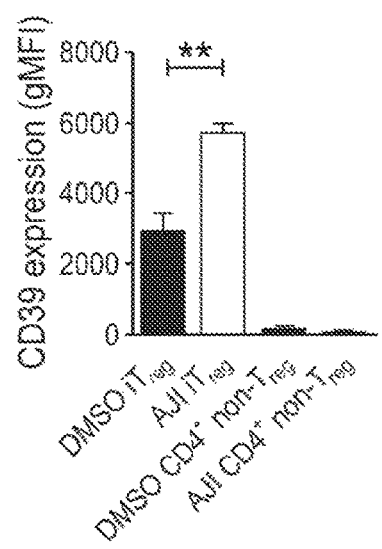
Figure 5E:
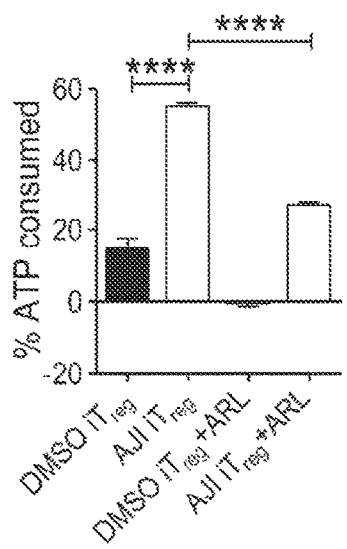
Figure 5F:
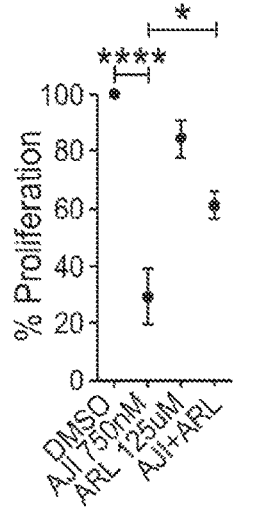
Figures 5G, 5H:
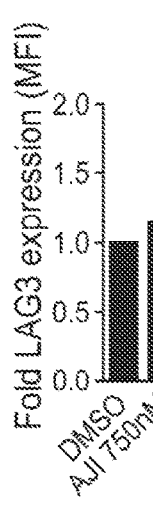
Figures 5I, 5J:
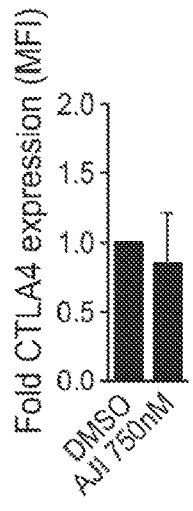

Also investigated was the mechanism supporting the increased iT$_{reg}$ function observed with bisanilinopyrimidine (I). Identified was a significant increase in the relative surface density of CD39, an ectonucleotidase that hydrolyzes ATP, among the bisanilinopyrimidine (I)-exposed iT$_{reg}$ compared with DMSO controls (FIGS. 5A-5D). CD39 expression on non-T$_{reg}$ CD4$^+$ T-cells was minimal (M. Mandapathil et al., Generation and accumulation of immunosuppressive adenosine by human CD4$^+$ CD25highFOXP3$^+$ regulatory T cells. *J. Biol. Chem.* 285, 7176 (2010)) (FIG. 5B). It was confirmed that the higher CD39 expression among the bisanilinopyrimidine (I) treated iT$_{reg}$ resulted in improved scavenging of extracellular ATP, compared to DMSO-treated iT$_{reg}$ (FIG. 5E). The enhanced hydrolysis of ATP by the AJI-treated iT$_{regs}$ was also significantly impaired by blocking the CD39 enzyme with ARL67156 (FIG. 5E). To determine the influence of CD39$^+$ iT$_{reg}$ in the overall efficacy of dual Aurora A/JAK2 blockade, ARL67156 was added to alloMLRs consisting of natural T$_{reg}$-depleted CD4$^+$ T-cell responders with bisanilinopyrimidine (I) or DMSO. This eliminated potential interference from CD39$^+$ natural T$_{reg}$ within the allogeneic co-culture. CD39 blockade significantly weakened the T-cell inhibition by bisanilinopyrimidine (I) (FIG. 5F), supporting that CD39$^+$ iT$_{regs}$ contribute to the immune suppressive effects of bisanilinopyrimidine (I). With regard to other modes of iT$_{reg}$ suppression, no difference in their expression of LAG3, CTLA4, or production of IL-10 or TGF-beta after exposure to bisanilinopyrimidine (I) or DMSO (FIGS. 5G-5J).

Figure 6A:
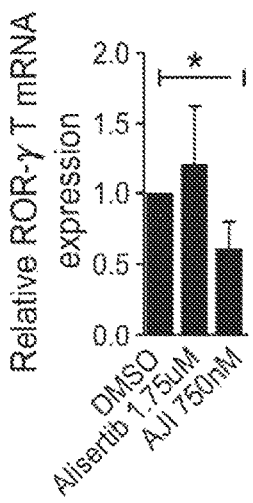
FIGS. 6A-6B show Aurora kinase A inhibition does not impair T$_H$17 differentiation. Isolated naïve CD4$^+$ T-cells were stimulated with allogeneic DCs for 5 days with alisertib, AJI-214, TG101348, or DMSO. Media was supplemented with IL-6, TGF-beta, and anti-IFN-γmAb to promote RORgammaT expression. The bar graphs depict replicate means of relative RORgammaT expression±SEM among drug- and control-treated CD4$^+$ T-cells (unpaired t-test). Data are from one representative experiment of 2 performed in triplicate for each figure. *P<0.05, **P=0.001-0.01.
Figure 6B:
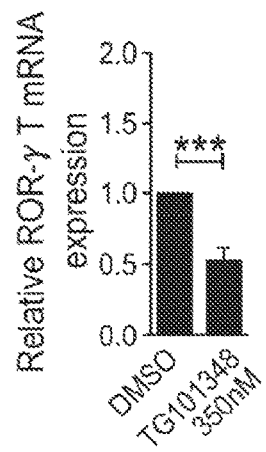

As previously reported JAK2 inhibition with TG101348 impairs T$_H$17 production of IL-17, it was investigated how Aurora kinase A inhibition influenced RORgammaT expression. Alisertib exerted no effect on RORgammaT levels among alloresponder CD4$^+$ T-cells, while JI-214 significantly decreased the expression of this key T$_H$17-differentiation transcription factor compared with DMSO (FIG. 6A). It was confirmed that TG101348 significantly decreases RORgammaT expression in CD4$^+$ alloresponders (FIG. 6B). These data suggest that bisanilinopyrimidine (I) supports enhanced iT$_{reg}$ potency primarily through Aurora kinase A blockade, while its suppression of T$_H$17 polarization is a function of JAK2 blockade.

Figure 7A:
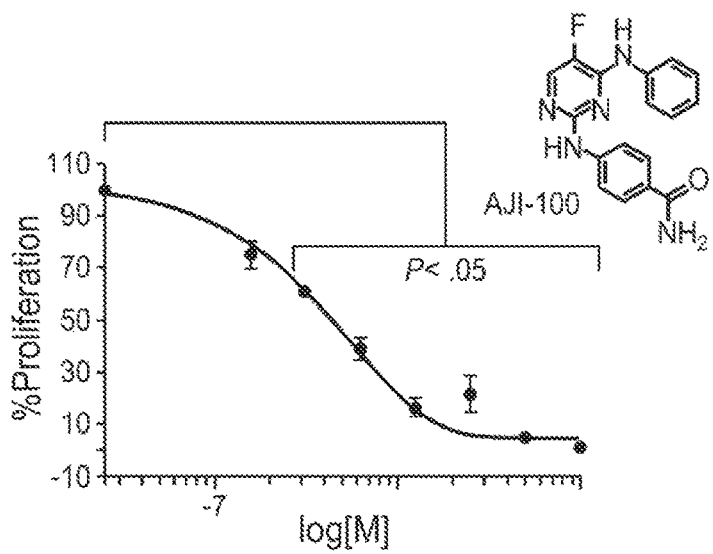
FIGS. 7A-7H show blockade of Aurora kinase A and JAK2 reduces xenogeneic GVHD and preserves anti-tumor CTL function.

Targeting Aurora kinase A and JAK2 reduces xenogeneic GVHD and preserves GVL A xenogeneic GVHD model was used to investigate the in vivo efficacy of dual Aurora kinase A/JAK2 blockade while maintaining a focus on human immune responses. Recipient NSG mice were transplanted with 30×10$^6$ human PBMCs i.p. once on day 0. Bisanilinopyrimidine (I) is not suited for in vivo use, due to limited bioavailability. Bisanilinopyrimidine (II) is an Aurora kinase A/JAK2 inhibitor (Moffitt Cancer Center) that differs from bisanilinopyrimidine (I) by only a chlorine to hydrogen substitution at the ortho position of its phenyl ring enhancing its solubility. The bisanilinopyrimidine (II) and bisanilinopyrimidine (I) analogues both inhibit Aurora kinase A and JAK2 with similar potency. As observed with bisanilinopyrimidine (I), bisanilinopyrimidine (II) reduced responder T-cell proliferation in alloMLRs at nanomolar concentrations (IC$_{50}$ 200 nM, FIG. 7A).

Figure 7B:
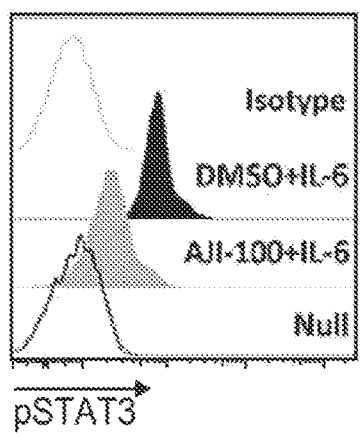
Figure 7C:
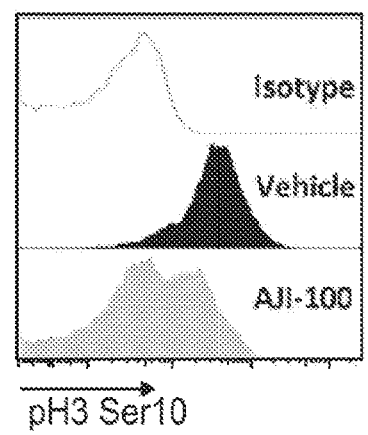
Figure 7D:
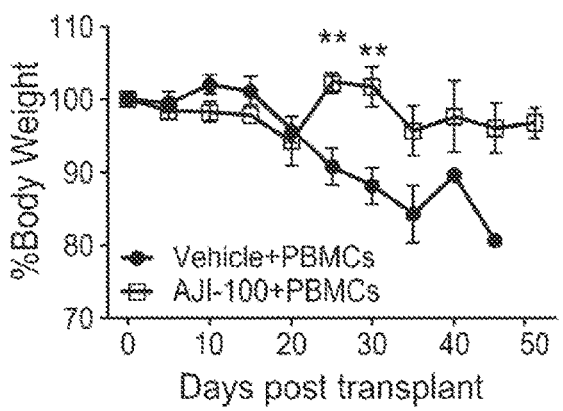
Figure 7E:
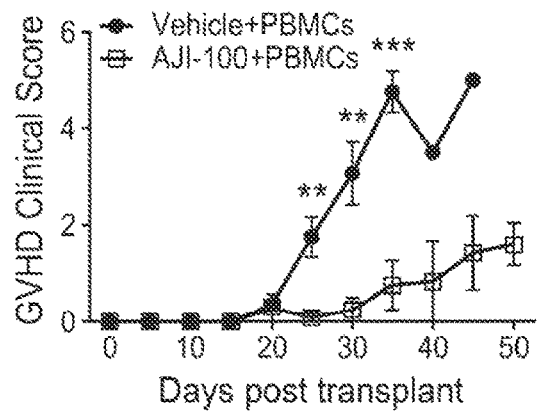
Figure 7F:
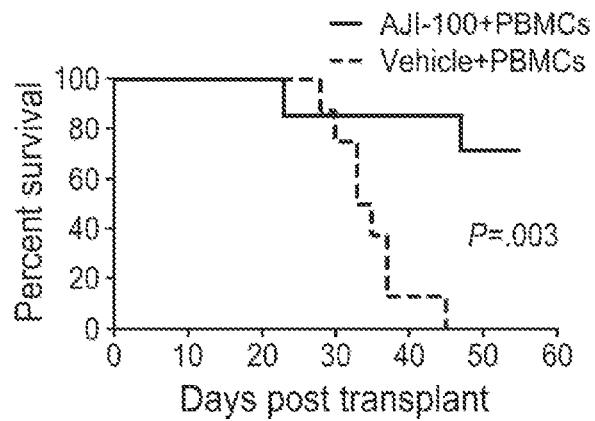
Figure 7G:
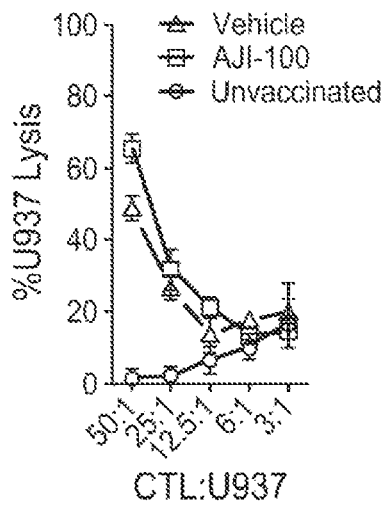
Figure 7H:
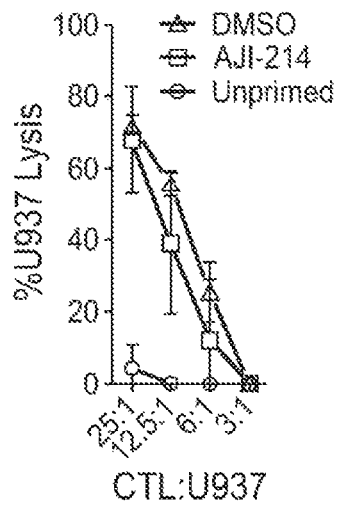

To study the concept of dual Aurora kinase A/JAK2 inhibition as GVHD prevention, mice were treated with bisanilinopyrimidine (II) at 50 mg/kg daily i.p. or vehicle control from day 0 to day +14. JAK2 inhibition was confirmed in vitro, where human T-cells stimulated with IL-6 expressed less STAT3 phosphorylation with bisanilinopyrimidine (II) exposure compared with DMSO (FIG. 7B). Harvested human T-cells from the mice at day +14 showed less H3 ser10 phosphorylation with bisanilinopyrimidine (II) compared to vehicle, confirming Aurora inhibition (FIG. 7C). The vehicle control treated mice developed acute xenogeneic GVHD (including fur loss, skin changes, weight loss, and kyphosis) by the third week of the transplant with a median survival of 34 days (FIGS. 7D-7E). The overall survival of the bisanilinopyrimidine (II)-treated mice was 71.4% during the 56 days of observation, while none of the vehicle-treated mice survived past day +45 (FIG. 7F). The average GVHD clinical scores were <2 among the surviving bisanilinopyrimidine (II)-treated mice at day +56 (FIG. 7E), where 60% showed limited fur/skin changes without significant weight loss (FIGS. 7D-7E). Conversely, bisanilinopyrimidine (II) and vehicle treated mice both facilitated the generation of U937-specific CTL in vivo and retained similar anti-tumor killing in vitro (FIG. 7G). It was confirmed that the bisanilinopyrimidine (I) analogue similarly allowed for CTL generation in vitro, and that CD8$^+$ CTL remained functional in tumor lysis assays against U937 targets (FIG. 7H).

Figure 8A:
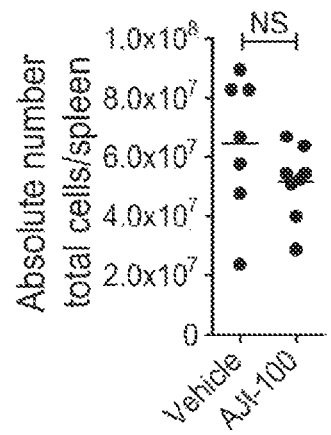
Figure 8B:
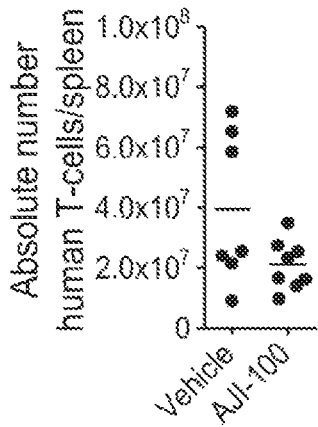
Figure 8C:
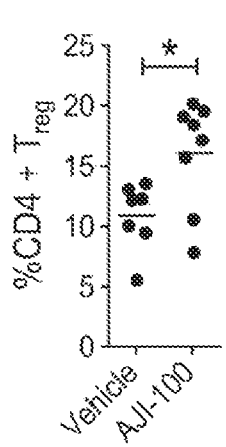
Figure 8D:
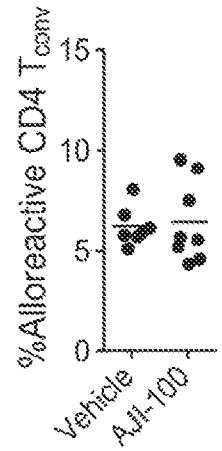
Figure 8E:
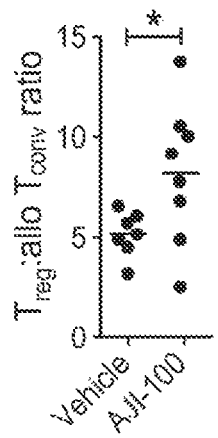

The absolute number of total spleen cells and human CD3$^+$ T-cells within the spleens were similar among vehicle- versus bisanilinopyrimidine (II)-treated mice (FIGS. 8A-8B). bisanilinopyrimidine (II) significantly increased the relative amount of human T$_{regs}$ in the spleen, while the percentage of CD4$^+$ alloreactive T$_{conv}$ was similar among both groups of transplanted mice (FIGS. 8C-8G). As such, bisanilinopyrimidine (II) significantly increased the ratio of human T$_{reg}$ to CD4$^+$ alloreactive T$_{conv}$ in the recipient spleens, compared with vehicle (FIG. 8E). GVHD pathology at day +14 was limited to the liver, where bisanilinopyrimidine (II) dramatically reduced human T-cell invasion (FIGS. 8H-8J). T$_{reg}$ frequency in the liver was similar among both treatment groups, however (FIG. 8K).

T-cell costimulation and cytokine activation independently contribute to GVHD, but control of donor allo-responses is incomplete when targeting either pathway alone. It has been disclosed herein that GVHD prevention with intact GVL can be accomplished by dual inhibition of Aurora kinase A and JAK2, respectively attenuating CD28 costimulation and IL-6-mediated signal transduction. Concurrent blockade of Aurora kinase A and JAK2 yields synergistic immune suppression over human allogeneic T-cells in vitro, preserves iT$_{reg}$ differentiation, and significantly enhances iT$_{reg}$ suppressive potency. These characteristics are distinct from CNI-based GVHD prophylaxis, which abrogates TCR function and indiscriminately suppresses donor T-cells. The lack of selectivity by CNIs results in a failure to achieve donor immune tolerance toward the host and negates the GVL potential of the allograft. Selective targeting of Aurora kinase A and JAK2 signal transduction controls fundamental aspects of T-cell allo-activation, without ceding TCR function required by T$_{regs}$ and anti-tumor CTL.

Blockade of Aurora kinase A or JAK2 induces pathway-specific effects on developing iT$_{reg}$ and T$_H$17. It was observed that the dual pathway inhibitor, bisanilinopyrimidine (I), significantly increased the suppressive potency of allo-antigen specific iT$_{reg}$. The data supports that the enhanced iT$_{reg}$ potency is largely a function of Aurora kinase A inhibition. While JAK2 blockade with TG101348 improved iT$_{reg}$ function compared with DMSO, iT$_{regs}$ previously exposed to alisertib profoundly eliminated T$_{conv}$ proliferation. On the other hand, alisertib was unable to prevent RORgammaT expression in naïve CD4$^+$ T-cells responding to allo-antigen unlike AJI-214 or TG101348. Given that IL-6 receptor signal transduction facilitates T$_H$17 development, the data confirm that JAK2 blockade with bisanilinopyrimidine (I) or TG101348 significantly restrains $T_H17$ differentiation.

Modes of $T_{reg}$ suppression to understand how bisanilinopyrimidine (I) improved $iT_{reg}$ suppressive potency was investigated. $iT_{reg}$ production of the anti-inflammatory cytokines, IL-10 and TGF-beta, where comparable among bisanilinopyrimidine (I)- and DMSO-treated $iT_{regs}$. Moreover, $iT_{reg}$ expression of CTLA4 and LAGS was similar among each experimental condition. Interestingly, it was identified that bisanilinopyrimidine (I) significantly increased the surface density of CD39 expressed on the $iT_{regs}$. CD39 is an ectonucleotidase that hydrolyzes extracellular ATP and reduces T-cell activation (M. Vukmanovic-Stejic et al., The kinetics of $CD4^+Foxp3^+$ T cell accumulation during a human cutaneous antigen-specific memory response in vivo. *The J. Clinical Invest.* 118, 3639 (2008)).

$CD39^+$ $T_{regs}$ correlate with clinical outcomes in autoimmune diseases (R. S. Peres et al., Low expression of CD39 on regulatory T cells as a biomarker for resistance to methotrexate therapy in rheumatoid arthritis. *Proc. Natl. Acad. Sci. USA* 112, 2509 (2015); A. Thiolat et al., Interleukin-6 receptor blockade enhances $CD39^+$ regulatory T cell development in rheumatoid arthritis and in experimental arthritis. *Arthritis & Rheumatol.* 66, 273 (2014)). A decrease in $CD39^+$ $T_{regs}$ is associated with methotrexate-failure among rheumatoid arthritis (RA) patients. Alternatively, IL-6 neutralization with tocilizumab increases $CD39^+$ $T_{regs}$ in a similar group of RA patients (38). It was verified that bisanilinopyrimidine (I)-treated $iT_{reg}$ degraded extracellular ATP more efficiently than those exposed to DMSO. This response was impaired by blocking CD39 with the inhibitor ARL67156. Additionally, neutralization of CD39 activity significantly attenuated the immune suppressive effect of dual Aurora kinase A/JAK2 inhibition in $nT_{reg}$ depleted alloMLRs. This data supports that increased CD39 expression is relevant to the enhanced $iT_{reg}$ function mediated by bisanilinopyrimidine (I).

While inhibition of Aurora kinase A or JAK2 activity individually suppressed human Tcell proliferation in alloMLRs, synergy was achieved with simultaneous blockade of both signal transduction pathways. The bi-specific inhibitors, bisanilinopyrimidine (II) and bisanilinopyrimidine (I), demonstrated potent single agent activity at nanomolar concentrations. As published, bisanilinopyrimidine (II) and bisanilinopyrimidine (I) exhibit similar activity against Aurora kinase A and JAK2. Bisanilinopyrimidine (II) differs from bisanilinopyrimidine (I) by a single chlorine to hydrogen substitution on its phenyl ring to facilitate in vivo solubility for mouse studies, but the compounds are otherwise chemically and functionally similar.

Target inhibition was confirmed as bisanilinopyrimidine (II) and bisanilinopyrimidine (I) significantly reduced the phosphorylation of both STAT5 and H3 ser10 in human T-cells. Conversely, combined Aurora kinase A/JAK2 blockade permitted IL-2-induced STAT5 activation in T-cells, compared with resting, unstimulated controls. The selective inhibition of Aurora kinase A and JAK2 paired with preserved common gamma chain cytokine signaling establishes a platform to control alloreactivity while maintaining antigen-specific $T_{reg}$ and CTL responses. Accordingly, it was observed that bisanilinopyrimidine (II) significantly reduces GVHD, increases the proportion of $T_{reg}$ to allo $T_{conv}$, and preserves CTL generation and anti-tumor activity. CNI-free GVHD prophylaxis is an important concept in improving patient outcomes after clinical transplantation. The challenges of CNI-based GVHD prevention are clear; as CNIs offer incomplete protection from severe GVHD and render the donor immune system poorly equipped to counter post-transplant relapse. Given that targeting Aurora kinase A and JAK2 selectively eliminates alloreactive $T_{conv}$ while sparing $T_{regs}$ and tumor-specific CTL, the novel concept described here may represent a translatable CNI-free approach at GVHD prevention. A limited number of CNI-free GVHD prophylaxis strategies currently exist, and include T-cell depletion of the allograft (M. C. Pasquini et al., Comparative outcomes of donor graft $CD34^+$ selection and immune suppressive therapy as graft-versus-host disease prophylaxis for patients with acute myeloid leukemia in complete remission undergoing HLA-matched sibling allogeneic hematopoietic cell transplantation. *J. Clinical Oncol.* 30, 3194 (2012)) or the use of post-transplant cyclophosphamide (C. G. Kanakry et al., Single-agent GVHD prophylaxis with posttransplantation cyclophosphamide after myeloablative, HLA-matched BMT for AML, ALL, and MDS. *Blood* 124, 3817 (2014)). The bispecific inhibitor, bisanilinopyrimidine (II), is an attractive alternative as it does not require ex vivo allograft modification or the need to expose freshly infused donor stem cells to potent alkylators. As such, further investigation of dual Aurora kinase A/JAK2 inhibition is merited to promote selective control over donor immune responses after alloHCT.

Study 2:

Synergistic Immunosuppression is Attainable with Combined Inhibition of Aurora Kinase a and JAK2.

Figure 9A:
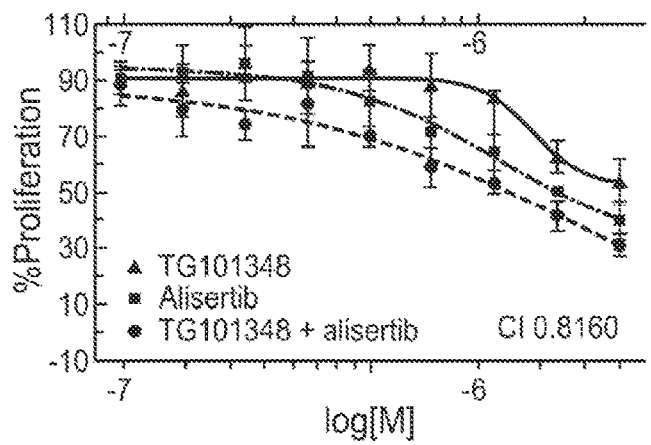
FIGS. 9A-9H show synergistic immune suppression with combined inhibition of Aurora kinase A and JAK2.
Figure 9B:
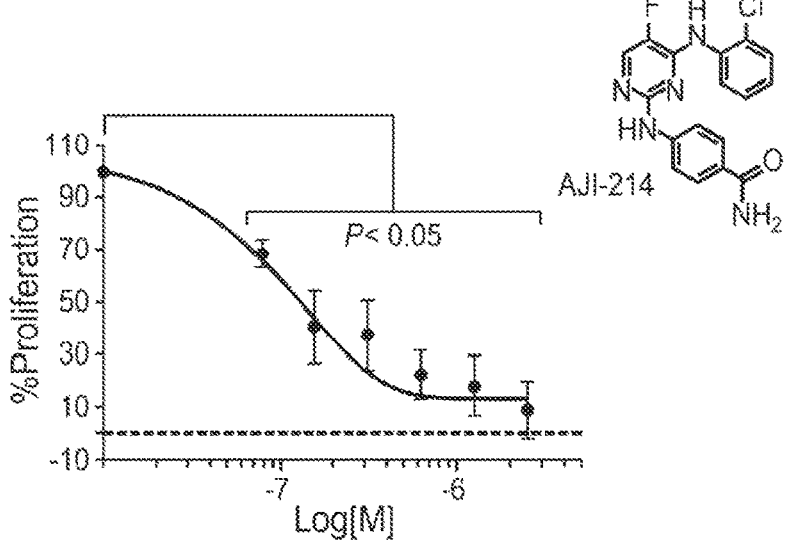
Figure 9C:
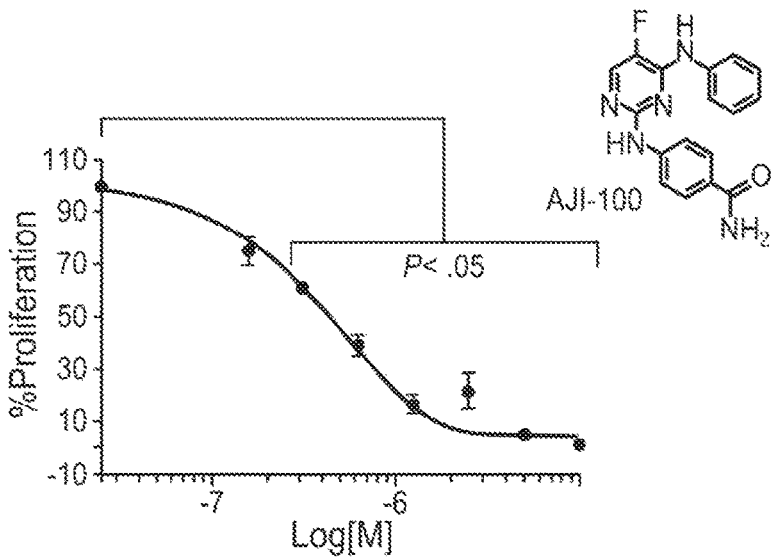
Figure 9D:
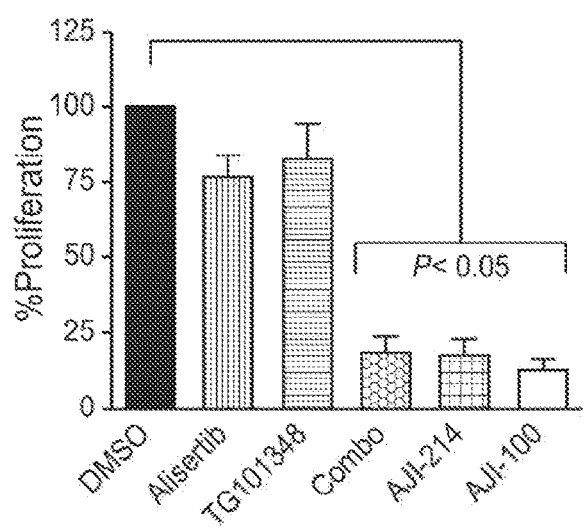
Figure 9E:
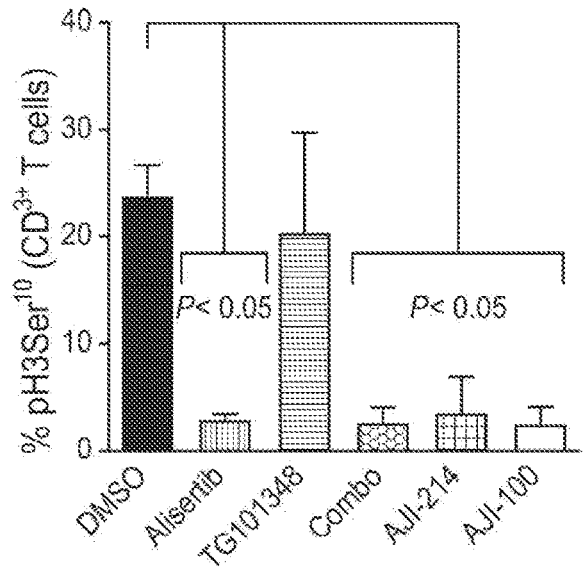
Figure 9F:
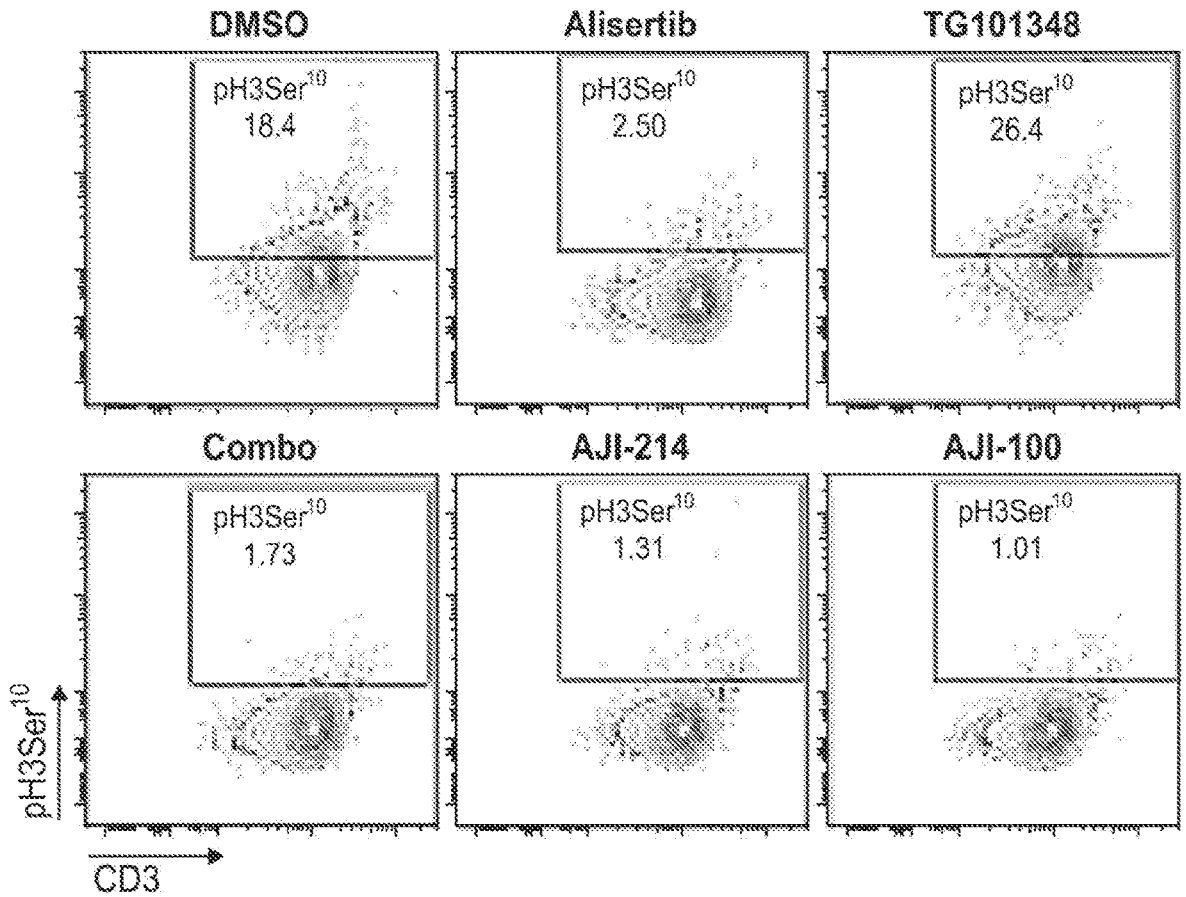
Figure 9G:
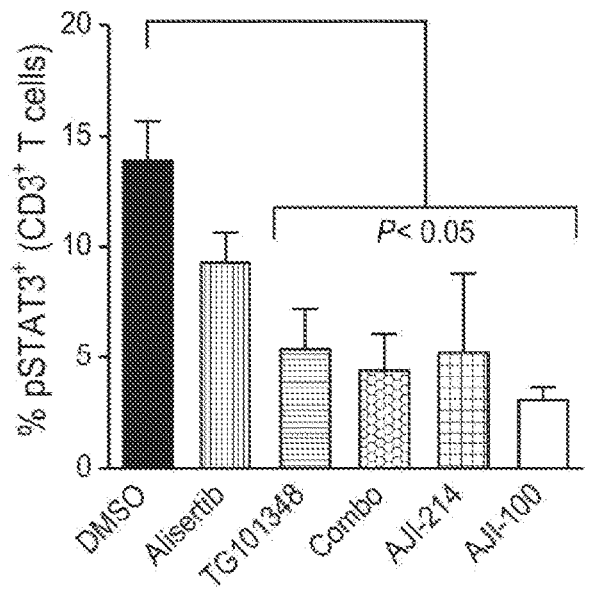
Figure 9H:
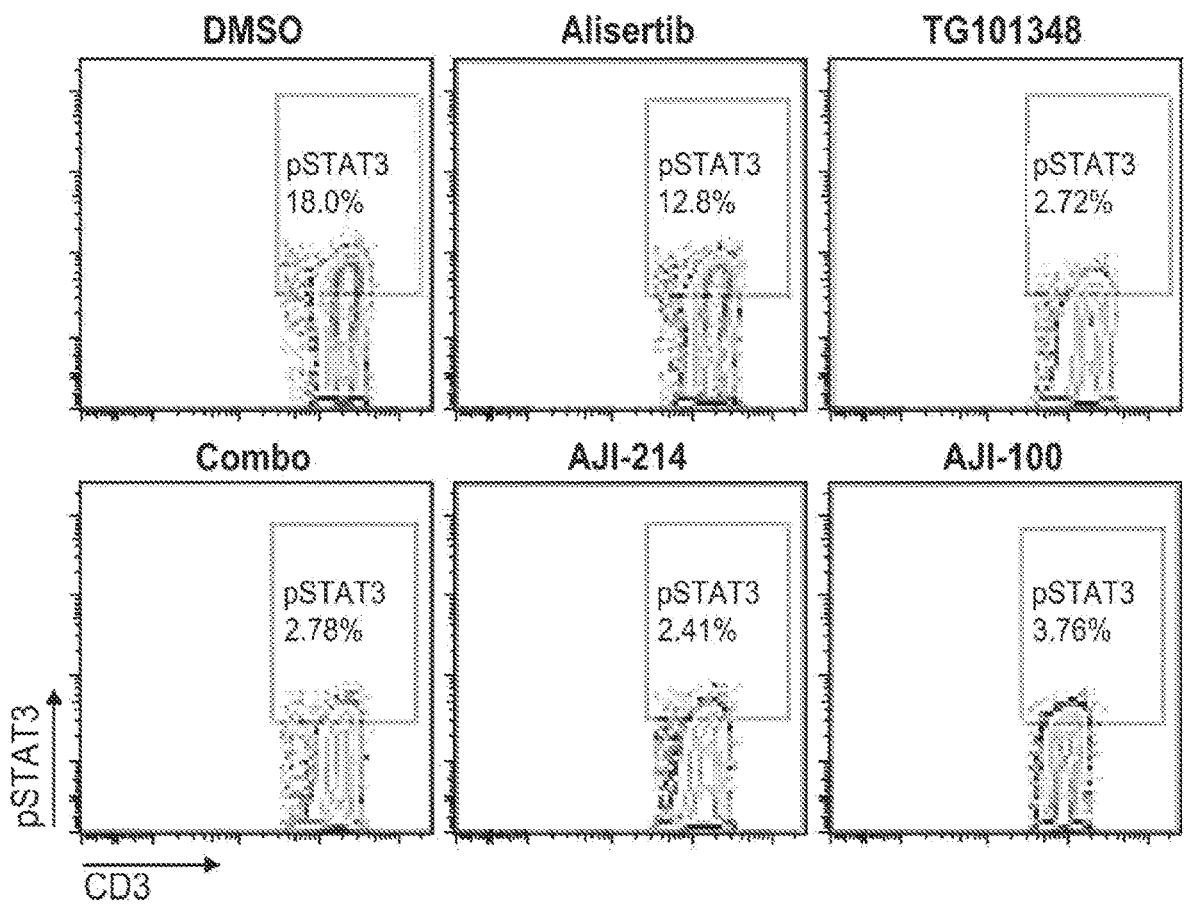

Allogeneic mixed leukocyte reactions (alloMLRs) are standard assays used to assess human T cell proliferation against polyclonal or antigen-specific stimuli. In alloMLRs consisting of human T cells and allogeneicmonocyte-derived dendritic cells (DCs), the JAK2 inhibitor TG101348 reduced alloreactive T cell proliferation at concentrations of 350 nM and greater as previously reported (FIG. 9A). The Aurora kinase A inhibitor alisertib suppressed the proliferative response of T cells in alloMLRs with a median inhibitory concentration ($IC_{50}$) of 10 mM (FIG. 9A). Synergistic suppression of T cells allostimulated by DCs was achieved when TG101348 and alisertib were added together at a ratio of 1:5, respectively, with a calculated combination index (CI) of <1 using the Chou-Talalay method (FIG. 9A). The observed $IC_{50}$ of the combination correlated with 350 nM TG101348 and 1.75 mM alisertib (FIG. 9A). The chemical analogs AJI-214 and AJI-100 were designed and synthesized at the Moffitt Cancer Center and shown to inhibit Aurora kinase A and JAK2 with similar potency. AJI-100 differs from AJI-214 by a single chlorine to hydrogen substitution at the ortho position of its phenyl ring, enhancing its solubility, hence its preferred use in vivo (FIGS. 9B-9C). Because AJI-100 is tolerated in mouse models, a kinase target screen was performed on AJI-100 to verify its activity against Aurora kinase A and JAK2 among a panel of 140 kinases. Aurora kinase A and JAK2 were among the top three kinases inhibited by AJI-100. It was found that AJI-100 also inhibits 5' AMP activated protein kinase (AMPK) and exhibits slightly more potent suppression of Aurora kinase B than alisertib. AJI-214 and AJI-100 exerted significant suppression of T cells in alloMLRs, with single-agent efficacy at nanomolar concentrations (P<0.05; FIGS. 9B-9C). Moreover, the AJI analogs suppressed alloreactive T cell proliferation similar to the potency of alisertib (1.75 mM) and TG101348 (350 nM) combined (FIG. 9D). AJI-214 and AJI-100 (750 nM for each) also exhibited similar target inhibition of Aurora kinase A and JAK2 signal transduction in human T cells, reducing the phosphorylation of histone 3 serine 10) (pH3Ser[10] and STAT3 (pSTAT3) Y705, respectively (FIGS. 9E-9H). As expected, alisertib only inhibited pH3Ser$^{10}$ (FIGS. 9E-9F), and TG101348 only inhibited pSTAT3 (FIGS. 9G-9H).

Figure 10A:
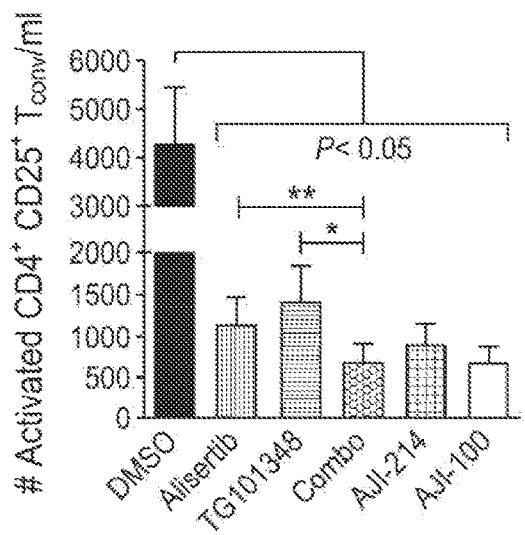
FIGS. 10A-10H show immunosuppressive effect of Aurora kinase A/JAK2 blockade on responder $T_{conv}$ and $T_H$ subsets.
Figure 10B:
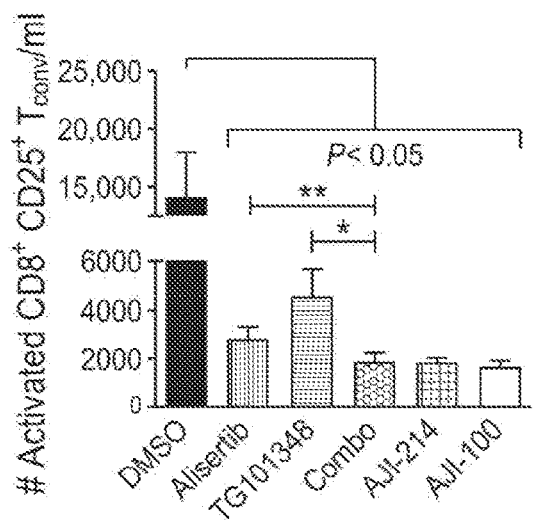
Figure 10C:
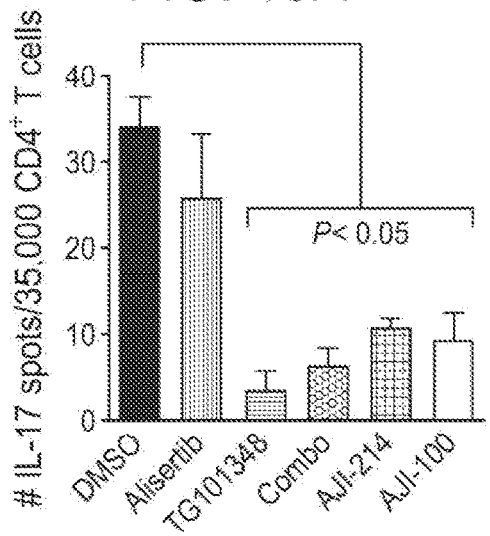
Figure 10D:
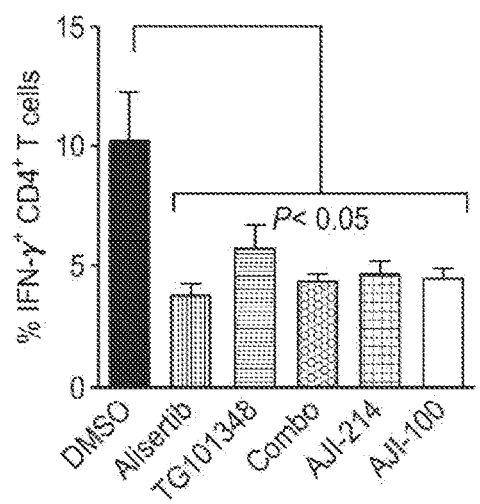
Figure 10E:
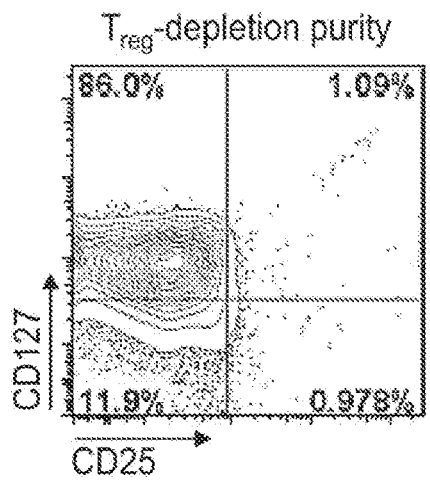
Figure 10F:
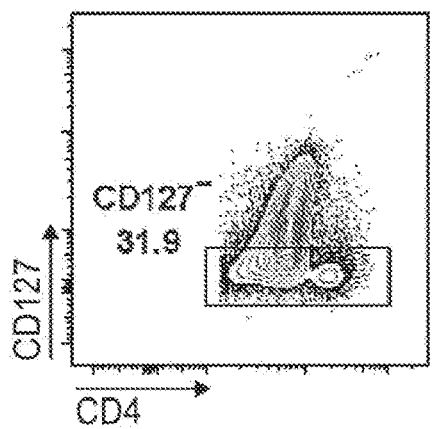
Figure 10F:
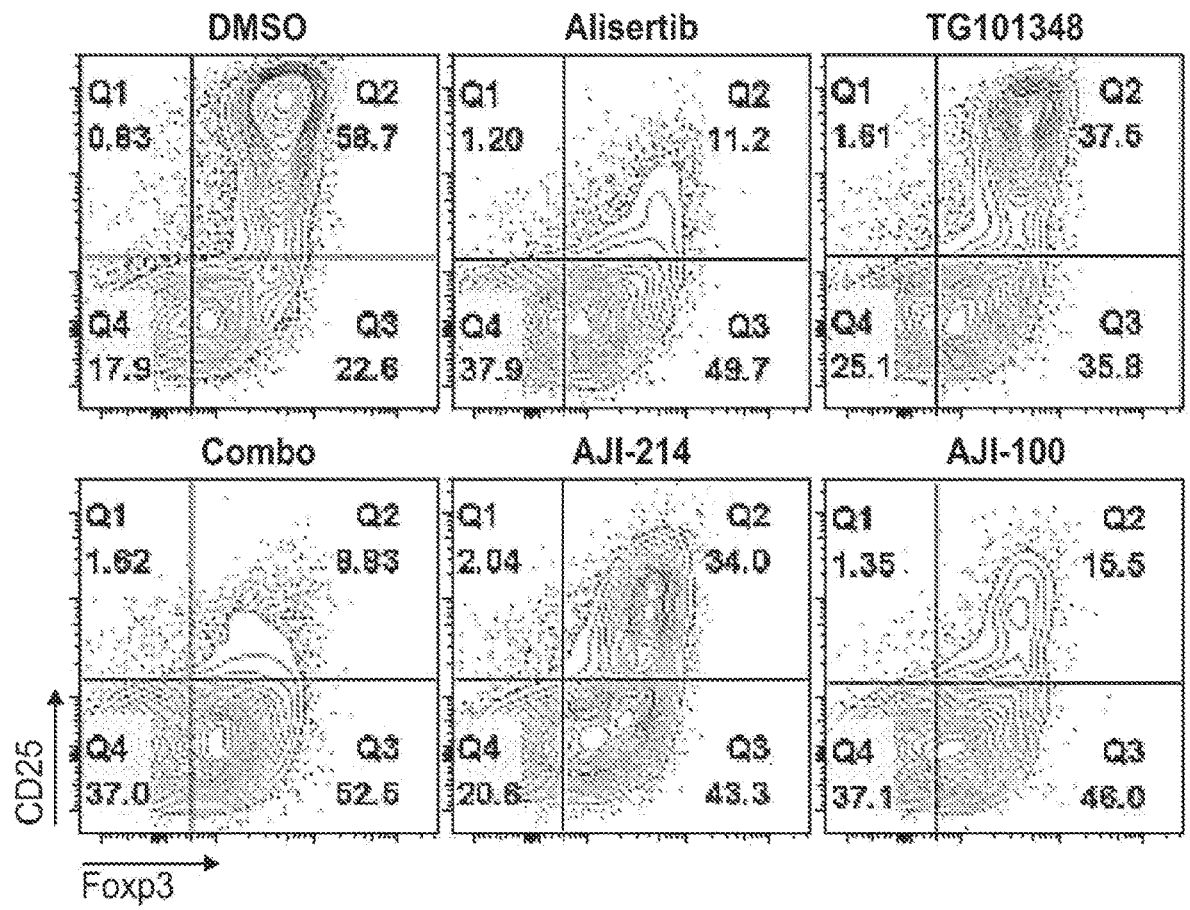
Figure 10G:
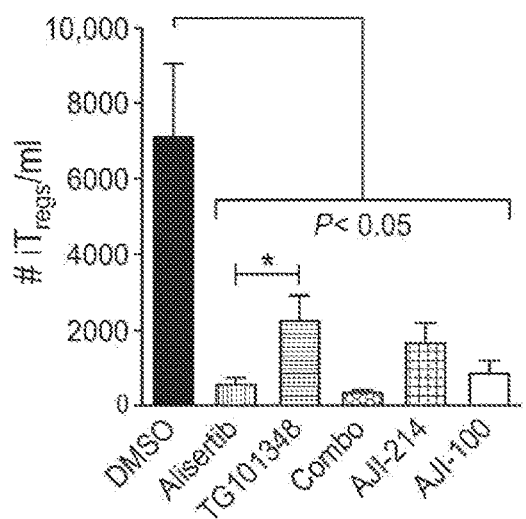
Figure 10H:
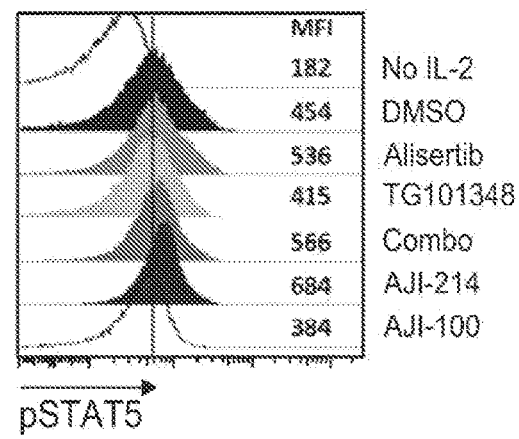

Concurrent Blockade of Aurora Kinase A and JAK2 is Immunosuppressive and Permits the Differentiation of Inducible $T_{reg}$ DMSO, alisertib, TG101348, a combination of alisertib and TG101348, AJI-214, or AJI-100 was added to allogeneic cocultures of DC-stimulated T cells. Activated CD4$^+$ $T_{conv}$ were identified as coexpressing CD25 and CD127, and the latter assisted in excluding $T_{regs}$ from the analysis. CD25 expression alone was used to identify activated CD8$^+$ $T_{conv}$. Although all inhibitors suppressed the activated $T_{conv}$ compared to DMSO, combined inhibition of Aurora A and JAK2 offered greater immunosuppression than either alisertib (P=0.007, FIG. 10A; P=0.002, FIG. 10B) or TG101348 alone (P=0.02, FIG. 10A; P=0.02, FIG. 10B). To quantify the effect of Aurora A/JAK2 blockade on $T_H17$, IL-17 ELISPOTs was performed using DC-stimulated, purified CD4$^+$ T cells in the presence of the compounds or DMSO. As predicted by the effect of each inhibitor on STAT3 phosphorylation, the JAK2-targeting compounds significantly reduced $T_H17$, whereas alisertib had no effect (P<0.05; FIG. 10C). All of the inhibitors significantly decreased the frequency of interferon-γ$^+$ (IFN-γ$^+$) $T_H1$ T cells among treated allogeneic cocultures (P<0.05; FIG. 10D). However, dual blockade of Aurora A and JAK2 did not offer increased suppression of $T_H1$ compared to either inhibitor alone (FIG. 10D). Given that inhibition of Aurora A and JAK2 significantly reduced alloreactive $T_{conv}$, $T_H1$, and $T_H17$ cells, the effects of dual blockade on inducible $T_{reg}$ (i$T_{reg}$) differentiation was then studied. Naïve CD4$^+$ T cells (>99% pure; FIG. 10E) were depleted of natural $T_{regs}$ and stimulated with allogeneic DCs for 5 days in the presence of DMSO, alisertib, TG101348, a combination of alisertib and TG101348, AJI-214, or AJI-100. The i$T_{regs}$ were identified as CD4$^+$, CD127$^−$, CD25$^+$, and Foxp3$^+$. i$T_{reg}$ conversion from naïve CD4$^+$ precursors was variably reduced by all of the compounds compared to DMSO (FIGS. 10F-10G), and Aurora A inhibition appeared to exert greater i$T_{reg}$ impairment than JAK2 inhibition (FIG. 10G). In contrast, IL-2-induced STAT5 phosphorylation, which is required for $T_{reg}$ development, remained intact among T cells treated with alisertib, TG101348, a combination of alisertib and TG101348, or the AJI analogs compared to DMSO (FIG. 10H).

Dual Inhibition of Aurora Kinase a and JAK2 Supports Potent CD39$^+$ i$T_{reg}$

Figure 11A:
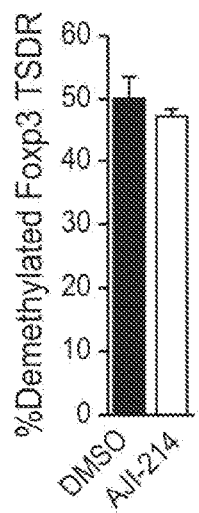
FIGS. 11A-11C show combined inhibition of Aurora kinase A and JAK2 enhances antigen-specific $iT_{reg}$-suppressive potency.
Figure 11B:
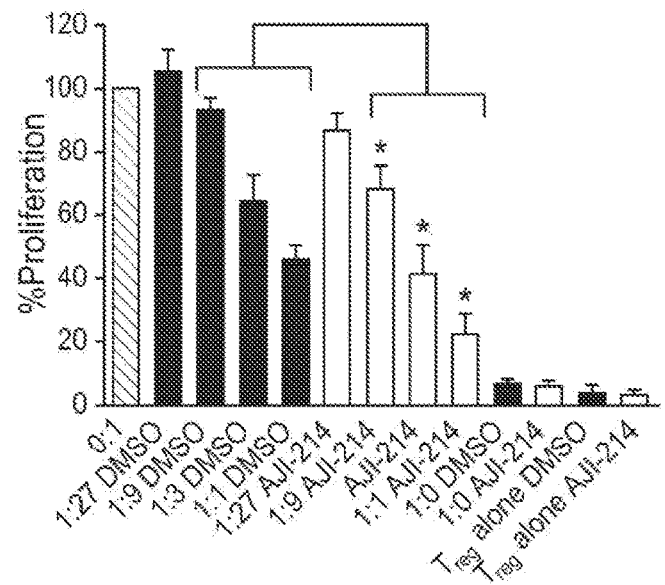
Figure 11C:
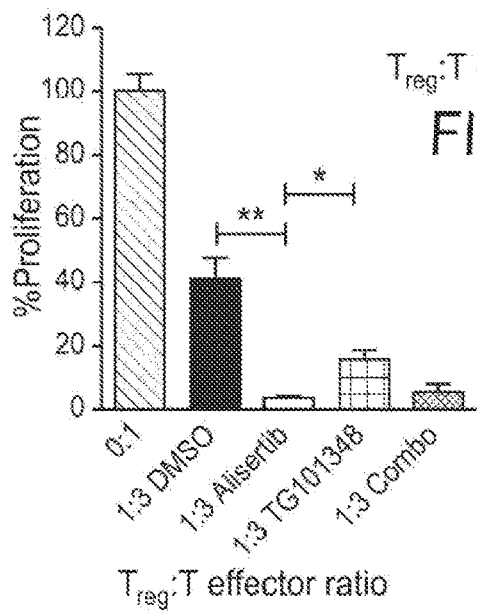
Figures 12A, 12B:
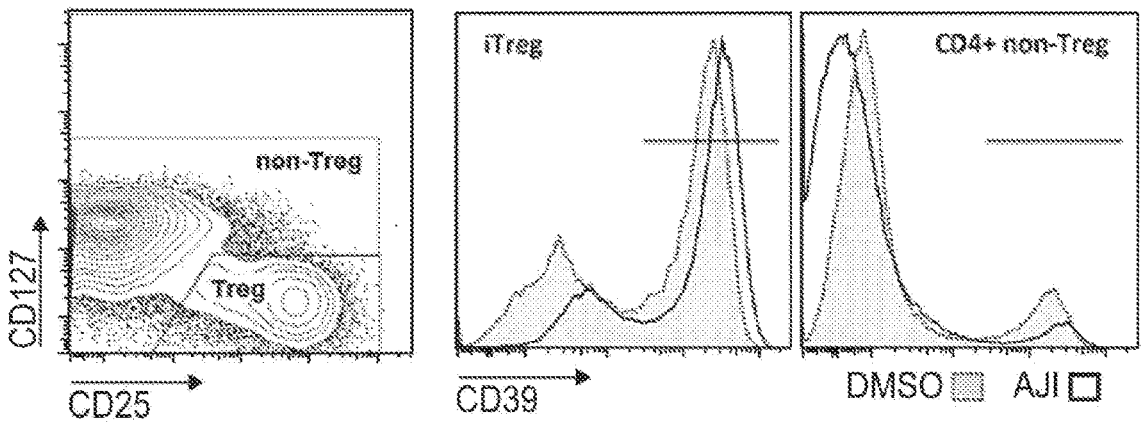
FIGS. 12A-12J show targeting Aurora kinase A and JAK2 increases CD39 expression and ATP scavenging among $iT_{reg}$.
Figure 12C:
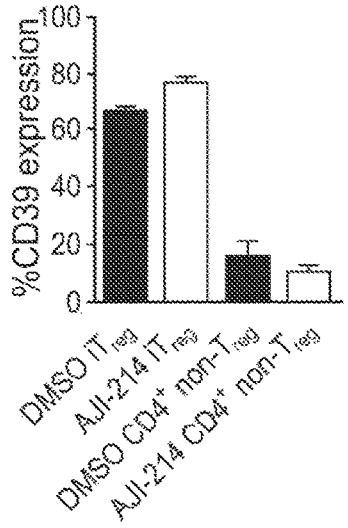
Figure 12D:
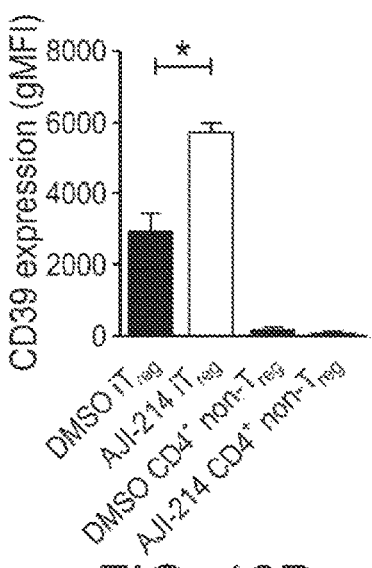
Figure 12E:
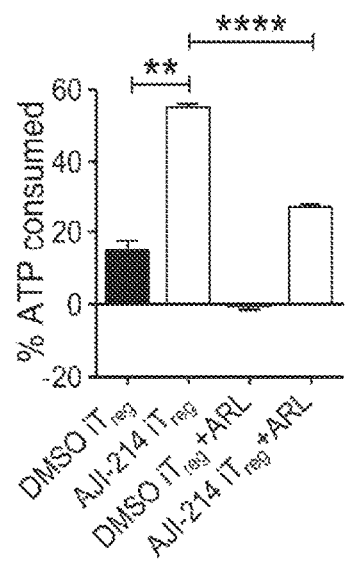
Figure 12F:
Figure 12G:
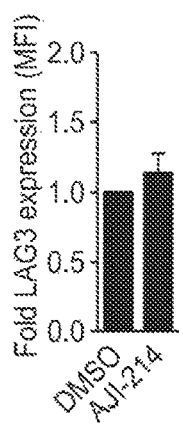
Figure 12H:
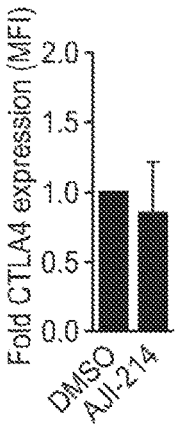
Figure 12I:
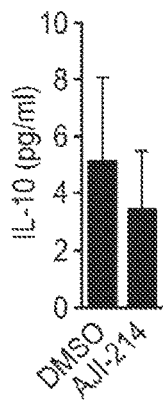
Figure 12J:
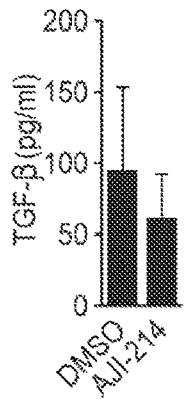

AJI-214 and AJI-100 were confirmed to exhibit identical suppressive potency in regard to Aurora A and JAK2 signal transduction and human T cell proliferation assays. Therefore, AJI-214 was used as the representative bispecific analog for additional i$T_{reg}$-based in vitro mechanistic tests. Given that i$T_{regs}$ are derived from phenotypically plastic naïve CD4$^+$ T cells, it was confirmed that demethylated Foxp3 $T_{reg}$-specific demethylated region (TSDR) was similar among AJI-214-exposed and DMSO-exposed i$T_{regs}$ (FIG. 11A). To study the influence of dual pathway inhibition on i$T_{reg}$-suppressive function, AJI-214-treated or DMSO-treated i$T_{reg}$ were cultured with autologous T cells targeting fresh allogeneic DCs. The AJI-214-treated i$T_{regs}$ demonstrated intact suppressive function, and its potency was significantly increased by about 30% compared to DMSO-treated i$T_{regs}$ (P=0.018; FIG. 11B). How Aurora kinase A versus JAK2 blockade contributed to this enhanced suppression by the i$T_{regs}$ was explored. Antigen-specific i$T_{regs}$ were generated from CD25-depleted CD4$^+$ T cells in the presence of alisertib, TG101348, a combination of alisertib and TG101348, or DMSO. Aurora kinase A inhibition with alisertib demonstrated superior suppressive capacity compared with either DMSO-exposed (P=0.03) or TG101348-exposed (P=0.04) i$T_{reg}$ (FIG. 11C). The combination of alisertib with TG101348 was similar to alisertib alone (FIG. 11C). The mechanism supporting the increased i$T_{reg}$ function observed with AJI-214 was investigated. A significant increase in the cell surface density of CD39, an ectonucleotidase that hydrolyzes adenosine triphosphate (ATP), was identified among the AJI-214-exposed i$T_{reg}$ compared with DMSO controls (P=0.045; FIGS. 12A-12D). As reported by others, CD39 expression on non-$T_{reg}$ CD4$^+$ T cells was minimal (FIGS. 12B-12D). The higher CD39 cell surface density was confirmed among the AJI-214-treated i$T_{regs}$ resulted in improved scavenging of extracellular ATP, compared to DMSO-treated i$T_{regs}$ (FIG. 12E). The enhanced hydrolysis of ATP by the AJI-214-treated i$T_{regs}$ was also significantly impaired by blocking the CD39 enzyme with ARL67156 (P<0.0001; FIG. 12E). To determine the influence of CD39$^+$ i$T_{reg}$ in the overall efficacy of dual Aurora A/JAK2 blockade, ARL67156 was added to alloMLRs consisting of natural $T_{reg}$-depleted CD4$^+$ T cell responders with AJI-214 or DMSO. This eliminated potential interference from CD39$^+$ natural $T_{reg}$ within the allogeneic coculture and ensured that the only $T_{regs}$ present in the system were induced. Moreover, ARL67156 would primarily affect the i$T_{reg}$ as $T_{conv}$ express negligible amounts of CD39. CD39 blockade significantly weakened the T cell inhibition by AJI-214 (P=0.037; FIG. 12F), supporting that CD39$^+$ i$T_{regs}$ contribute to the immunosuppressive effects of AJI-214. With regard to other modes of i$T_{reg}$ suppression, no difference in their expression of LAG3 and CTLA4 or production of IL-10 or transforming growth factor-β (TGF-β) was found after exposure to AJI-214 or DMSO (FIG. 12G-12J).

Figure 13A:
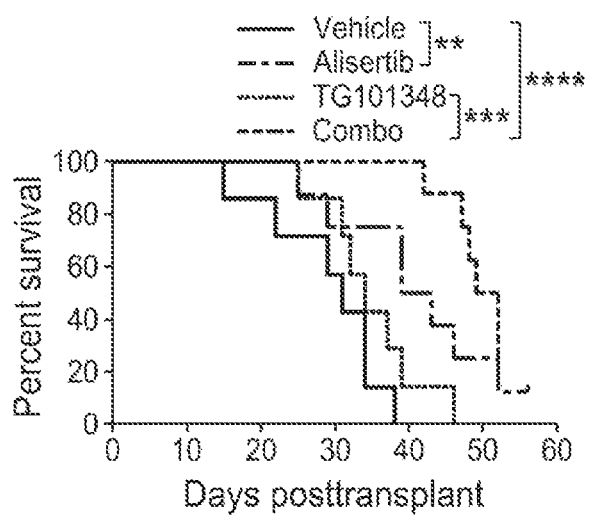
Figure 13B:
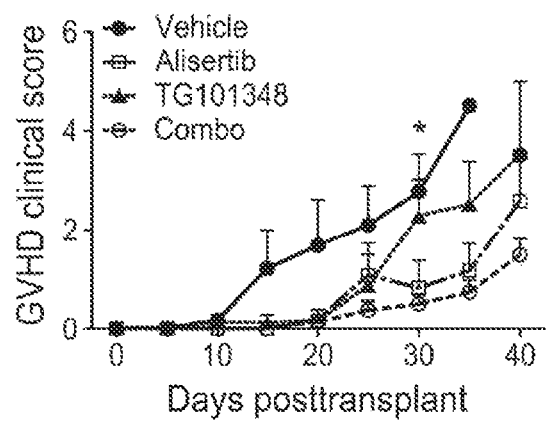
Figure 13C:
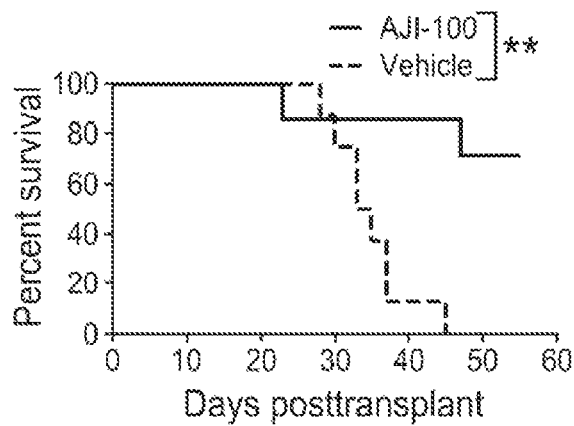
Figure 13D:
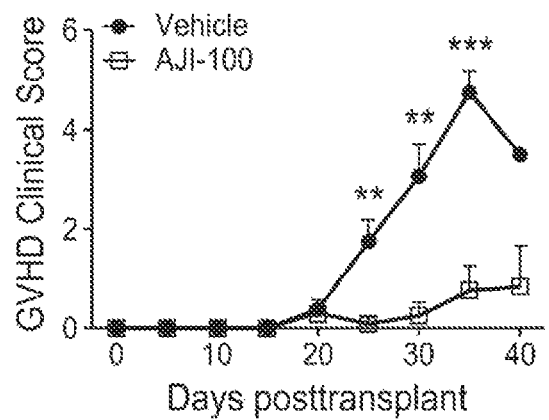

Targeting Aurora Kinase A and JAK2 Reduces Xenogeneic GVHD and Preserves the Generation Antitumor CTL A xenogeneic GVHD model was used to investigate the in vivo efficacy of dual Aurora kinase A/JAK2 blockade to specifically evaluate effects on human immune responses. Recipient NOD (nonobese diabetic) scid g (NSG) mice were transplanted with human peripheral blood mononuclear cells (PBMCs) (30×10$^6$ cells) intraperitoneally (ip) on day 0. Independent donors were used for each experiment. Whether combining individual inhibitors of Aurora A and JAK2 prevented acute xenogeneic GVHD was tested. Mice received alisertib (30 mg/kg daily), TG101348 (45 mg/kg twice a day), a combination of alisertib and TG101348, or methylcellulose vehicle from days 0 to +14 by oral gavage. The drug combination significantly delayed the onset and severity of GVHD, compared to vehicle or TG101348 alone (P<0.0001 and P=0.0001, respectively; FIGS. 13A-13B). There was also a suggestion toward an improved median survival with the drug combination compared to alisertib (50.5 versus 41 days; P=not significant). The bispecific inhibitor AJI-100 was used to test the in vivo efficacy of single agent blockade of Aurora A and JAK2 as GVHD prevention. As demonstrated, AJI-100 offers identical on-target inhibition and immunosuppressive properties as AJI-214 but exhibits superior bioavailability. Compared to using the combination of alisertib and TG101348, AJI-100 had the advantage of being given once daily by intraperitoneal injection and avoided the need for sustained gavage dosing. Additionally, the single bispecific compound provided a pharmacologically cleaner approach by eliminating the variability in pharmacokinetics between the two drugs in combination. The recipient mice were transplanted with human cell as described. AJI-100 (50 mg/kg) or vehicle control was administered daily by intraperitoneal injection from days 0 to +14. AJI-100 significantly improved the overall survival of the mice and reduced the severity of GVHD, compared to vehicle control (P=0.003; FIGS. 13C-13D). On target inhibition of Aurora A and JAK2 was confirmed among human T cells harvested from recipient spleens at day +14. AJI-100 significantly reduced the amount of pH3Ser10$^+$ and pSTAT3$^+$ T cells, respectively (P=0.027 and P=0.0098, respectively; FIGS. 13E-13F). An established method was used to generate human antitumor CTL in vivo and then test their specific killing. CD8$^+$ CTLs were generated in xenotransplanted mice receiving AJI-100 or vehicle control, where an inoculum of irradiated U937 cells was administered on day 0 and day +7. Unvaccinated, xenotransplanted mice served as negative control. Despite its immunosuppressive activity, AJI-100 did not inhibit CTL generation because CD8$^+$ CTL from AJI-100-treated and vehicle-treated mice demonstrated similarly enhanced killing capacity against U937 targets in vitro, compared to unvaccinated controls (FIG. 13G). These data support that although AJI-100 significantly reduces GVHD, it also preserves antitumor CTL responses.

Figure 14E:
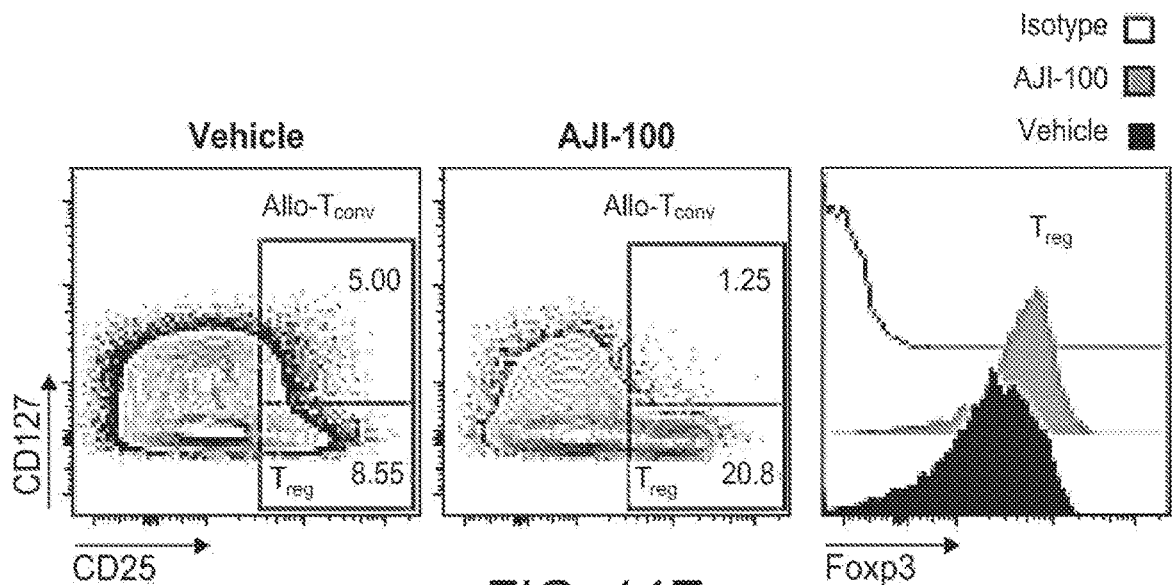
Figure 14F:
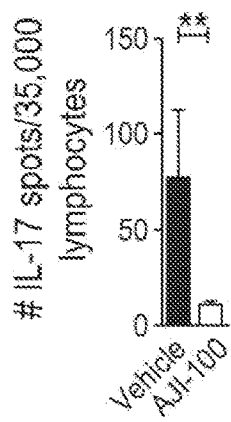
Figure 14G:
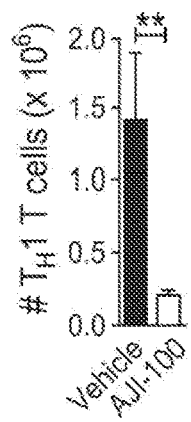
Figure 14H:
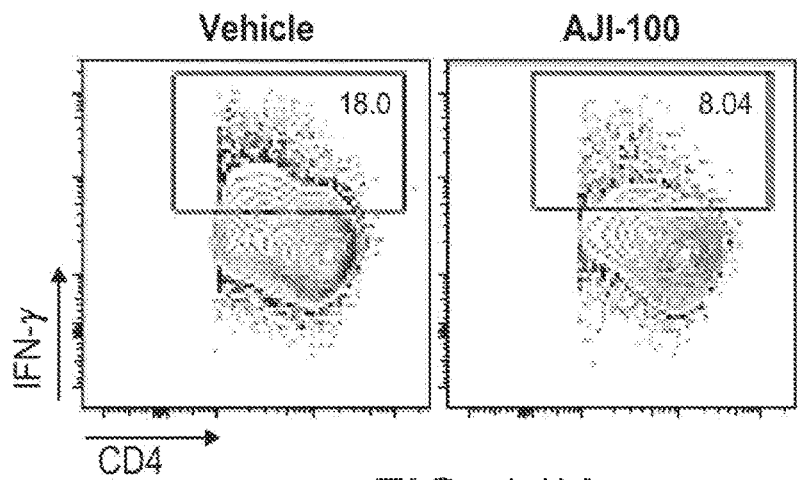

AJI-100 Significantly Increases the Ratio of $T_{reg}$ to Activated $T_{conv}$ while Eliminating $T_H17$ and $T_H1$ T Cells Similar to its activity in vitro, AJI-100 suppressed the in vivo expansion of human T cells in the xenotransplanted mice. The absolute number of total CD4$^+$ T cells (P<0.0001), $T_{regs}$ (P=0.001), and activated CD4$^+$ $T_{conv}$ (P<0.0001) from recipient spleens at day +14 was all significantly reduced by AJI-100 compared to vehicle (FIGS. 14A-E). Activated $T_{conv}$ were proportionally more reduced by AJI-100 compared to $T_{reg}$ (FIGS. 14B-14C). Therefore, the ratio of $T_{reg}$ to activated $T_{conv}$ was significantly increased among mice treated with AJI-100 compared to vehicle (P=0.034; FIG. 14D). AJI-100 also significantly reduced the amount of spleen-resident human $T_H17$ and $T_H1$ T cells, compared to vehicle (P=0.002 for both; FIGS. 14F-14H). AJI-100 also exerted a suppressive effect on CD8$^+$ T cell and CD19$^+$ B cell reconstitution as determined by absolute numbers compared to vehicle. However, the frequencies of CD4$^+$ and CD8$^+$ T cells and CD19$^+$ B cells were similar among AJI-100-treated and vehicle-treated mice. The primary host target organs affected by GVHD at day +14 in this xenogeneic model were liver and lung. GVHD severity within these organs was significantly reduced by AJI-100, compared to vehicle (P=0.043 and P=0.002, respectively; FIGS. 14I-14K) Immunohistochemistry demonstrated that the number of tissue-infiltrating, human CD3+ T cells in recipient liver and lung was also significantly decreased by AJI-100 treatment (P=0.006 and P=0.002, respectively; FIGS. 14L-14M).

AJI-100 Reduces Xenograft Rejection.

Figures 15A, 15B, 15C:
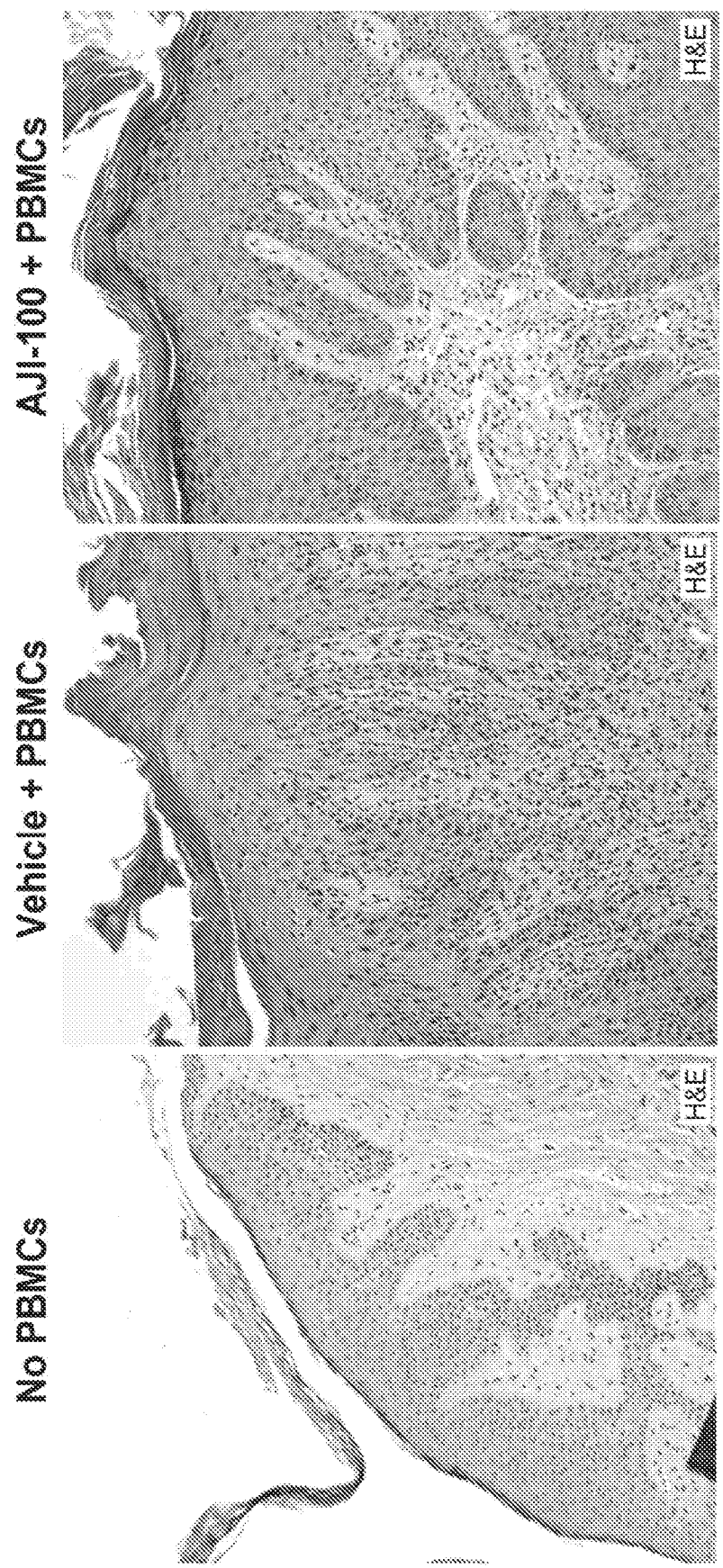
FIGS. 15A-15C are micrographs of representative H&E stained human, xenogenic shin grafts at day +21. Mice were treated with AJI-100. Mice receiving skin alone and no PBMC's (allogeneic peripheral blood mononuclear cells) were considered as non-rejection control (n=1 experiment, 12 mice).

Using the nondiagnostic mastectomy skin from consenting donors, a 1×1 cm skin graft was transplanted onto immunodeficient NSG mice dorsally. After 30 days of healing, 5×10$^6$ peripheral blood mononuclear cells (PBMC) from an HLA-disparate random donor was given by i.p. injection. A cohort of mice only received a skin graft without PBMCs, as negative rejection controls. The transplanted mice were treated with AJI-100 (50 mg/kg), a dual JAK2/Aurora A kinase inhibitor, or vehicle daily by i.p. injection. Mice were humanely euthanized on day +21 to assess human anti-human skin rejection pathology. Representative H&E staining of the skin grafts show normal cutaneous histology in the no PBMC control (per the Bejarano scoring system, *Am J Surg Pathol* 28:670-675, 2004); demonstrated by an obvious dermal-epidermal junction, lack of perivascular or dermal infiltrates, and no lymphocytic exocytosis or hyperkeratosis (grade 0, FIG. 15C). Conversely, skin grafts from the mice who received Vehicle+PBMCs show diffuse lymphocytic infiltration of the dermis with exocytosis, a disrupted dermal-epidermal junction, and hyperkeratosis (grade III, FIG. 15B). Mice that received AJI-100+PBMCs exhibited very little graft damage, with mild dermal infiltration, a normal dermal-epidermal junction, and limited hyperkeratosis (grade I, FIG. 15C).

Results Summary

T cell costimulation and cytokine activation independently contribute to GVHD, but control of donor alloresponses is incomplete when targeting either pathway alone. Here, it is demonstrated that GVHD prevention can be accomplished by dual inhibition of Aurora kinase A and JAK2, attenuating CD28 costimulation and IL-6-mediated signal transduction, respectively, without ablating potential antitumor CTL responses. Concurrent blockade of Aurora kinase A and JAK2 yields synergistic immunosuppression of human allogeneic T cells in vitro, significantly enhances i$T_{reg}$-suppressive potency, and enhances the ratio of $T_{regs}$ to activated $T_{conv}$ in vivo. These characteristics are distinct from CNI-based GVHD prophylaxis, which inhibits TCR function and indiscriminately suppresses donor T cells. The lack of selectivity by CNIs results in a failure to achieve donor immune tolerance toward the host and mitigates the graft-versus-leukemia (GVL) potential of the allograft. Inhibition of Aurora kinase A or JAK2 activity individually suppressed human T cell proliferation in alloMLRs, and synergy was achieved in vitro with simultaneous blockade of both signal transduction pathways. A xenogeneic model was used to study human T cell responses in vivo after Aurora kinase A and JAK2 blockade, understanding that the lack of recipient conditioning does differ from clinical practice in allogeneic HCT. It was shown that alisertib combined with TG101348 significantly delays GVHD. However, the combination of inhibitors appears additive at best in vivo and does not completely eliminate GVHD. The bispecific inhibitor AJI-100 significantly reduced GVHD and improved survival compared to vehicle control. It was surmised that the apparent enhanced in vivo activity of AJI-100 compared to alisertib plus TG101348 may be due to inherent kinase selectivity. The ratio of Aurora kinase A to kinase B inhibition by AJI-100 is greater than alisertib. This could contribute to enhanced impairment of T cell costimulation by AJI-100 and secondarily enhance efficacy. Although the role of AMPK in GVHD is unknown, mouse models of inflammatory colitis using AMPK-deficient T cells suggest that AMPK neutralization may have immunosuppressive properties as well. Therefore, off-target inhibition of AMPK by AJI-100 could be beneficial in controlling GVHD. However, the immunosuppressive effects of the combination of the JAK2 inhibitor TG101348 and the Aurora kinase A inhibitor alisertib coupled with the potent activity of AJI-100 suggests that the ability of AJI-100 to prevent GVHD is likely due to its dual JAK2/Aurora kinase A inhibitory activity. Blockade of Aurora kinase A or JAK2 induces pathway-specific effects on developing i$T_{reg}$ and $T_H17$. First, blockade of Aurora kinase A and JAK2 permits the differentiation of highly suppressive, alloantigen-specific, CD39$^+$ i$T_{reg}$. Patients with rheumatoid arthritis lacking sufficient CD39$^+$ $T_{regs}$ experience greater rates of methotrexate failure and poor clinical outcomes, suggesting that dual Aurora kinase A/JAK2 inhibition may benefit other inflammatory conditions. Our data support that the enhanced iT$_{reg}$ potency is largely a function of Aurora kinase A inhibition because iT$_{regs}$ exposed to alisertib, an Aurora kinase A-specific inhibitor, eliminated T$_{conv}$ proliferation. On the other hand, alisertib was unable to prevent T$_H$17 differentiation among naïve CD4$^+$ T cells responding to alloantigen. Given that IL-6 receptor signal transduction facilitates T$_H$17 development, our data confirm that JAK2 blockade is capable of restraining STAT5 phosphorylation and resultant T$_H$17 differentiation. Additionally, JAK2 inhibition appears to exhibit less inhibition of iT$_{regs}$ compared to Aurora kinase A blockade. Last, inhibition of JAK2, Aurora kinase A, or both JAK2 and Aurora kinase A equally impaired the T$_H$1 response in vitro. Selective inhibition of Aurora kinase A and JAK2 paired with preserved common gamma-chain cytokine signaling establishes a platform to control alloreactivity while permitting antigen-specific T$_{reg}$ and CTL responses. However, there are several limitations of this study that deserve further consideration. Although the xenogeneic model is well suited to test whether concurrent Aurora kinase A/JAK2 inhibition can prevent GVHD mediated by human cells in vivo, it does not entirely replicate human GVHD pathogenesis. The recipient mice do not receive transplant conditioning, unlike human patients, and this may affect GVHD target-organ injury, host antigen presentation, and the production of relevant cytokines such as IL-6. Our work demonstrates that AJI-100 permits the generation and function of antitumor CTL, but it is important to recognize that such experiments are supportive and not definitive in assessing whether the bispecific inhibitor preserves GVL in vivo. Last, small-molecule inhibitors can exhibit off-target inhibition, as observed with AJI-100 and its suppression of AMPK. Unlike molecular knockout strategies, off-target effects by pharmacologic inhibitors may be immunologically relevant and should be considered when interpreting such data. CNI-free GVHD prophylaxis is an important concept in improving patient outcomes after clinical transplantation. The challenges of CNI-based GVHD prevention are clear because CNIs offer incomplete protection from severe gVHD and render the donor immune system poorly equipped to counter posttransplant relapse. Given that targeting Aurora kinase A and JAK2 significantly reduces activated T$_{conv}$ while permitting T$_{regs}$ and tumor-specific CTL, the concept described here may represent a translatable CNI free approach at GVHD prevention. A limited number of CNI-free GVHD prophylaxis strategies currently exist and include T cell depletion of the allograft or the use of posttransplant cyclophosphamide The bispecific inhibitor AJI-100 is an attractive alternative because it does not require ex vivo allograft modification or the need to expose freshly infused donor stem cells to potent alkylators. Hence, further investigation of dual Aurora kinase A/JAK2 inhibition is merited to promote selective control of donor immune responses after alloHCT.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound selected from:

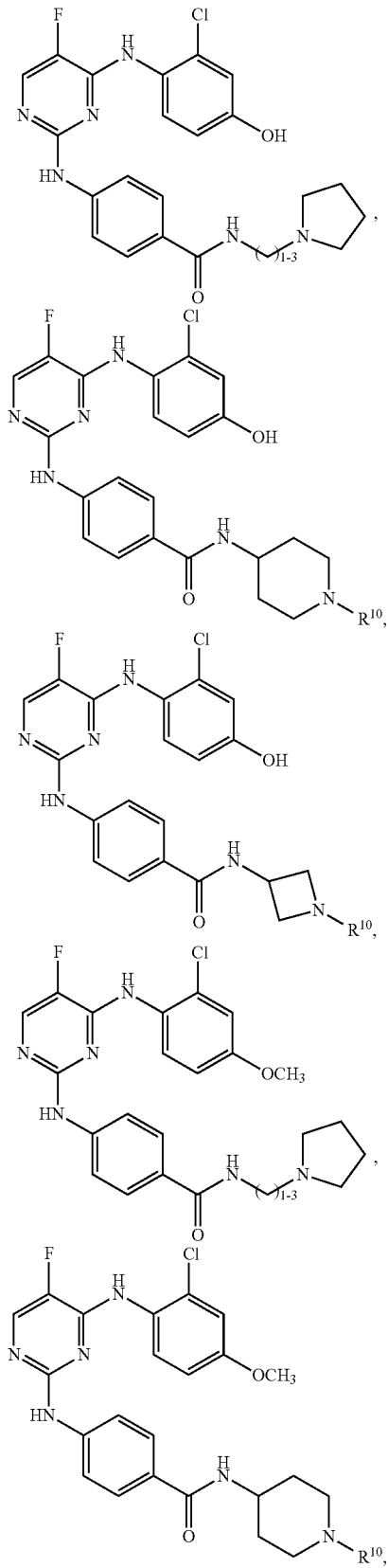

-continued

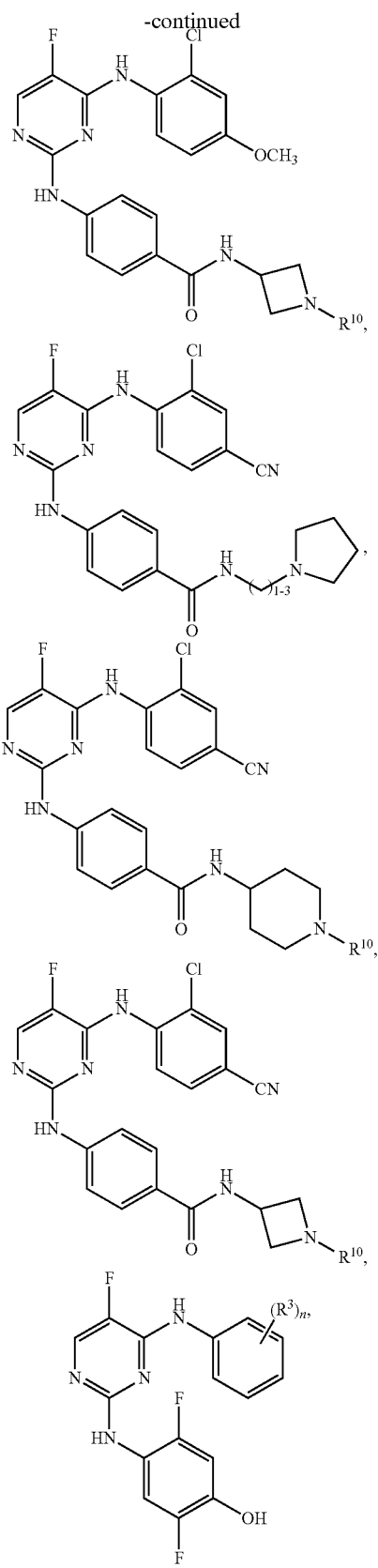

-continued

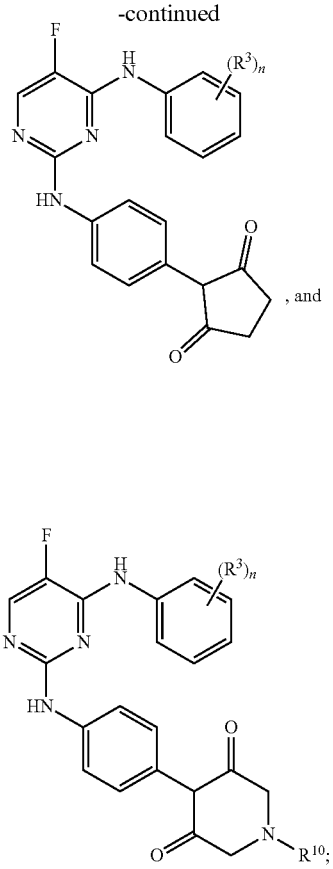

wherein:

each R³ is selected, independently, from the group consisting of $SO_2NH_2$, $SO_2NHR^5$, $NHSO_2R^5$, $NHCO_2R^5$, $NHC(O)R^5$, $NHCONHR^5$, F, Cl, Br, I, $NO_2$, $C_1$-$C_6$ alkyl, $C_1$-$C_6$ alkoxy, cycloheteroaryl, and fused cycloheteroalkyl, optionally substituted with sulfonyl;

each R⁵ is selected, independently, from the group consisting of optionally substituted $C_1$-$C_6$ alkyl, optionally substituted cycloalkyl, optionally substituted heteroaryl, and optionally substituted heteroalkyl, wherein optionally substituted substituents are optionally substituted with $C_1$-$C_6$ alkyl, $C_1$-$C_6$ alkoxyl, cycloalkyl, cycloheteroalkyl, alkenyl, alkynyl, aryl, heteroaryl, aldehyde, amino, carboxylic acid, ester, ether, halide, hydroxy, ketone, nitro, oxo, silyl, sulfo-oxo, sulfonyl, sulfone, sulfoxide, or thiol;

n is 1-5; and

R¹⁰ is hydrogen, $C_1$-$C_6$ alkyl, or $C_1$-$C_6$ alkyl-OH.

2. A method for reducing the risk of, preventing, or treating graft versus host disease (GVDH) in a subject comprising administering to the subject a compound of claim 1.

3. The method of claim 2, wherein the GVDH is attributed to a solid organ transplant, a tissue graft, or a cellular transplant.

* * * * *